(12) United States Patent
Kong et al.

(10) Patent No.: US 6,734,302 B2
(45) Date of Patent: May 11, 2004

(54) CIS-IMIDAZOLINES

(75) Inventors: Norman Kong, West Caldwell, NJ (US); Emily Aijun Liu, Nutley, NJ (US); Binh Thanh Vu, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/316,695

(22) Filed: Dec. 11, 2002

(65) Prior Publication Data
US 2003/0153580 A1 Aug. 14, 2003

Related U.S. Application Data
(60) Provisional application No. 60/390,874, filed on Jun. 21, 2002, and provisional application No. 60/341,714, filed on Dec. 18, 2001.

(51) Int. Cl.[7] .................... C07D 233/22; C07D 233/24; C07D 233/26; A61K 31/4164
(52) U.S. Cl. ...................... 544/139; 544/370; 546/210; 548/334.1
(58) Field of Search ................. 544/139, 370; 546/210; 548/334.1

(56) References Cited

U.S. PATENT DOCUMENTS
5,182,268 A 1/1993 Ahmed

FOREIGN PATENT DOCUMENTS
WO  WO 92/03421  3/1992
WO  WO 00 19994  4/2000

OTHER PUBLICATIONS
Hunter et al., Chem. Abstract 76:126506, 1972.*
Claudi et al., J. Med. Chem., 43, pp. 599–608 (2000).
Wells et al., J. Org. Chem., 37, pp. 2158–2161 (1972).
Harris et al., J. Org. Chem., 64, pp. 6019–6022 (1999).
Wells et al., Tetrahedron Letters, 37, pp. 6439–6442 (1996).
Hammouda et al., Egypt. J. Chem., 30, pp. 239–247 (1987).
Hunter D.H., et al., Canadian Journal of Chemistry, National Research Council, vol. 50, pp. 669–677 (1972).
Meegalla S.K., et . al., Journal of Medicinal Chemistry, American Chemical Society, vol. 37, No. 20, pp. 3434–3439 (1994).

* cited by examiner

Primary Examiner—Deepak Rao
(74) Attorney, Agent, or Firm—George W. Johnston; Patricia S. Rocha-Tramaloni; Bernard Lau

(57) ABSTRACT

The present invention provides compounds according to formula I and formula II and pharmaceutically acceptable salts and esters thereof, having the designations provided herein and which inhibit the interaction of MDM2 protein with a p53-like peptide and have antiproliferative activity.

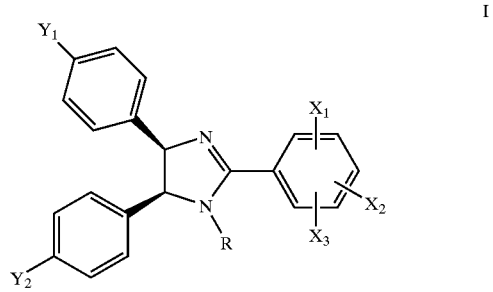

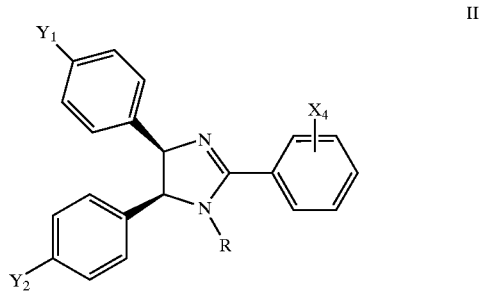

41 Claims, No Drawings

CIS-IMIDAZOLINES

PRIORITY TO PROVISIONAL APPLICATION(S) UNDER 35 U.S.C. §119(e)

This application claims priority under 35 U.S.C. §119(e) of provisional application(s) Ser. No. 60/390,874, filed Jun. 21, 2002 and Ser. No. 60/341,714, filed Dec. 18, 2001.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158–2161, report synthesis of imidazolines. Hunter et al., *Can. J. Chem.*, 1972, Vol. 50, pgs. 669–77, report the preparation of amarine and isoamarine compounds which had previously been studied for chemiluminescence (McCapra et al. *Photochem. and Photobiol.* 1965, 4, 1111–1121). Zupanc et al. *Bull. Soc. Chem. & Tech.* (Yugoslavia) 1980–81, 27/28, 71–80, report the use of triaryl imidazolines as starting materials in the preparation of EDTA derivatives. EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

SUMMARY OF THE INVENTION

The present invention provides at least one compound selected from a compound of formula I

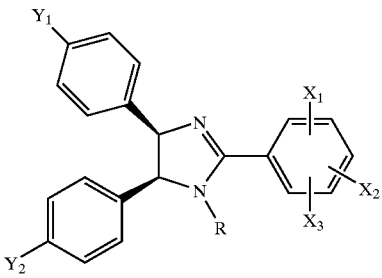

and the pharmaceutically acceptable salts and esters thereof, wherein

R is —C═OR1, wherein R1 is C1–C4 alkyl, —C═CHCOOH, —NHCH$_2$CH$_2$R2, —N(CH$_2$CH$_2$OH)CH$_2$CH$_2$OH, —N(CH$_3$)CH$_2$CH$_2$NCH$_3$, —N(CH$_3$)CH$_2$CH$_2$N(CH$_3$)CH$_3$, saturated 4-, 5- and 6-membered rings, saturated and unsaturated 5- and 6-membered rings containing at least one hetero atom wherein the hetero atom is selected from S, N and O and being optionally substituted with a group selected from lower alkyl, —C═O—R5, —OH, lower alkyl substituted with hydroxy, lower alkyl substituted with —NH$_2$, N-lower alkyl, —SO$_2$CH$_3$, ═O, —CH$_2$C═OCH$_3$, and 5- and 6-membered saturated rings containing at least one hetero atom selected from S, N and O, wherein R5 is selected from H, lower alkyl, —NH$_2$, —N-lower alkyl, lower alkyl substituted with hydroxy, and lower alkyl substituted with NH$_2$, wherein R2 is selected from —N(CH$_3$)CH$_3$, —NHCH$_2$CH$_2$NH$_2$, —NH$_2$, morpholinyl and piperazinyl, X$_1$, X$_2$ and X$_3$ are independently selected from —OH, C1–C2 alkyl, C1–C5 alkoxy, —Cl, —Br, —F, —CH$_2$OCH$_3$, and —CH$_2$OCH$_2$CH$_3$, or one of X$_1$, X$_2$ or X$_3$ is H and the other two are independently selected from hydroxy, lower alkyl, lower alkoxy, Cl, Br, F, CF$_3$ —CH$_2$OCH$_3$, —CH$_2$OCH$_2$CH$_3$ —OCH$_2$CH$_2$R3, —OCH$_2$CF$_3$, and —O—R4, or one of X$_1$, X$_2$ or X$_3$ is H and the other two taken together with the two carbon atoms and the bonds between them from the benzene ring to which they are substituted form a 6-membered saturated ring that contains at least one hetero atom selected from S, N, and O, wherein R3 is selected from —F, —OCH$_3$, —N(CH$_3$)CH$_3$, unsaturated 5-membered rings containing at least one hetero atom wherein the hetero atom is selected from S, N and O, wherein R4 is a 3- to 5-membered saturated ring and Y$_1$ and Y$_2$ are each independently selected from —Cl, —Br, —NO$_2$, —C≡N and —C≡CH.

The present invention also provides at least one compound selected from a compound of formula II

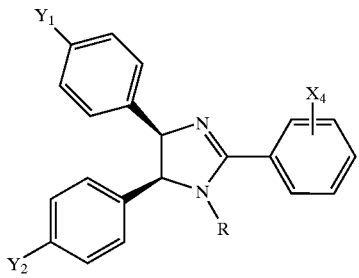

and the pharmaceutically acceptable salts and esters thereof, wherein

R is —C=OR1, wherein R1 is selected from C1–C4 alkyl, saturated 5- and 6-membered rings, saturated 5- and 6-membered rings containing at least one hetero atom wherein the hetero atom is selected from S, N and O and being optionally substituted with a group selected from C1–C2 alkyl, C1–C3 alcohol, —N(CH$_3$)CH$_3$, and —C=OCH$_3$, and 5- and 6-membered rings containing at least one hetero atom wherein the hetero atom is selected from S, N, and O, $X_4$ is selected from C1–C2 alkyl, C1–C5 alkoxy, —Cl, —Br, —F, —OCH$_2$C=OOQ, —OCH$_2$ cyclopentyl, —CH$_2$OCH$_2$-phenyl, saturated and unsaturated 5- and 6-membered rings, saturated and unsaturated 5- and 6-membered rings containing at least one hetero atom wherein the hetero atom is selected from S, N and O, wherein Q is selected from H and lower alkyl, $Y_1$ and $Y_2$ are independently selected from —Cl, —Br, —NO$_2$, —C≡N and —C≡CH, with the proviso that where $Y_1$ and $Y_2$ are both —Cl, and R1 is —CH$_3$ or phenyl, then $X_4$ is not —Cl.

DETAILED DESCRIPTION OF THE INVENTION

The present invention provides cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound selected from a compound of formula I

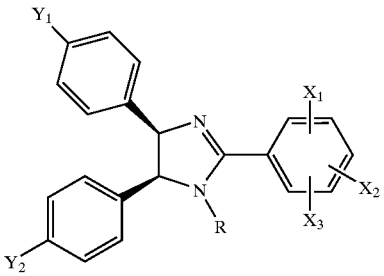

and the pharmaceutically acceptable salts and esters thereof, wherein

R is —C=OR1, wherein R1 is C1–C4 alkyl, —C=CHCOOH, —NHCH$_2$CH$_2$R2, —N(CH$_2$CH$_2$OH)CH$_2$CH$_2$OH, —N(CH$_3$)CH$_2$CH$_2$NCH$_3$, —N(CH$_3$)CH$_2$CH$_2$N(CH$_3$)CH$_3$, saturated 4-, 5- and 6-membered rings, saturated and unsaturated 5- and 6-membered rings containing at least one hetero atom wherein the hetero atom is selected from S, N and O and being optionally substituted with a group selected from lower alkyl, —C=O—R5, —OH, lower alkyl substituted with hydroxy, lower alkyl substituted with —NH$_2$, N-lower alkyl, —SO$_2$CH$_3$, =O, —CH$_2$C=OCH$_3$, and 5- and 6-membered saturated rings containing at least one hetero atom selected from S, N and O, wherein R5 is selected from H, lower alkyl, —NH$_2$, —N-lower alkyl, lower alkyl substituted with hydroxy, and lower alkyl substituted with NH$_2$, wherein R2 is selected from —N(CH$_3$)CH$_3$, —NHCH$_2$CH$_2$NH$_2$, —NH$_2$, morpholinyl and piperazinyl, $X_1$, $X_2$ and $X_3$ are independently selected from —OH, C1–C2 alkyl, C1–C5 alkoxy, —Cl, —Br, —F, —CH$_2$OCH$_3$, and —CH$_2$OCH$_2$CH$_3$, or one of $X_1$, $X_2$ or $X_3$ is H and the other two are independently selected from hydroxy, C1–C2 alkyl, C1–C5 alkoxy, Cl, Br, F, CF$_3$ —CH$_2$OCH$_3$, —CH$_2$OCH$_2$CH$_3$—OCH$_2$CH$_2$R3, —CH$_2$CF$_3$, and —O—R4, or one of $X_1$, $X_2$ or $X_3$ is H and the other two taken together with the two carbon atoms and the bonds between them from the benzene ring to which they are substituted form a 6-membered saturated ring that contains at least one hetero atom selected from S, N, and O, wherein R3 is selected from —F, —OCH$_3$, —N(CH$_3$)CH$_3$, unsaturated 5-membered rings containing at least one hetero atom wherein the hetero atom is selected from S, N and O, wherein R4 is a 3- to 5-membered saturated ring and $Y_1$ and $Y_2$ are each independently selected from —Cl, —Br, —NO$_2$, —C≡N, and —C≡CH.

The present invention also provides at least one compound selected from a compound of formula II

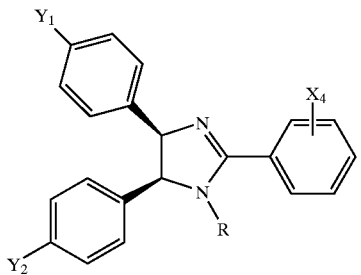

and the pharmaceutically acceptable salts and esters thereof, wherein

R is —C═OR1,
wherein R1 is selected from C1-C4 alkyl, saturated 5- and 6-membered rings, saturated 5- and 6-membered rings containing at least one hetero atom wherein the hetero atom is selected from S, N and O and being optionally substituted with a group selected from C1–C2 alkyl, C1–C3 alcohol, —N(CH$_3$)CH$_3$, and —C═OCH$_3$, and 5- and 6-membered rings containing at least one hetero atom wherein the hetero atom is selected from S, N, and O, X$_4$ is selected from C1–C2 alkyl, C1–C5 alkoxy, —Cl, —Br, —F, —OCH$_2$C═OOQ, —OCH$_2$ cyclopentyl, —CH$_2$OCH$_2$-phenyl, saturated and unsaturated 5- and 6-membered rings, saturated and unsaturated 5- and 6-membered rings containing at least one hetero atom wherein the hetero atom is selected from S, N and O, wherein Q is selected from H and lower alkyl, Y$_1$ and Y$_2$ are independently selected from —Cl, —Br, —NO$_2$, —C≡N and —C≡CH, with the proviso that where Y$_1$, and Y$_2$ are both —Cl, and R1 is —CH$_3$ or phenyl, then X$_4$ is not —Cl.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"IC$_{50}$" refers to the concentration of a particular compound required to inhibit 50% of a specific measured activity. IC$_{50}$ can be measured, inter alia, as is described subsequently.

"Alkyl" denotes a straight-chained or branched saturated aliphatic hydrocarbon. "Lower alkyl" groups denote C1–C6 alkyl groups and include methyl, ethyl, propyl, isopropyl, butyl, t-butyl, 2-butyl, pentyl, hexyl, and the like. Generally, lower alkyl is preferably C1–C4 alkyl, and more preferably C1–C3 alkyl.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 70 ηM to about 100 μM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The compounds of the present invention can be prepared according to the following Schemes. The following definitions are provided as applicable to the synthesis schemes:

V$^1$, V$^2$, V$^3$, V$^4$, V$^5$ are each independently selected from:
Hydrogen,
—OV$^6$,
—SV$^7$, —$NV^8V^9$,
—$CONV^8V^9$,
—$COOV^{10}$,
halogen,
nitro,
trifluoromethyl,
lower alkyl, which optionally may be substituted by $V^{11}$, and
cycloalkyl;

$V^1$, $V^2$ together may form part of a heterocycle with one or more heteroatoms, which optionally may be substituted by $V^{10}$.

$V^2$, $V^3$ together may form part of a heterocycle with one or more heteroatoms, which optionally may be substituted by $V^{10}$.

$Y^1$, $Y^2$ are each independently selected from:
—Cl,
—Br,
nitro,
cyano; and
—C≡CH V, is selected from $COV^{12}$ and $CONV^{13}V^{14}$, $V^6$ is selected from the group of:
hydrogen,
lower alkyl, which optionally may be substituted by $V^{11}$, and cycloalkyl;

$V^7$ is selected from the group of:
hydrogen, and
lower alkyl;

$V^8$, $V^9$ are each independently selected from the group of:
hydrogen,
lower alkyl, and
cycloalkyl;

$V^8$, $V^9$ together may form part of a heterocycle with one or more heteroatoms;

$V^{10}$ is selected from the group of:
hydrogen,
lower alkyl, and
cycloalkyl;

$V^{11}$ is selected from the group of:
—$CONV^8V^9$,
—$NV^8V^9$,
—$COOV^{10}$,
aryl,
halogen,
lower alkoxy,
morpholinyl, and
heterocycles;

$V^{12}$ is selected from the group of
hydrogen,
lower alkyl,
cycloalkyl,
aryl,
heterocycle, and
heteroaryl;

$V^{13}$ and $V^{14}$ are independently selected from the group of
lower alkyl,
cycloalkyl,
lower alkyl substituted by $V^{11}$; or $V^{13}$ and $V^{14}$ together may form part of a
hetercycle such as morpholine, piperidine, pyrrolidine and piperazine;

The piperazine may be substituted by
lower alkyl,
hydroxyalkyl,
acyl, acyl substituted with hydroxy and amino,
alkylsulfonyl,
$CONH_2$,
$CONV^8V^9$,
keto,
hydroxy;

The piperidine may be substituted by
dialkyl amine,
pyrrolidine, or
piperidine.

Scheme I

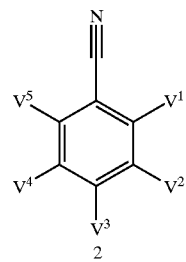

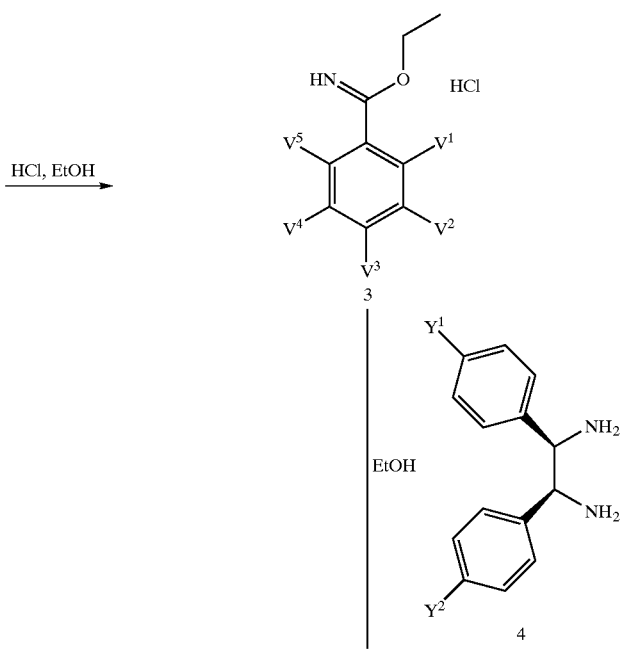

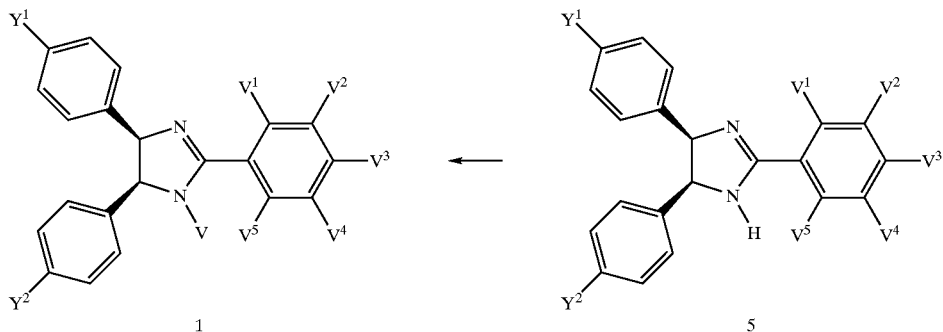

A compound of formula 2, a known compound or a compound prepared by known methods, is converted to a compound of formula 3 using hydrogen chloride gas in ethanol over a period of several hours to several weeks. A formula of compound 3 is then reacted with a compound of formula 4 in a solvent such as ethanol, at a temperature of 60 to 100° C. to afford a compound of formula 5.

When V is $COV^{12}$, a compound of formula 5 is reacted with a compound of formula $ClCOV^{12}$ (a known compound or a compound prepared by known methods) at 0° C. to 25° C. in the presence a base such as triethylamine to give a compound of formula 1.

When V is $CONV^{13}V^{14}$(providing that $NHV^{13}V^{14}$ is a known compound or a compound prepared by known methods), a compound of formula 5 is reacted with phosgene at 0° C. in the presence of triethylamine followed by the treatment of a compound of formula $HNV^{13}V^{14}$ to afford a compound of formula 1.

Scheme II

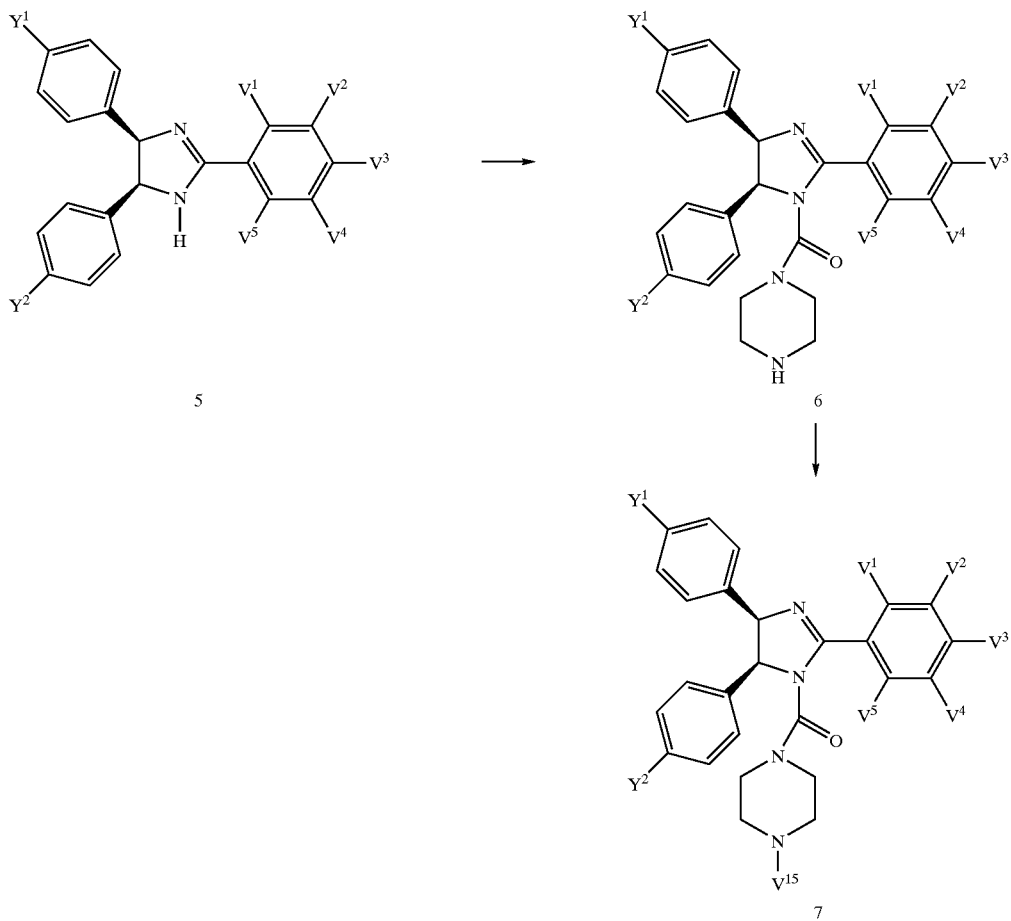

As set forth in Scheme II, when $V^{15}$ substituted piperazines are not commercially available ($V^{15}$ may be acyl, acyl substituted with hydroxyl, amino, protected amino and sulfonyl), a compound of formula 7 is prepared as follows: a compound of formula 5 is reacted with phosgene and triethylamine followed by the treatment of piperazine to afford a compound of formula 6. A compound of 6 is reacted with $V^{15}X$ to give a compound of formula 7.

As set forth in Scheme III, a compound of formula 8 can be prepared from a compound of formula 6 by the reaction of phosgene and triethylamine followed by the treatment of $NHV^8V^9$, a known compound or a compound prepared by known methods.

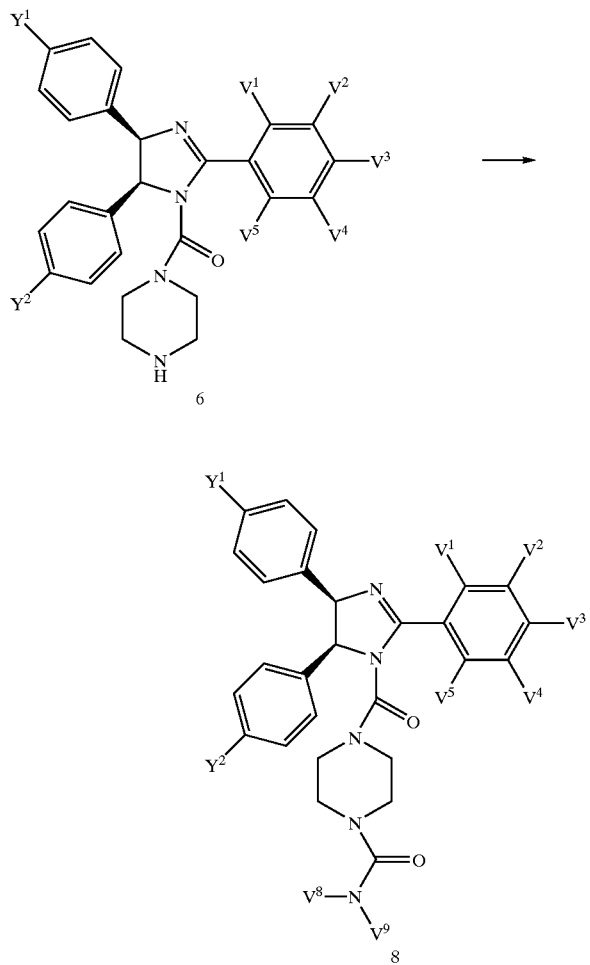

The meso-1,2-diamine of formula 4 ($Y^1=Y^2$) can be prepared according to the literature procedures (see Jennerwein, M. et al. Cancer Res. Clin. Oncol. 1988, 114, 347–58; Vogtle, F.; Goldschmitt, E. Chem. Ber. 1976,109, 140).

If it is desired to prepare a compound of formula 4 wherein $Y^1 \neq Y^2$, modifications to the existing procedure can be made. An equal molar mixture of the benzaldehydes and meso-1,2-bis-(2-hydroxy-phenyl)-ethane-1,2-diamine can be used to afford a mixture of 1,2-diamines (Scheme IV). Knölker, H. J., et al. Tetrahedron Letters 1998, 39, p. 9407. It was then reacted with di-t-butyldicarbonate in the presence of dimethylaminopyridine to give a compound of formula 9 after HPLC purification. Compound 9 is then converted to a compound of formula 4 by the treatment of hydrobromic acid in hot acetic acid.

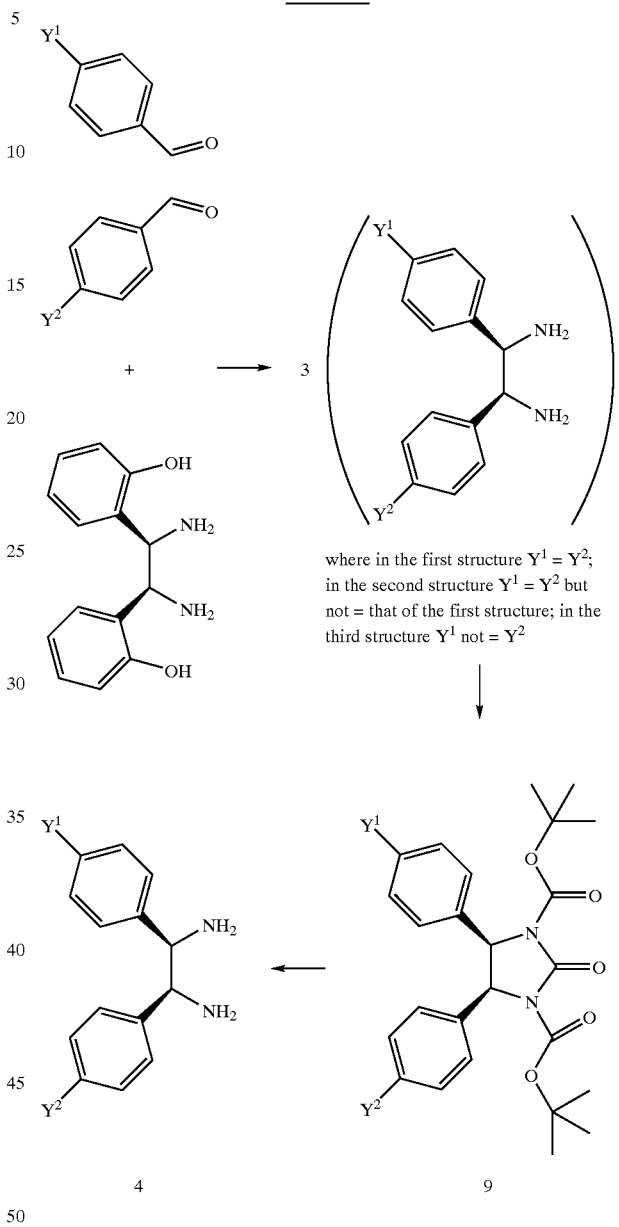

If it is desired to prepare a compound of formula 2 which is not commercially available, many synthetic methods known in the art can be employed. Suitable processes for synthesizing these benzonitriles are provided in the examples. Following schemes illustrate some of these methods.

A compound of formula 11 ($V^{16}$ can be any suitable group such as $V^1$, $V^2$, $V^3$, $V^4$, or $V^5$) can be prepared by alkylation of a compound of formula 10 with $V^6X$ (X=Cl, Br, I) using conventional methods (scheme V). The phenoxide anion is generated by a base such as cesium carbonate or potassium carbonate. The reaction typically is carried out in refluxing acetone. $V^6$ can also be introduced using Mitsunobu reaction (see for example, Hughes, D. L. Org React. 1992, 42, 335–656).

Scheme V

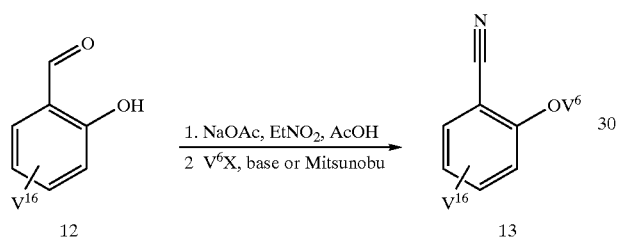

A compound of formula 12 ($V^{16}$ can be any suitable group such as $V^1$, $V^2$, $V^3$, $V^4$, or $V^5$) can be converted into the benzonitrile 13 using literature procedures (Karmarkar, S. N; Kelkar, S. L.; Wadia, M. S. *Synthesis* 1985, 510–512; Bergeron, R. J. et al. *J. Med. Chem.* 1999, 42, 95–108). V group can then be introduced using $V^6X$ (X=Cl, Br, I) or Mitsunobu reaction to give the benzonitrile 13 (scheme VI).

Scheme VI

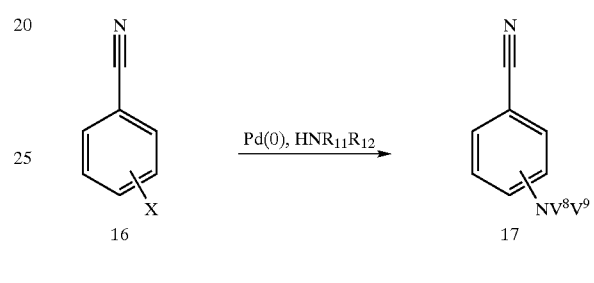

A compound of formula 15 can be prepared by bromination or iodination of phenol 14 (Scheme VII), ($V^{16}$ can be any suitable group such as $V^1$, $V^2$, $V^3$, $V^4$, or $V^5$). Reaction conditions such as N-bromosuccinamide/tetrahydrofuran or iodine/thallium(I) acetate can be utilized (see for example, Carreno, M. C.; Garcia Ruano, J. L.; Sanz, G.; Toledo, M. A.; Urbano, A. *Synlett* 1997, 1241–1242; Cambie, R. C.; Rutledge, P. S.; Smith-Palmer, T.; Woodgate, P. D. *J. Chem. Soc., Perkin Trans.* 1 1976, 1161–4). $V^5$ group can then be introduced using $V^6X$ (X=Cl, Br, I) or Mitsunobu reaction. Methods of converting aromatic halides to the corresponding nitrites are known in the art (see for example, Okano, T.; Iwahara, M.; Kiji, J., *Synlett* 1998, 243). Cyanation of the halide 15 (X'=Br, I) can be accomplished using zinc cyanide with a catalyst such as tetrakis(triphenylphosphine) palladium (0). Solvents such dimethylformamide can be used and the reaction temperature is between 80–110° C.

Scheme VII

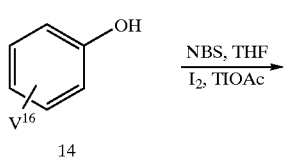

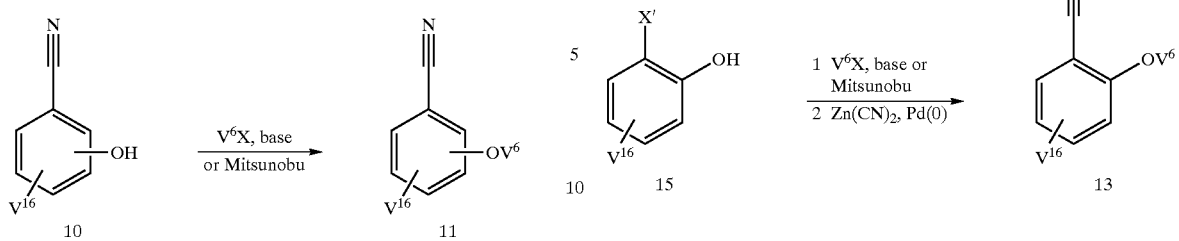

In scheme VIII, amination of aromatic halide 16 using $HNV^7V^8$ and palladium catalyst can be utilized to provide the benzonitrile of formula 17 (see for example, Harris, M. C.; Geis, O.; Buchwald, S. L. *J. Org. Chem.* 1999, 64, 6019).

Scheme VIII

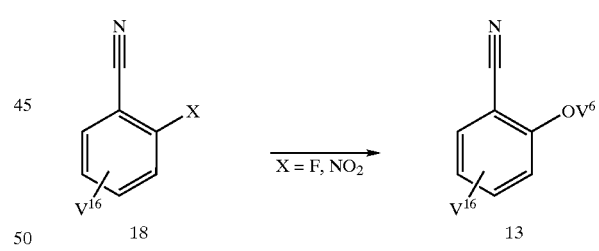

A compound of formula 13 ($V^{16}$ can be any suitable group such as $V^1$, $V^2$, $V^3$, $V^4$, or $V^5$) can be prepared by nucleophilic substitution of 2-halobenzonitrile 18 (scheme IX). (see for example, X=F: Wells, K. M.; Shi, Y.-J.; Lynch, J. E.; Humphrey, G. R.; Volante, R. P.; Reider, P. J. *Tetrahedron Lett.* 1996, 37, 6439–6442; X=$NO_2$: Harrison, C. R.; Lett, R. M.; McCann, S. F.; Shapiro, R.; Stevenson, T. M. WO 92/03421, 1992).

Scheme IX

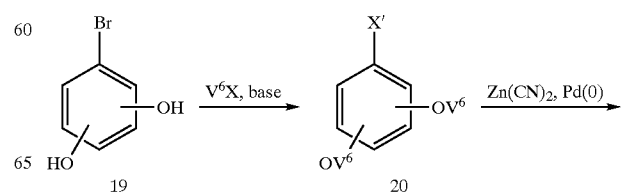

To prepare the benzonitrile of formula 21 wherein $V^1$, $V^2$, $V^3$, $V^4$, or $V^5$=$OV^6$, sequential alkylation of the diol 19 with suitable $V^6X$ (X=Cl, Br, I) are used. The bromides 20 are then converted to the nitrites 21 using zinc cyanide and Pd(0) catalyst (scheme X).

Scheme X

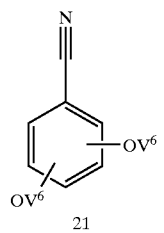

Certain of the following Examples refer to Examples provided in U.S. Provisional application Serial No. 60/341,729 and Serial No. 60/390,876 both entitled CIS-IMIDAZOLINES. The Examples of these Provisional applications are incorporated herein by reference.

The present invention encompasses the following Examples. For structural formulas shown, it is understood that oxygen and nitrogen atoms with available elections have a hydrogen bound thereto, as indicated by compound name.

EXAMPLE 1

1-[4,5-Bis-(4-chloro-phenyl)-2-(2,4-dimethoxy-phenyl)-4,5-dihydro-imidazol-1-yl]-2-methyl-propan-1-one

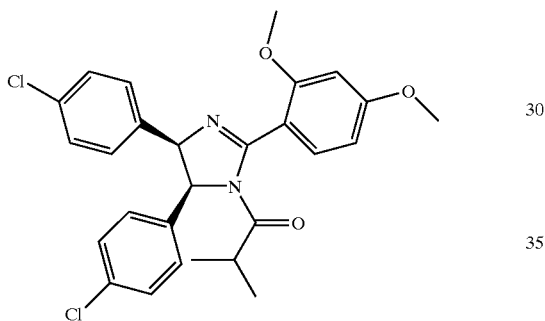

Hydrogen chloride gas was passed through a solution of 2,4-dimethoxy-benzonitrile (5.20 g, 32 mmol) in anhydrous ethanol (200 mL) at 0° C. After 7 h, hydrogen chloride gas was stopped and the reaction mixture was stirred at room temperature overnight. The solvent was removed and the residue was triturated in diethyl ether to afford ethyl 2,4-dimethoxy-benzimidate hydrochloride (4.5 g, 57%). It was used without further purification.

A solution of meso-1,2-bis-(4-chloro-phenyl)-ethane-1,2-diamine (1.21 g, 4.30 mmol, prepared according to the procedure described by Jennerwein, M. et al. *Cancer Res. Clin. Oncol.* 1988, 114, 347–8; Vogtle, F.; Goldschmitt, E. *Chem. Ber.* 1976, 109, 1–40) and ethyl 2,4-dimethoxy-benzimidate hydrochloride (1.58 g, 6.43 mmol) in ethanol (30 mL) was heated at reflux for 16 h. The reaction mixture was basified with sodium bicarbonate solution (10 mL) and extracted with ethyl acetate. The organic extracts were washed with brine and dried over anhydrous sodium sulfate. The solids were then filtered off, and the filtrate was concentrated in vacuo. Purification of the crude residue by flash chromatography (Biotage system, KP-Sil™ 32–63 μm, 60 Å silica gel) eluting with 2–6% methanol in methylene chloride yielded 4,5-bis-(4-chloro-phenyl)-2-(2,4-dimethoxy-phenyl)-4,5-dihydro-1H-imidazole (1.10 g, 60%).

Isobutyryl chloride (19 μL, 0.18 mmol) was added to a solution of triethylamine (25 μL, 0.18 mmol) and 4,5-bis-(4-chloro-phenyl)-2-(2,4-dimethoxy-phenyl)-4,5-dihydro-1H-imidazole (70 mg, 0.164 mmol). The reaction mixture was stirred at room temperature for 2 h. It was diluted with methylene chloride and washed with water and brine, and dried over sodium sulfate. The solvents were removed under reduced pressure and chromatography of the residue over silica gel using 0.5–1% methanol in methylene chloride gave 1-[4,5-bis-(4-chloro-phenyl)-2-(2,4-dimethoxy-phenyl)-4,5-dihydro-imidazole-1-yl]-2-methyl-propan-1-one. HR-MS (EI, m/z) calculated for $C_{27}H_{26}N_2O_3Cl_2$ ($M^+$) 496.1320, observed 496.1319.

EXAMPLE 2

In a similar manner as described in example 1, the following compounds were prepared.

a) 1-[4,5-Bis-(4-chloro-phenyl)-2-(2,4-dimethoxy-phenyl)-4,5-dihydro-imidazol-1-yl]ethanone. HR-MS (EI, m/z) calculated for $C_{25}H_{22}N_2O_3Cl_2$ ($M^+$) 468.1007, observed 468.1020

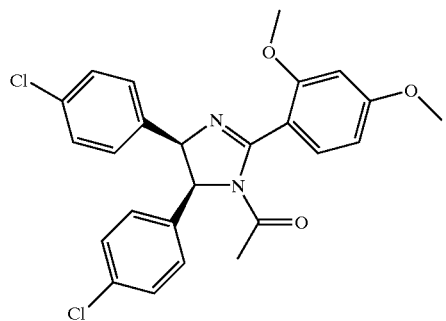

b) 1-[4,5-Bis-(4-chloro-phenyl)-2-(2,4-dimethoxy-phenyl)-4,5-dihydro-imidazol-1-yl]-2,2-dimethyl-propan-one, HR-MS (EI, m/z) calculated for $C_{28}H_{28}N_2O_3Cl_2$ ($M^+$) 510.1477, observed 510.1476.

c) [4,5-Bis-(4-chloro-phenyl)-2-(2,4-dimethoxy-phenyl)-4,5-dihydro-imidazol-1-yl]-cyclopentyl-methanone. HR-MS (EI, m/z) calculated for $C_{29}H_{28}N_2O_3Cl_2$ ($M^+$) 522.1477, observed 522.1470.

d) [4,5-Bis-(4-chloro-phenyl)-2-(2,4-dimethoxy-phenyl)-4,5-dihydro-imidazol-1-yl]-cyclohexyl-methanone. HR-MS (EI, m/z) calculated for $C_{30}H_{30}N_2O_3Cl_{12}$ ($M^+$) 536.1633, observed 536.1633.

e) [4,5-Bis-(4-chloro-phenyl)-2-(2,4-dimethoxy-phenyl)-4,5-dihydro-imidazol-1-yl]-thiophen-2-yl-methanone. HR-MS (EI, m/z) calculated for $C_{28}H_{20}N_2O_3Cl_2S$ [(M-2H)$^+$]534.0572, observed 534.0566.

f) [4,5-Bis-(4-chloro-phenyl)-2-(2,4-dimethoxy-phenyl)-4,5-dihydro-imidazol-1-yl]-isoxazol-5-yl-methanone. HR-MS (EI, m/z) calculated for $C_{27}H_2N_3O_4Cl_{12}$ ($M^+$) 521.0909, observed 521.0892.

g) [4,5-Bis-(4-chloro-phenyl)-2-(2,4-dimethoxy-phenyl)-4,5-dihydro-imidazol-1-yl]-furan-2-yl-methanone. HR-MS (EI, m/z) calculated for $C_{28}H_{20}N_2O_4Cl_2$[(M-2H)$^+$]518.0800, observed 518.0802.

h) 1-[4,5-Bis-(4-chloro-phenyl)-2-(2-methoxy-phenyl)-4,5-dihydro-imidazol-1-yl]-2-methyl-propan-1-one. HR-MS (EI, m/z) calculated for $C_{26}H_{25}N_2O_2Cl_2[(M+H)^+]$ 467.1289, observed 467.1295

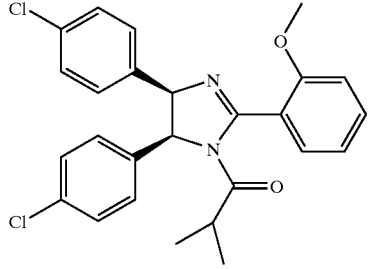

i) 1-[4,5-Bis-(4-chloro-phenyl)-2-p-tolyl-4,5-dihydro-imidazol-1-yl]-ethanone. HR-MS (EI, m/z) calculated for $C_{24}H_{20}N_2OCl_2$ $(M^+)$ 422.0953, observed 422.0950.

j) {4-[4,5-Bis-(4-chloro-phenyl)-1-isobutyryl-4,5-dihydro-1H-imidazol-2-yl]-phenoxy}-acetic acid ethyl ester. HR-MS (ES, m/z) calculated for $C_{29}H_{29}N_2O_4Cl_2$ $[(M+H)^+]$539.1499, observed 539.1506. The starting ethyl (4-cyano-phenoxy)-acetate was prepared from 4-hydroxy-benzonitrile and ethyl bromoacetate as described in Kirkiacharian, S.; Goma, J. R. et al. *Ann. Pharm. Fr.* 1989, 47, 16–23.

k) {4-[4,5-Bis-(4-chloro-phenyl)-1-isobutyryl-4,5-dihydro-1H-imidazol-2-yl]-phenoxy}-acetic acid was prepared by hydrolysis of {4-[4,5-bis-(4-chloro-phenyl)-1-isobutyryl-4,5-dihydro-1H-imidazol-2-yl]-phenoxy}-acetic acid ethyl ester. HR-MS (ES, m/z) calculated for $C_{27}H_{25}N_2O_4Cl_2$ $(M^+)$ 511.1186, observed 511.1191.

l) 2-Methyl-1-[2,4,5-tris-(4-chloro-phenyl)-4,5-dihydro-imidazol-1-yl]-propan-1-one. HR-MS (FAB, m/z) calculated for $C_{25}H_{22}N_2OCl_3[(M+H)^+]$471.0797, observed 471.0814.

m) 1-[4,5-Bis-(4-chloro-phenyl)-2-(4-methoxy-phenyl)-4,5-dihydro-imidazol-1-yl]-ethanone. HR-MS (FAB, m/z) calculated for $C_{24}H_{21}N_2O_2Cl_2[(M+H)^+]$ 439.0980, observed 439.0967.

n) 1-[4,5-Bis-(4-chloro-phenyl)-2-(2,3-dimethoxy-phenyl)-4,5-dihydro-imidazol-1-yl]-2-methyl-propan-1-one. HR-MS (ES, m/z) calculate for $C_{27}H_{27}N_2O_3Cl_2$ $[(M+H)^+]$497.1393, observed 497.1398

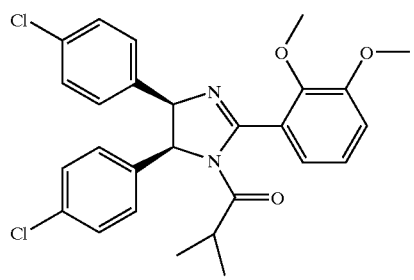

EXAMPLE 3

[4,5-Bis-(4-chloro-phenyl)-2-(2,4-dimethoxy-phenyl)-4,5-dihydro-imidazol-1-yl]-(4-methyl-piperazin-1-yl)-methanone

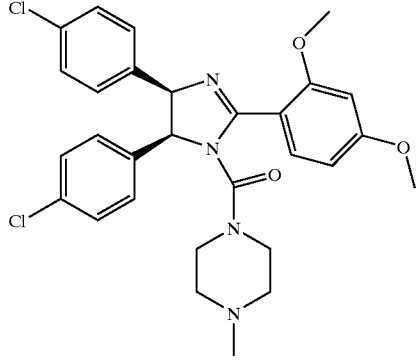

Phosgene (1.31 mL, 2.53 mmol, 1.93 M in toluene) was added dropwise to a cooled (0° C.) mixture of triethylamine (0.37 mL, 2.64 mmol) and 4,5-bis-(4-chloro-phenyl)-2-(2,4-dimethoxy phenyl)-4,5-dihydro-1H-imidazole (225 mg, 0.53 mmol, example 1) in THF (5 mL). The reaction mixture was stirred for 2.5 h and evaporated. The residue was kept under high vacuum for 30 min and was redissovled in methylene chloride (10 mL). The slurry was added dropwise to a solution of N-methylpiperazine (1.05 g, 10.48 mmol) in methylene chloride (5 mL). After 1 h, the reaction was worked up with aqueous sodium bicarbonate and extracted with methylene chloride. The organic extracts were washed with water and brine, and dried over sodium sulfate. Evaporation of the solvents and chromatography of the residue over silica gel using 1–4% methanol in methylene chloride gave 4,5-bis-(4-chloro-phenyl)-2-(2,4-dimethoxy-phenyl)-4,5-dihydro-imidazol-1-yl]-(4-methyl-piperazin-1-yl)-methanone. HR-MS (ES, m/z) calculated for $C_{29}H_{31}N_4O_3Cl_2[(M+H)^+]$553.1768, observed 553.1773.

EXAMPLE 4

In a similar manner as described in example 1 and 3, the following compounds were prepared.

a) [2-(2-Chloro-phenyl)-4,5-bis-(4-chloro-phenyl)-4,5-dihydro-imidazol-1-yl]-piperazin-1-yl-methanone. HR-MS (ES, m/z) calculated for $C_{26}H_{24}N_4OCl_3[(M+H)^+]$513.1009, observed 513.1013

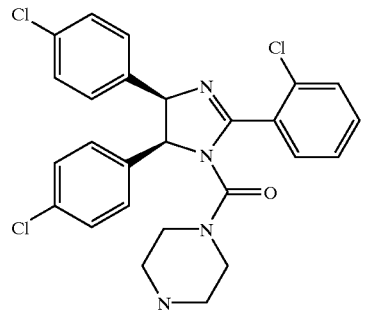

b) [2-(3-Bromo-phenyl)-4,5-bis-(4-chloro-phenyl)-4,5-dihydro-imidazol-1-yl]-piperazin-1-yl-methanone. HR-MS (ES, m/z) calculated for $C_{26}H_{24}N_4OCl_2Br$ $[(M+H)^+]$557.0505, observed 557.0506.

c) [2-Biphenyl-3-yl-4,5-bis-(4-chloro-phenyl)-4,5-dihydro-imidazol-1-yl]-(4-methyl -piperazin-1-yl)- methanone. HR-MS (ES, m/z) calculated for $C_{33}H_{31}N_4OCl_2[(M+H)^+]$ 569.1870, observed 569.1875.

d) [4,5-Bis-(4-chloro-phenyl)-2-(3-pyrrolidin-1-yl-phenyl)-4,5-dihydro-imidazol-1-yl]-piperazin-1-yl-methanone was synthesized from 3-pyrrolidinobenzonitrile (described in the previous patent). HR-MS (ES, m/z) calculated for $C_{30}H_{32}N_5OCl_2[(M+H)^+]$ 548.1979, observed 548.1980.

e) [4,5-Bis-(4-chloro-phenyl)-2-(2,4-dimethoxy-phenyl)-4,5-dihydro-imidazol-1-yl]-piperazin-1-yl-methanone. HR-MS (ES, m/z) calculated for $C_{28}H_{29}N_4O_3Cl_2[(M+H)^+]$ 539.1610 observed 539.1613

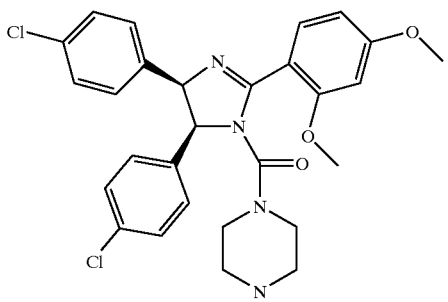

f) [4,5-Bis-(4-chloro-phenyl)-2-(2-fluoro-6-methoxy-phenyl)-4,5-dihydro-imidazol-1-yl]-[4-(2-hydroxy-ethyl)-piperazin-1-yl]-methanone. HR-MS (ES, m/z) calculated for $C_{29}H_{30}N_4O_3FCl_2[(M+H)^+]$ 571.1674, observed 571.1678.

g) 1-{4-[4,5-Bis-(4-bromo-phenyl)-2-(2,4-dimethoxy-phenyl)-4,5-dihydro-imidazole-1-carbonyl]-piperazin-1-yl}-ethanone. HR-MS (ES, m/z) calculated for $C_{30}H_{31}N_4O_4Br_2$ $[(M+H)^+]$ 669.0707, observed 669.0710.

h) [4,5-Bis-(4-bromo-phenyl)-2-(2,4-dimethoxy-phenyl)-4,5-dihydro-imidazol-1-yl]-[4-(2-hydroxy-ethyl)-piperazin-1-yl]-methanone. HR-MS (ES, m/z) calculated for $C_{30}H_{33}N_4O_4Br_2[(M+H)^+]$ 671.0863, observed 671.0870.

i) [4,5-Bis-(4-bromo-phenyl)-2-(2-methoxy-phenyl)-4,5-dihydro-imidazol-1-yl]-[4-(2-hydroxy-ethyl)-piperazin-1-yl]-methanone. HR-MS (ES, m/z) calculated for $C_{29}H_{31}N_4O_3Br_2[(M+H)^+]$ 641.0758, observed 641.0765.

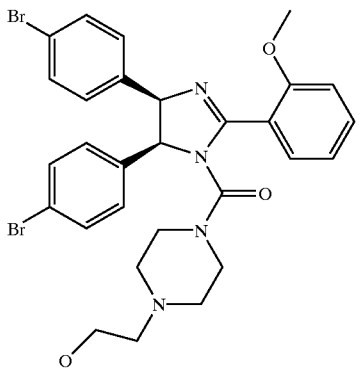

EXAMPLE 5

1-[5-(4-chloro-phenyl)-2-(4-methoxy-phenyl)-4-(4-nitro-phenyl)-4,5-dihydro-imidazol-1-yl]-2-methyl-propan-1-one and 1-[4-(4-Chloro-phenyl)-2-(4-methoxy-phenyl)-5-(4-nitro-phenyl)-5-(4-nitro-phenyl)-4,5-dihydro-imidazol-1-yl]-2-methyl-propan-1-one To a solution of meso-1,2-bis-(2-hydroxy-phenyl)-ethane-1,2-diamine (5.38 g, 22 mmol, prepared according to the procedure described by Vogtle, F.; Goldschmitt, E. Chem. Ber. 1976, 109, 1–40) in acetonitrile (50 mL) were added 4-nitrobenzaldehyde (3.33 g, 22 mmol) and 4-chlorobenzaldehyde (3.31 g, 23.5 mmol). The reaction mixture was heated at gentle reflux for 12 h. Upon cooling to room temperature, the solvent was removed in vacuo. The residue was suspended in 3 N sulfuric acid and the reaction mixture was heated at reflux for 2 h. Upon cooling to room temperature, the salicylaldehyde by-product was removed by extraction with diethyl ether (1×10 mL). The clear aqueous layer was neutralized with 5% sodium hydroxide solution to precipitate out the diamine product (pH>9). Crude 1-(4-chloro-phenyl)-2-(4-nitro-phenyl)-ethane-1,2-diamine (4.61 g) was collected by filtration, washed with water, and dried under vacuum overnight.

Di-t-butyldicarbonate (6.77 g, 31 mmol) was added to a solution of crude 1-(4-chloro-phenyl)-2-(4-nitro-phenyl)-ethane-1,2-diamine (2.92 g) in acetonitrile (100 mL) in an ice-bath. Dimethylaminopyridine (122 mg, 1 mmol) was added and the ice-bath was removed. After 1 h, more dimethylaminopyridine (122 mg, 1 mmol) was added. After a few minutes, the mixture was warmed up to 50° C. over 10 min. Evaporation of the solvents and reversed phase HPLC purification of the crude mixture gave 4-(4-chloro-phenyl)-5-(4-nitro-phenyl)-2-oxo-cyclopentane-1,3-dicarboxylic acid di-tert-butyl ester (1.19 g).

A mixture of 4-(4-chloro-phenyl)-5-(4-nitro-phenyl)-2-oxo-cyclopentane-1,3-dicarboxylic acid di-tert-butyl ester (1.0 g, 2.0 mmol) in hydrobromic acid (4.37 mL, 48%) and acetic acid (3.21 mL) was heated at reflux overnight. After cooling to room temperature, water was added. The mixture was washed with diethyl ether and then basified with 10 N NaOH. The aqueous layers were extracted with methylene chloride. The organic extracts were washed with brine, dried over magnesium sulfate and evaporated to give 1-(4-chloro-phenyl)-2-(4-nitro-phenyl)-ethane-1,2-diamine (464 mg, 80%).

To a solution of 1-(4-chloro-phenyl)-2-(4-nitro-phenyl)-ethane-1,2-diamine (200 mg, 0.685 mmol) and ethyl 4-methoxy-benzimidate hydrochloride (148 mg, 0.686 mmol) in ethanol (5 mL) was added triethylamine (0.11 mL, 0.79 mmol). The reaction mixture was heated at reflux for 12 h. The solvent was removed to give a clear oil. It was then taken in methylene chloride (2 mL) and aqueous sodium carbonate. The product was extracted with methylene chloride (2×20 mL). The organic layers were washed with brine (1×5 mL), dried (Na$_2$SO$_4$) and concentrated. Purification of the crude residue by Biotage flash chromatography eluting with 70% ethyl acetate in hexanes gave 4-(4-chloro-phenyl)-2-(4-methoxy-phenyl)-5-(4-nitro-phenyl)-4,5-dihydro-1H-imidazole (103 mg, 37%).

Isobutyryl chloride (32 μL, 0.30 mmol) was added to a solution of triethylamine (71 μL, 0.51 mmol) and 4-(4-chloro-phenyl)-2-(4-methoxy-phenyl)-5-(4-nitro-phenyl)-4,5-dihydro-1H-imidazole (103 mg, 0.25 mmol). The reaction mixture was stirred at room temperature for 2 h and it was then diluted with methylene chloride and aqueous sodium. The organic layer was washed with water and brine, and dried over sodium sulfate. The solvents were remove under reduced pressure and chromatography of the residue over silica gel using 10–40% ethyl acetate in hexanes gave 2 products:

a) 1-[5-(4-Chloro-phenyl)-2-(4-methoxy-phenyl)-4-(4-nitro-phenyl)-4,5-dihydro-imidazol-1-yl]-2-methyl-propan-1-one (48 mg, 40%). HR-MS (ES, m/z) calculated for $C_{26}H_{25}N_3O_4Cl[(M+H)^+]$478.1528, observed 478.1533

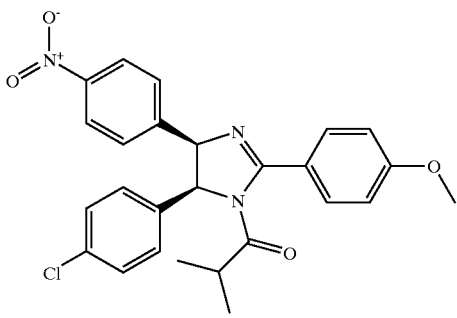

b) 1-[4-(4-chloro-phenyl)-2-(4-methoxy-phenyl)-5-(4-nitro-phenyl)-4,5-dihydro-imidazol-1-yl]-2-methyl-propan-1-one (31 mg, 26%). HR-MS (ES, m/z) calculated for $C_{26}H_{25}N_3O_4Cl[(M+H)^+]$478.1528, observed 478.1533.

EXAMPLE 6

1-[4,5-Bis-(4-chloro-phenyl)-2-(2-isopropoxy-phenyl)-4,5-dihydro-imidazol-1-yl]-2-methyl-propan-1-one

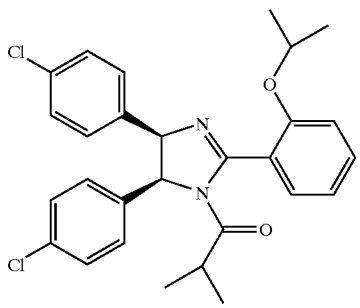

A mixture of 2-cyanophenol (5.0 g, 42 mmol), cesium carbonate (27.1 g, 82.9 mmol) and 2-iodopropane (7.63 mL, 76 mmol) in acetone (80 mL) was heated at 60° C. with vigorous stirring. After 45 min, the gray brown mixture was decanted and the acetone layer was concentrated in vacuo. Water was added to dissolve the solid, and the mixture was extracted with diethyl ether (3×200 mL). The organic layers were washed with water, 1 N ammonium hydroxide and brine, and dried over anhydrous sodium sulfate. The solids were then filtered off, and the filtrate was concentrated in vacuo. Purification of the crude residue by flash chromatography (Biotage system, KP-Sil™ 32–63 μm, 60 Å silica gel) eluting with 5% ethyl acetate in hexanes yielded 2-isopropoxy-benzonitrile (6.6 g, 97%) as a colorless liquid.

Hydrogen chloride gas was passed through a solution of 2-isopropoxy-benzonitrile (6.6 g, 40.9 mmol) in anhydrous ethanol (75 mL) at 0° C. in a pressure tube. After 30 min, hydrogen chloride gas was stopped. The reaction vessel was sealed and stirred at room temperature for 3 d. The pressure was released only after the tube has been cooled to 0° C. The solvent was removed to give a pale yellow oil (10.1 g). It was triturated in diethyl ether (100 mL) to afford a white solid. Ethyl 2-isopropoxy-benzimidate hydrochloride (9.17 g, 92%) was collected by filtration, washed with diethyl ether (3×25 mL), and dried in vacuo. It was used without further purification.

To a solution of triethylamine (0.88 mL, 6.26 mmol) in ethanol (3.5 mL) were added meso-1,2-bis-(4-chloro-phenyl)-ethane-1,2-diamine (0.80 g, 2.85 mmol, prepared according to the procedure described by Vogtle, F.; Goldschmitt, E. *Chem. Ber.* 1976, 109, 1–40) and ethyl 2-isopropoxy-benzimidate hydrochloride (0.86 g, 3.52 mmol) . The reaction mixture was refluxed overnight. After cooled to room temperature, the reaction mixture was diluted with methylene chloride washed with with1 N HCl and 5% aqueous sodium bicarbonate. The organic layer was washed with brine and dried over anhydrous sodium sulfate. Evaporation of the solvents and chromatography of the residue over silica gel using 2% methanol in methylene chloride gave 4,5-bis-(4-chloro-phenyl)-2-(2-isopropoxy-phenyl)-4,5-dihydro-1H-imidazole (0.86 g, 71%).

Isobutyryl chloride (8.1 μL, 0.077 mmol) was added to a solution of triethylamine (10.8 μL, 0.077 mmol) and 4,5-bis-(4-chloro-phenyl)-2-(2-isopropoxy-phenyl)-4,5-dihydro-1H-imidazole (30 mg, 0.071 mmol) in methylene chloride (3 mL). The reaction mixture was stirred at room temperature for 3 h. It was then diluted with methylene chloride and washed with water and brine, and dried over sodium sulfate. The solvents were remove under reduced pressure and chromotography of the residue over silica gel using 25% ethyl acetate in hexanes gave 1-[4,5-bis-(4-chloro-phenyl)-2-(2-isopropoxy-phenyl)-4,5-dihydro-imidazol-1-yl]-2-methyl-propan-1-one. HR-MS (ES, m/z) calculated for $C_{28}H_{29}N_2O_2Cl_2[(M+H)^+]$495.1601, observed 495.1606.

EXAMPLE 7

[4,5-Bis-(4-chloro-phenyl)-2-(2-isopropoxy-phenyl)-4,5-dihydro-imidazol-1-yl]-(4-pyrrolidin-1-yl-piperidin-1-yl)-methanone

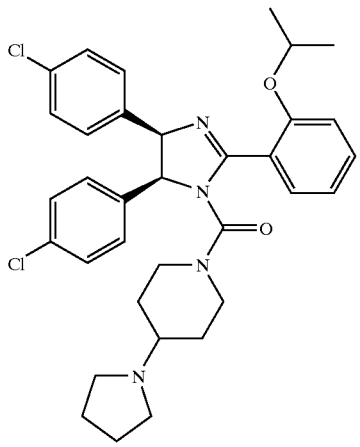

Phosgene (2.95 mL, 5.69 mmol, 1.93 M in toluene) was added dropwise to a cooled mixture of triethylamine (1.3 mL, 9.4 mmol) and 4,5-bis-(4-chloro-phenyl)-2-(2-isopropoxy-phenyl)-4,5-dihydro-1H-imidazole (0.80 g, 1.88 mmol, example 6) in methylene chloride (15 mL) at 0° C. The reaction mixture was stirred for 30 min at 0° C. and evaporated. The residue was kept under high vacuum for 30 min. Chromatography of the residue over silica gel using 60–80% methylene chloride in hexanes gave 4,5-bis-(4-chloro-phenyl)-2-(2-isopropoxy-phenyl)-4,5-dihydro-imidazole-1-carbonyl chloride (0.71 g, 77%)

4,5-Bis-(4-chloro-phenyl)-2-(2-isopropoxy-phenyl)-4,5-dihydro-imidazole-1-carbonyl chloride (200 mg, 0.41 mmol) was added a solution of triethylamine (0.23 mL, 1.64 mmol) and 4-(1-pyrrolidinyl)-piperidine (0.11 g, 0.70 mmol) in methylene chloride (8 mL) at 0° C. over 15 min. After 30 min, the reaction was worked up with water. The mixture was extracted with methylene chloride and washed with water and brine. The organic extracts were dried over sodium sulfate and evaporated. Chromatography of the residue over silica gel using 1–2% methanol in methylene chloride gave [4,5-bis-(4-chloro-phenyl)-2-(2-isopropoxy-phenyl)-4,5-dihydro-imidazol-1-yl]-(4-pyrrolidin-1-yl-piperidin-1-yl)-methanone (0.18 g, 72%) as an off-white foam. HR-MS (ES, m/z) calculated for $C_{34}H_{39}N_4O_2Cl_2$ [(M+H)$^+$]605.2445, observed 605.2448

EXAMPLE 8

In a similar manner as described in examples 6 and 7, the following compounds were prepared.

a) [4,5-Bis-(4-chloro-phenyl)-2-(2-isopropoxy-phenyl)-4,5-dihydro-imidazol-1-yl]-piperazin-1-yl-methanone. HR-MS (ES, m/z) calculated for $C_{29}H_3N_4O_2Cl_2$[(M+H)$^+$]537.1819, observed 537.1828

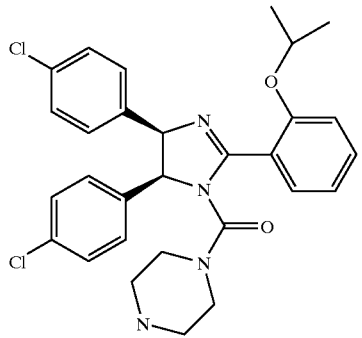

b) [4,5-Bis-(4-chloro-phenyl)-2-(2-isopropoxy-phenyl)-4,5-dihydro-imidazol-1-yl]-(4-dimethylamino-piperidin-1-yl)-methanone. HR-MS (ES, m/z) calculated for $C_{32}H_{37}N_4O_2Cl_2$[(M+H)$^+$]579.2288, observed 579.2293.

c) [1,4']Bipiperidinyl-1'-yl-[4,5-bis-(4-chloro-phenyl)-2-(2-isopropoxy-phenyl)-4,5-dihydro-imidazol-1-yl]-methanone. HR-MS (ES, m/z) calculated for $C_{35}H_{41}N_4O_2Cl_2$[(M+H)$^+$]619.2601, observed 619.2606.

d) [4,5-Bis-(4-chloro-phenyl)-2-(2-isopropoxy-phenyl)-4,5-dihydro-imidazol-1-yl]-[4-(2hydroxy-ethyl)-piperidin-1-yl)-methanone. HR-MS (ES, m/z) calculated for $C_{31}H_{35}N_4O_3Cl_2$[(M+H)$^+$]581.2081, observed 581.2082.

e) {4,5-Bis-(4-chloro-phenyl)-2-[2-(2-methyl-butoxy)-phenyl]-4,5-dihydro-imidazol-1-yl}-piperidin-1-yl)-methanone. HR-MS (ES, m/z) calculated for $C_{31}H_{35}N_4O_2Cl_2$[(M+H)$^+$]565.2132, observed 565.2140.

f) [4,5-Bis-(4-chloro-phenyl)-2-(2-pentyloxy-phenyl)-4,5-dihydro-imidazol-1-yl]-piperazin-1-yl]-piperidin-1-yl)-methanone. HR-MS (ES, m/z) calculated for $C_{31}H_{35}N_4O_2Cl_2$[(M+H)$^+$]565.2132, observed 565.2138.

g) [4,5-Bis-(4-chloro-phenyl)-2-(3-ethoxy-phenyl)-4,5-dihydro-imidazol-1-yl]-piperazin-1-yl-methanone, trifluoroacetic acid salt. HR-MS (ES, m/z) calculated for $C_{28}H_{29}N_4O_2Cl_2$[(M+H)$^+$]523.1662, observed 523.1666.

h) [4,5-Bis-(4-chloro-phenyl)-2-(3-isopropoxy-phenyl)-4,5-dihydro-imidazol-1-yl]-piperazin-1-yl-methanone, trifluoroacetic acid salt. HR-MS (ES, m/z) calculated for $C_{29}H_{31}N_4O_2Cl_2$[(M+H)$^+$]537.1819, observed 537.1824.

i) 1-{4-[4,5-Bis-(4-bromo-phenyl)-2-(2-ethoxy-phenyl)-4,5-dihydro-imidazole-1-carbonyl]-piperazin-1-yl}-ethanone. HR-MS (ES, m/z) calculated for $C_{30}H_{31}N_4O_3Br_2$[(M+H)$^+$]653.0758, observed 653.0771.

j) [4,5-Bis-(4-bromo-phenyl)-2-(2-ethoxy-phenyl)-4,5-dihydro-imidazol-1-yl]-[4-(2-hydroxy-ethyl)-piperazin-1-yl]-methanone. HR-MS (ES, m/z) calculated for $C_{30}H_{33}N_4O_3Br_2$[(M+H)$^+$]655.0914, observed 655.0928.

k) 1-{4-[4,5-Bis-(4-bromo-phenyl)-2-(2-isopropoxy-phenyl)-4,5-dihydro-imidazole-1-carbonyl]-piperazin-1-yl}-ethanone. HR-MS (ES, m/z) calculated for $C_{31}H_{33}N_4O_3Br_2$[(M+H)$^+$]667.0914, observed 667.0920.

l) [4,5-Bis-(4-bromo-phenyl)-2-(2-isopropoxy-phenyl)-4,5-dihydro-imidazol-1-yl]-[4-(2-hydroxy-ethyl)-piperazin-1-yl]-methanone. HR-MS (ES, m/z) calculated for $C_{31}H_{35}N_4O_3Br_2$[(M+H)$^+$]669.1071, observed 669.1069.

EXAMPLE 9

[4,5-Bis-(4-chloro-phenyl)-2-(2-isopropoxy-4-methoxy-phenyl)-4,5-dihydro-imidazol-1-yl]-[4-(2-hydroxy-ethyl)-piperazin-1-yl]-methanone hydrochloride

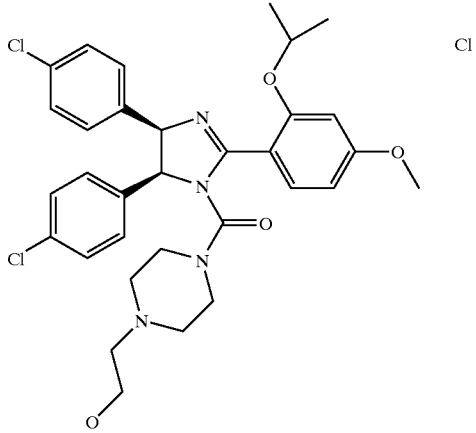

A mixture of 2-hydroxy-4-methoxybenzaldehyde (25.0 g, 164 mmol), sodium acetate (26.4 g, 322 mmol), nitroethane (23 g, 307 mmol) in acetic acid (45 mL) was heated at reflux for 6 h. The mixture was then cooled to room temperature and poured onto ice water. The solids were filtered off, washed with water and dried. Recrystallization of the crude solid in ethyl acetate gave 2-hydroxy-4-methoxy-benzonitrile as a brown solid (15.9 g, 65%).

Cesium carbonate (51.5 g, 158 mmol) was added to a solution of 2-hydroxy-4-methoxybenzonitrile (11.8 g, 79 mmol) in acetone (100 mL). 2-Iodopropane (12.5 mL, 125 mmol) was added. The mixture was heated at reflux for 3 h. Water was added and the mixture was extracted with diethyl ether (4×100 mL). The combined organic extracts were washed with diluted ammonium hydroxide, brine and dried (MgSO$_4$). Evaporation of the solvents and chromatography of the residue over silica gel using 5% diethyl ether in hexanes gave 2-isopropoxy-4-methoxybenzonitrile (13.2 g, 87%).

Hydrogen chloride gas was passed through a solution of 2-isopropoxy-4-methoxybenzonitrile (13.2 g, 69 mmol) in absolute ethanol (200 mL) in a pressure tube for 1 h at −10° C. The tube was sealed and stirred at room temperature for 7 d. The tube was cooled to −10° C. and more ethanol (100 mL) was added. Hydrogen chloride gas was passed through it for additional 30 min at −10° C. The tube was resealed and stirred at room temperature for 7 d. Evaporation of the solvents and trituration of the residue in diethyl ether gave ethyl 2-isopropoxy-4-methoxy-benzimidate hydrochloride as a white solid (17.5 g, 99%). It was used without further purification.

A mixture of ethyl 2-isopropoxy-4-methoxy-benzimidate hydrochloride (8.21 g, 30 mmol), meso-1,2-bis-(4-chloro-phenyl)-ethane-1,2-diamine (7.59 g, 27 mmol, prepared according to the procedure described by Vogtle, F.; Goldschmitt, E. *Chem. Ber.* 1976, 109, 1–40) and triethylamine (8.35 mL, 60 mmol) in ethanol (200 mL) was heated at reflux for 24 h. Additional ethyl 2-isopropoxy-4-methoxy-benzimidate hydrochloride (1.64 g, 6 mmol) was added and the reaction mixture was heated at reflux for another 24 h. Aqueous sodium bicarbonate was added and it was extracted with methylene chloride (3×). The combined organic extracts were washed with water and brine, and dried over sodium sulfate. Chromatography of the residue over silica gel using 0.5–2% methanol in methylene chloride followed by recrystallization using diethyl ether in pentane gave 4,5-bis-(4-chloro-phenyl)-2-(2-isopropoxy-4-methoxy-phenyl)-4,5-dihydro-1H-imidazole (9 g, 73%).

Phosgene (12 mL, 23 mmol, 1.93 M in toluene) was added dropwise to a mixture of triethylamine (3.75 mL, 26.9 mmol) and 4,5-bis-(4-chloro-phenyl)-2-(2-isopropoxy-4-methoxy-phenyl)-4,5-dihydro-1H-imidazole (3.50 g, 7.69 mmol) in methylene chloride (80 mL) at 0° C. The reaction mixture was stirred for 30 min at 0° C. and evaporated. The residue was kept under high vacuum for 30 min. Methylene chloride (50 mL) was added to the residue and the solution was added dropwise to a solution of 2-piperazin-1-yl-ethanol (10 g) in methylene chloride (200 mL) at 0° C. over 15 min. After 30 min, the reaction was worked up with water. The mixture was extracted with methylene chloride and washed with water and brine. The organic extracts were dried over sodium sulfate and evaporated. Chromatography of the residue over silica gel using 1–2% methanol in methylene chloride gave [4,5-bis-(4-chloro-phenyl)-2-(2-isopropoxy-4-methoxy-phenyl)-4,5-dihydro-1H-imidazole-1-yl]-[4-(2-hydroxy-ethyl)-piperazin-1-yl]-methanone as a light yellow foam (4.07 g, 87%).

[4,5-Bis-(4-chloro-phenyl)-2-(2-isopropoxy-4-methoxy-phenyl)-4,5-dihydro-imidazol-1-yl]-[4-(2-hydroxy-ethyl)-piperazin-1-yl]-methanone (2.20 g, 3.60 mmol) was dissolved in dilute hydrochloric acid (0.23 N, 20 mL). The light yellow solution was filtered and lyophilized to give [4,5-bis-(4-chloro-phenyl)-2-(2-isopropoxy-4-methoxy-phenyl)-4,5-dihydro-imidazole-1-yl]-[4-(2-hydroxy-ethyl)-piperazin-1-yl]-methanone hydrochloride as a off-white powder (2.26 g, 97%). HR-MS (ES, m/z) calculated for $C_{32}H_{37}N_4O_4Cl_2[(M+H)^+]$611.2187, observed 611.2195.

EXAMPLE 10

In a similar manner as described in example 9, the following compounds were prepared.

a) [4,5-Bis-(4-chloro-phenyl)-2-(2-ethoxy-4-methoxy-phenyl)-4,5-dihydro-imidazol-1-yl]-(4-methanesulfonyl-piperazin-1-yl)-methanone. HR-MS (ES, m/z) calculated for $C_{30}H_{33}N_4O_5SCl_2[(M+H)^+]$ 631.1543, observed 631.1549

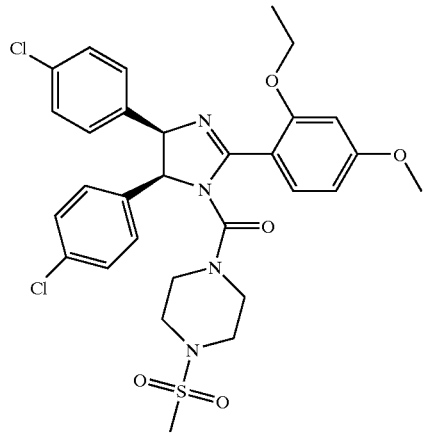

b) [4,5-Bis-(4-chloro-phenyl)-2-(2-ethoxy-4-methoxy-phenyl)-4,5-dihydro-imidazol-1-yl]-[4-(2-hydroxy-ethyl)-piperazin-1-yl]-methanone. HR-MS (ES, m/z) calculated for $C_{31}H_{35}N_4O_4Cl_2[(M+H)^+]$597.2030, observed 597.2038.

c) [4,5-Bis-(4-chloro-phenyl)-2-(2-ethoxy-4-methoxy-phenyl)-4,5-dihydro-imidazol-1-yl]-morpholin-4-yl-methanone. HR-MS (ES, m/z) calculated for $C_{29}H_{30}N_3O_4Cl_2[(M+H)^+]$554.1608, observed 554.1614 d) [4,5-Bis-(4-chloro-phenyl)-2-(2-ethoxy-4-methoxy-phenyl)-4,5-dihydro-imidazol-1-yl]-(4-methyl-piperazin-1-yl)-methanone. HR-MS (ES, m/z) calculated for $C_{30}H_{33}N_4O_3Cl_2[(M+H)^+]$567.1924, observed 567.1929.

e) 1-{4-[4,5-Bis-(4-chloro-phenyl)-2-(2-ethoxy-4-methoxy-phenyl)-4,5-dihydro-imidazole-1-carbonyl]-piperazin-1-yl}-ethanone. HR-MS (ES, m/z) calculated for $C_{31}H_{33}N_4O_4Cl_2[(M+H)^+]$595.1874, observed 595.1882.

f) 4-[4,5-Bis-(4-chloro-phenyl)-2-(2-ethoxy-4-methoxy-phenyl)-4,5-dihydro-imidazole-1-carbonyl]-piperazin-2-one. HR-MS (ES, m/z) calculated for $C_{29}H_{29}N_4O_4Cl_2[(M+H)^+]$567.1561, observed 567.1571.

g) [4,5-Bis-(4-chloro-phenyl)-2-(2-isopropoxy-4-methoxy-phenyl)-4,5-dihydro-imidazol-1-yl]-piperazin-1-yl-methanone. HR-MS (ES, m/z) calculated for $C_{30}H_{33}N_4O_3Cl_2[(M+H)^+]$567.1924, observed 567.1927.

h) 1-{4-[4,5-Bis-(4-chloro-phenyl)-2-(2-isopropoxy-4-methoxy-phenyl)-4,5-dihydro-imidazole-1-carbonyl]-piperazin-1-yl}-ethanone. HR-MS (ES, m/z) calculated for $C_{32}H_{35}N_4O_4Cl_2[(M+H)^+]$609.2030, observed 609.2036.

i) [4,5-Bis-(4-chloro-phenyl)-2-(2-isopropoxy-4-methoxy-phenyl)-4,5-dihydro-imidazol-1-yl]-(4-methanesulfonyl-piperazin-1-yl)-methanone was prepared by sulfonylation of [4,5-bis-(4-chloro-phenyl)-2-(2-isopropoxy-4-methoxy-phenyl)-4,5-dihydro-imidazol-1-yl]-piperazin-1-yl-methanone (example 10 g). HR-MS (ES, m/z) calculated for $C_{31}H_{35}N_4O_5SCl_2$ $[(M+H)^+]$645.1700, observed 645.1710.

j) [4,5-Bis-(4-chloro-phenyl)-2-(2-isopropoxy-4-methoxy-phenyl)-4,5-dihydro-imidazol-1-yl]-(2,5- dimethyl-piperazin-1-yl-methanone. HR-MS (ES, m/z) calculated for $C_{32}H_{37}N_4O_3Cl_2[(M+H)^+]$595.2237, observed 595.2240.

k) 4,5-Bis-(4-chloro-phenyl)-2-(2-isopropoxy-4-methoxy-phenyl)-4,5-dihydro-imidazole-1-carboxylic acid bis-(2-hydroxy-ethyl)-amide. HR-MS (ES, m/z) calculated for $C_{30}H_{34}N_3O_5Cl_2[(M+H)^+]$586.1870, observed 586.1878.

l) [4,5-Bis-(4-chloro-phenyl)-2-(2-isopropoxy-4-methoxy-phenyl)-4,5-dihydro-imidazol-1-yl]-(4-ethyl-piperazin-1-yl)-methanone. HR-MS (ES, m/z) calculated for $C_{32}H_{37}N_4O_3Cl_2[(M+H)^+]$595.2237, observed 595.2241.

m) [1,4']Bipiperidinyl-1'-yl-[4,5-bis-(4-chloro-phenyl)-2-(2-isopropoxy-4-methoxy-phenyl)-4,5--dihydro-imidazole-1-yl]-methanone. HR-MS (ES, m/z) calculated for $C_{36}H_{43}N_4O_3Cl_2[(M+H)^+]$649.2707, observed 649.2712.

n) [4,5-Bis-(4-chloro-phenyl)-2-(2-isopropoxy-4-methoxy-phenyl)-4,5-dihydro-imidazol-1-yl]-(4-pyrrolidin-1-yl-piperidin-1-yl)-methanone. HR-MS (ES, m/z) calculated for $C_{35}H_{41}N_4O_3Cl_2[(M+H)^+]$ 635.2550, observed 635.2559.

o) [4,5-Bis-(4-chloro-phenyl)-2-(2-isopropoxy-4-methoxy-phenyl)-4,5-dihydro-imidazol-1-yl]-(4-dimethylamino-piperidin-1-yl)-methanone. HR-MS (ES, m/z) calculated for $C_{33}H_{39}N_4O_3Cl_2[(M+H)^+]$ 609.2394, observed 609.2395.

p) [4,5-Bis-(4-chloro-phenyl)-2-(2-isopropoxy-4-methoxy-phenyl)-4,5-dihydro-imidazol-1-yl]-morpholin-4-methanone. HR-MS (ES, m/z) calculated for $C_{30}H_{32}N_3O_4Cl_2[(M+H)^+]$568.1765, observed 568.1768.

q) [4,5-Bis-(4-chloro-phenyl)-2-(2-isopropoxy-4-methoxy-phenyl)-4,5-dihydro-imidazol-1-yl]-(4-isopropyl-piperidin-1-yl)-methanone. HR-MS (ES, m/z) calculated for $C_{33}H_{39}N_4O_3Cl_2[(M+H)^+]$ 609.2394, observed 609.2395. The N-isopropyl piperazine used in the synthesis of above compound was prepared according to the procedure described in Renau, Thomas E.; Sanchez, Joseph P. et al. *J. Med. Chem.* 1996, 39, 729–35.

r) 4-[4,5-Bis-(4-chloro-phenyl)-2-(2-isopropoxy-4-methoxy-phenyl)-4,5-dihydro-imidazole-1-carbonyl]-piperidin-2-one. HR-MS (ES, m/z) calculated for $C_{30}H_{31}N_4O_4Cl_2[(M+H)^+]$581.1717, observed 581.1723.

s) [4,5-Bis-(4-chloro-phenyl)-2-(2-isopropoxy-4-methoxy-phenyl)-4,5-dihydro-imidazol-1-yl]-(4-hydroxymethyl-piperidin-1-yl)-methanone. HR-MS (ES, m/z) calculated for $C_{32}H_{36}N_3O_4Cl_2[(M+H)^+]$ 596.2078, observed 596.2081.

t) [4,5-Bis-(4-chloro-phenyl)-2-(2-isopropoxy-4-methoxy-phenyl)-4,5-dihydro-imidazol-1-yl]-[4-(2-hydroxy-ethyl)-piperidin-1-yl]-methanone. HR-MS (ES, m/z) calculated for $C_{33}H_{38}N_3O_4Cl_2[(M+H)^+]$ 610.2234, observed 610.2236.

u) [4,5-Bis-(4-chloro-phenyl)-2-(2-isopropoxy-4-methoxy-phenyl)-4,5-dihydro-imidazol-1-yl]-(3-methyl-piperidin-1-yl)-methanone. HR-MS (ES, m/z) calculated for $C_{31}H_{35}N_4O_3Cl_2[(M+H)^+]$581.2081, observed 581.2081.

v) 1-{4-[4,5-Bis-(4-chloro-phenyl)-2-(2-isopropoxy-4-methoxy-phenyl)-4,5-dihydro-imidazole-1-carbonyl]-2-methyl-piperidin-1-yl}-ethanone. HR-MS (ES, m/z) calculated for $C_{33}H_{37}N_4O_4Cl_2[(M+H)^+]$623.2187, observed 623.2190.

w) [4,5-Bis-(4-chloro-phenyl)-2-(2-isopropoxy-4-methoxy-phenyl)-4,5-dihydro-imidazol-1-yl]-(4-methanesulfonyl-3-methyl-piperazin-1-yl)-methanone was prepared by sulfonylation of [4,5-bis-(4-chloro-phenyl)-2-(2-isopropoxy-4-methoxy-phenyl)-4,5-dihydro-imidazol-1-yl]-(3-methyl-piperidin-1-yl)-methanone (example 10u). HR-MS (ES, m/z) calculated for $C_{32}H_{37}N_4O_5SCl_2[(M+H)^+]$659.1856, observed 659.1856.

x) [4,5-Bis-(4-chloro-phenyl)-2-(2-isopropoxy-4-methoxy-phenyl)-4,5-dihydro-imidazol-1-yl]-(4-hydroxy-piperidin-1-yl)-methanone. HR-MS (ES, m/z) calculated for $C_{31}H_{34}N_3O_4Cl_2[(M+H)^+]$582.1921, observed 582.1926.

y) (4-Aminomethyl-piperidin-1-yl)-[4,5-bis-(4-chloro-phenyl)-2-(2-isopropoxy-4-methoxy-phenyl)-4,5-dihydro-imidazol-1-yl]-methanone. HR-MS (ES, m/z) calculated for $C_{32}H_{37}N_4O_3Cl_2[(M+H)^+]$595.2237, observed 595.2243.

z) [4,5-Bis-(4-bromo-phenyl)-2-(2-ethoxy-4-methoxy-phenyl)-4,5-dihydro-imidazol-1-yl]-[4-(2-hydroxy-ethyl)-piperazin-1-yl]methanone. HR-MS (ES, m/z) calculated for $C_{31}H_{35}N_4O_4Br_2[(M+H)^+]$685.1020, observed 685.1031.

aa) [4,5-Bis-(4-bromo-phenyl)-2-(2-ethoxy-4-methoxy-phenyl)-4,5-dihydro-imidazol-1-yl]-piperazin-1-yl-methanone. HR-MS (ES, m/z) calculated for $C_{29}H_{31}N_4O_3Br_2[(M+H)^+]$641.0758, observed 641.0762.

bb) [4,5-Bis-(4-bromo-phenyl)-2-(2-ethoxy-4-methoxy-phenyl)-4,5-dihydro-imidazol-1-yl]-(4-methanesulfonyl-piperazin-1-yl)-methanone was prepared by sulfonylation of [4,5-bis-(4-bromo-phenyl)-2-(2-ethoxy-4-methoxy-phenyl)-4,5-dihydro-imidazol-1-yl]-piperazin-1-yl-methanone (example 10aa) using the method known in the art. HR-MS (ES, m/z) calculated for $C_{30}H_{33}N_4O_5SBr_2[(M+H)^+]$719.0533, observed 719.0540.

cc) 1-{4-[4,5-Bis-(4-bromo-phenyl)-2-(2-ethoxy-4-methoxy-phenyl)-4,5-dihydro-imidazole-1-carbonyl]-piperazin-1-yl}-ethanone. HR-MS (ES, m/z) calculated for $C_{31}H_{33}N_4O_4Br_2[(M+H)^+]$683.0863, observed 683.0866.

dd) [4,5-Bis-(4-bromo-phenyl)-2-(2-ethoxy-4-methoxy-phenyl)-4,5-dihydro-imidazol-1-yl]-(4-methyl-piperazin-1-yl)-methanone. HR-MS (ES, m/z) calculated for $C_{30}H_{33}N_4O_3Br_2[(M+H)^+]$655.0914, observed 655.0917.

ee) 4-[4,5-Bis-(4-bromo-phenyl)-2-(2-ethoxy-4-methoxy-phenyl)-4,5-dihydro-imidazole-1-carbonyl]-piperazin-1-carbaldehyde. HR-MS (ES, m/z) calculated for $C_{30}H_{31}N_4O_4Br_2[(M+H)^+]$669.0707, observed 669.0713.

ff) [4,5-Bis-(4-bromo-phenyl)-2-(2-ethoxy-4-methoxy-phenyl)-4,5-dihydro-imidazol-1-yl]-(4-pyrrolidin-1-yl-piperidin-1-yl)-methanone. HR-MS (ES, m/z) calculated for $C_{34}H_{39}N_4O_3Br_2[(M+H)^+]$709.1384, observed 709.1401.

gg) [4,5-Bis-(4-bromo-phenyl)-2-(2-ethoxy-4-methoxy-phenyl)-4,5-dihydro-imidazol-1-yl]-(4-dimethylamino-piperidin-1-yl)-methanone. HR-MS (ES, m/z) calculated for $C_{32}H_{37}N_4O_3Br_2[(M+H)^+]$683.1227, observed 683.1250.

hh) [4,5-Bis-(4-bromo-phenyl)-2-(2-ethoxy-4-methoxy-phenyl)-4,5-dihydro-imidazol-1-yl]-(4-isopropyl-piperidin-1-yl)-methanone. HR-MS (ES, m/z) calculated for $C_{32}H_{37}N_4O_3Br_2[(M+H)^+]$683.1227, observed 683.1231.

ii) 4-[4,5-Bis-(4-bromo-phenyl)-2-(2-ethoxy-4-methoxy-phenyl)-4,5-dihydro-imidazole-1-carbonyl]piperazin-2-one. HR-MS (ES, m/z) calculated for $C_{29}H_{29}N_4O_4Br_2[(M+H)^+]$655.0550, observed 655.0557.

jj) [4,5-Bis-(4-bromo-phenyl)-2-(2-isopropoxy-4-methoxy-phenyl)-4,5-dihydro-imidazol-1-yl]-piperazin-1-yl-methanone. HR-MS (ES, m/z) calculated for $C_{30}H_{33}N_4O_3Br_2[(M+H)^+]$655.0914, observed 655.0918 kk) 1-{4-[4,5-Bis-(4-bromo-phenyl)-2-(2-isopropoxy-4-methoxy-phenyl)-4,5-dihydro-imidazol-1-carbonyl]-piperazin-1-yl}-ethanone. HR-MS (ES, m/z) calculated for $C_{32}H_{35}N_4O_4Br_2[(M+H)^+]$697.1020 observed 697.1028.

ll) [4,5-Bis-(4-bromo-phenyl)-2-(2-isopropoxy-4-methoxy-phenyl)-4,5-dihydro-imidazol-1-yl]-(4-methanesulfonyl-piperazin-1-yl)-methanone was prepared by sulfonylation of [4,5-bis-(4-bromo-phenyl)-2-(2-isopropoxy-4-methoxy-phenyl)-4,5-dihydro-imidazol-1-yl]-piperazin-1-yl-methanone (example 10jj) using the method known in the art. HR-MS (ES, m/z) calculated for $C_{31}H_{35}N_4O_5SBr_2[(M+H)^+]$ 733.0690, observed 733.0696.

mm) [4,5-Bis-(4-bromo-phenyl)-2-(2-isopropoxy-4-methoxy-phenyl)-4,5-dihydro-imidazol-1-yl]-(4-methyl-piperazin-1-yl)-methanone. HR-MS (ES, m/z) calculated for $C_{31}H_{35}N_4O_3Br_2[(M+H)^+]$669.1071, observed 669.1078.

nn) [4,5-Bis-(4-bromo-phenyl)-2-(2-isopropoxy-4-methoxy-phenyl)-4,5-dihydro-imidazol-1-yl]-morpholin-4-yl-methanone. HR-MS (ES, m/z) calculated for $C_{30}H_{32}N_{30}O_4Br_2[(M+H)^+]$656.0754, observed 656.0762.

oo) [1,4']Bipiperidinyl-1'-yl-[4,5-bis-(4-bromo-phenyl)-2-(2-isopropoxy-4-methoxy-phenyl)-4,5-dihydro-imidazol-1-yl]-methanone. HR-MS (ES, m/z) calculated for $C_{36}H_{43}N_4O_3Br_2[(M+H)^+]$737.1697, observed 737.1707.

pp) [4,5-Bis-(4-bromo-phenyl)-2-(2-isopropoxy-4-methoxy-phenyl)-4,5-dihydro-imidazol-1-yl]-(4-ethyl-piperazin-1-yl)-methanone. HR-MS (ES, m/z) calculated for $C_{32}H_{37}N_4O_3Br_2[(M+H)^+]$683.1227, observed 683.1232.

qq) 4-[4,5-Bis-(4-bromo-phenyl)-2-(2-isopropoxy-4-methoxy-phenyl)-4,5-dihydro-imidazole-1-carbonyl]-piperazin-2-one. HR-MS (ES, m/z) calculated for $C_{30}H_{31}N_4O_4Br_2[(M+H)^+]$669.0707, observed 669.0718.

rr) [4,5-Bis-(4-cyano-phenyl)-2-(2-isopropoxy-4-methoxy-phenyl)-4,5-dihydro-imidazol-1-yl]-piperazin-1-yl-methanone. HR-MS (ES, m/z) calculated for $C_{32}H_{33}N_6O_3[(M+H)^+]$549.2609, observed 549.2614 ss) 1-(4-{4,5-Bis-(4-chloro-phenyl)-2-[4-methoxy-2-(2-methoxy-ethoxy)-phenyl]-4,5-dihydro-imidazole-1-carbonyl}-piperazin-2-ethanone. HR-MS (ES, m/z) calculated for $C_{32}H_{35}N_4O_5Cl_2[(M+H)^+]$625.1979, observed 625.1987.

tt) 1-(4-{4,5-Bis-(4-chloro-phenyl)-2-[2-(2-fluoro-ethoxy)-4-methoxy-phenyl]-4,5-dihydro-imidazole-1-carbonyl}-piperazin-1-yl)-ethanone. HR-MS (ES, m/z) calculated for $C_{31}H_{32}N_4O_4FCl_2[(M+H)^+]$613.1779, observed 613.1775.

uu) 4-{4,5-Bis-(4-chloro-phenyl)-2-[2-(2-fluoro-ethoxy)-4-methoxy-phenyl]-4,5-dihydro-imidazole-1-carbonyl}-piperazin-2-ethanone. HR-MS (ES, m/z) calculated for $C_{29}H_{28}N_4O_4FCl_2[(M+H)^+]$585.1466, observed 585.1475.

EXAMPLE 11

In a similar manner as described in example 9, the following compounds were prepared.

a) [4,5-Bis-(4-chloro-phenyl)-2-(2-ethoxy-4-methoxy-phenyl)-4,5-dihydro-imidazol-1-yl]-piperazin-1-yl-methanone hydrochloride. HR-MS (ES, m/z) calculated for $C_{29}H_{31}N_4O_3Cl_2[(M+H)^+]$553.1768, observed 553.1773

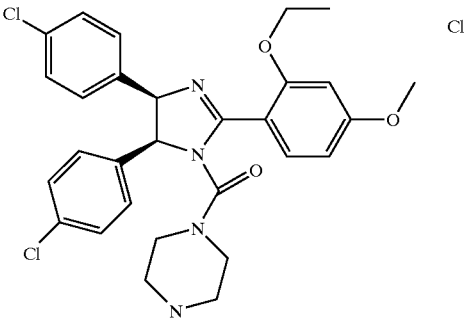

b) 4,5-Bis-(4-chloro-phenyl)-2-(2-ethoxy-4-methoxy-phenyl)-4,5-dihydro-imidazole-1-carboxylic acid methyl-(2-methylamino-ethyl)-amide, trifluoroacetic acid salt. HR-MS (ES, m/z) calculated for $C_{29}H_{33}N_4O_3Cl_2[(M+H)^+]$555.1924, observed 555.1929.

c) 4,5-Bis-(4-chloro-phenyl)-2-(2-ethoxy-4-methoxy-phenyl)-4,5-dihydro-imidazole-1-carboxylic acid (2-dimethylamino-ethyl)-methyl-amide, trifluoroacetic acid salt. HR-MS (ES, m/z) calculated for $C_{30}H_{35}N_4O_3Cl_2[(M+H)^+]$569.2081, observed 569.2085.

d) 4,5-Bis-(4-chloro-phenyl)-2-(2-ethoxy-4-methoxy-phenyl)-4,5-dihydro-imidazole-1-carboxylic acid (2-dimethylamino-ethyl)-amide, trifluoroacetic acid salt. HR-MS (ES, m/z) calculated for $C_{29}H_{33}N_4O_3Cl_2$[(M+H)^+]555.1924, observed 555.1940.

e) 4,5-Bis-(4-chloro-phenyl)-2-(2-ethoxy-4-methoxy-phenyl)-4,5-dihydro-imidazole-1-carboxylic acid (2-amino-ethyl)-amide, trifluoroacetic acid salt. HR-MS (m/z) calculated for $C_{27}H_{29}N_4O_3Cl_2[(M+H)^+]$ 527.1611, observed 527.1621.

f) [4,5-Bis-(4-chloro-phenyl)-2-(2-ethoxy-4-methoxy-phenyl)-4,5-dihydro-imidazol-1-yl]-(4-pyrrolidin-1-yl-piperazin-1-yl)-methanone hydrochloride. HR-MS (ES, m/z) calculated for $C_{34}H_{39}N_4O_3Cl_2[(M+H)^+]$ 621.2394, observed 621.2400.

g) [4,5-Bis-(4-chloro-phenyl)-2-(4-methoxy-2-propoxy-phenyl)-4,5-dihydro-imidazol-1-yl]-piperazin-1-yl-methanone, trifluoroacetic acid salt. HR-MS (ES, m/z) calculated trifluoroacetic acid salt. HR-MS (ES, m/z) calculated for $C_{30}H_{33}N_4O_3Cl_2[(M+H)^+]$567.1924, observed 567.1932.

h) [4,5-Bis-(4-chloro-phenyl)-2-(2-isopropoxy-4-methoxy-phenyl)-4,5-dihydro-imidazol-1-yl]-(4- methyl-piperazin-1-yl)-methanone hydrochloride. HR-MS (ES, m/z) calculated for $C_{31}H_{35}N_4O_3Cl_2[(M+H)^+]$581.2081, observed 581.2086.

i) 4,5-Bis-(4-chloro-phenyl)-2-(2-isopropoxy-4-methoxy-phenyl)-4,5-dihydro-imidazole-1-carboxylic acid (2-morpholin-4-yl-ethyl)-amide hydrochloride. HR-MS (ES, m/z) calculated for $C_{32}H_{37}N_4O_4Cl_2[(M+H)^+]$611.2187, observed 611.2197.

j) 4,5-Bis-(4-chloro-phenyl)-2-(2-isopropoxy-4-methoxy-phenyl)-4,5-dihydro-imidazole-1-carboxylic acid (2-piperazin-1-yl-ethyl)-amide hydrochloride. HR-MS (ES, m/z) calculated for $C_{32}H_{38}N_5O_3Cl_2[(M+H)+]$ 610.2346, observed 610.2348.

k) [4,5-Bis-(4-chloro-phenyl)-2-(2-isobutoxy-4-methoxy-phenyl)-4,5-dihydro-imidazol-1-yl]-piperazin-1-yl-methanone hydrochloride. HR-MS (ES, m/z) calculated for $C_{31}H_{35}N_4O_3Cl_2[(M+H)^+]$581.2081, observed 581.2081.

l) [4,5-Bis-(4-chloro-phenyl)-2-(2-isopropoxy-4-methoxy-phenyl)-4,5-dihydro-imidazol-1-yl]-(3-methyl-piperazin-1-yl)-methanone hydrochloride. HR-MS (ES, m/z) calculated for $C_{31}H_{35}N_4O_3Cl_2[(M+H)^+]$581.2081, observed 581.2084.

m) {4,5-Bis-(4-chloro-phenyl)-2-[4-methoxy-2-(2-methoxy-ethoxy)-phenyl]-4,5-dihydro-imidazol-1-yl}-piperazin-1-yl-methanone, trifluoroacetic acid salt. HR-MS (ES, m/z) calculated for $C_{30}H_{33}N_4O_4Cl_2[(M+H)^+]$583.1874, observed 583.1875.

n) {4,5-Bis-(4-chloro-phenyl)-2-[2-(2-fluoro-ethoxy)-4-methoxy-phenyl]-4,5-dihydro-imidazol-1-yl}-piperazin-1-yl-methanone. HR-MS (ES, m/z) calculated for $C_{29}H_{30}N_4O_3FCl_2[(M+H)^+]$571.1674, observed 571.1676.

o) {4,5-Bis-(4-chloro-phenyl)-2-[2-(2-fluoro-ethoxy)-4-methoxy-phenyl]-4,5-dihydro-imidazol-1-yl}-(4-pyrrolidin-1-yl-piperazin-1-yl)-methanone hydrochloride. HR-MS (ES, m/z) calculated for $C_{34}H_{38}N_4O_3FCl_2[(M+H)^+]$639.2300, observed 639.2303.

EXAMPLE 12
2-Amino-1-{4-[4,5-bis-(4-chloro-phenyl)-2-(2-isopropoxy-4-methoxy-phenyl)-4,5-dihydro-imidazole-1-carbonyl]-piperzin-1-yl}-ethanone

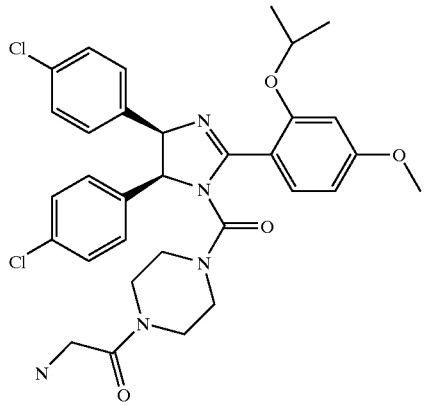

[4,5-Bis-(4-chloro-phenyl)-2-(2-isopropoxy-4-methoxy-phenyl)-4,5-dihydro-imidazol-1-yl]-piperazin-1-yl-methanone (52 mg, 0.092 mmol, example 10) was added to a solution of N-(t-butoxycarbonyl)glycine (21 mg, 0.119 mmol) in THF (12 mL), followed by diisopropyl carbodiimide (19.7 μL, 0.125 mmol). After 3 h, the reaction mixture was concentrated and diluted with methylene chloride. The mixture was washed with aqueous sodium carbonate, water and brine, and dried over sodium sulfate. Evaporation of the solvents and chromatography of the residue over silica using 1–2% methanol in methylene chloride gave (2-{4-[4,5-bis-(4-chloro-phenyl)-2-(2-isopropoxy-4-methoxy-phenyl)-4,5-dihydro-imidazole-1-carbonyl]-piperazin-1-yl}-2-oxo-ethyl)-carbomic acid tert-butyl ester (54 mg, 81%).

Trifluoroacetic acid (2 mL, 26 mmol) was added to a solution of (2-{4-[4,5-bis-(4-chloro-phenyl)-2-(2-isopropoxy-4-methoxy-phenyl)-4,5-dihydro-imidazole-1-carbonyl]-piperazin-1-yl}-2-oxo-ethyl)-carbomic acid tert-butyl ester (40 mg, 0.054 mmol) in methylene chloride (6 mL). The reaction mixture was stirred for 2.5 h and diluted with methylene chloride. The mixture was washed aqueous sodium carbonate, water and brine, and dried over sodium sulfate. Evaporation of the solvents and chromatography of the residue over silica gel with 5–10% methanol in methylene chloride gave 2-amino-1-{4-[4,5-bis-(4-chloro-phenyl)-2-(2-isopropoxy-4-methoxy-phenyl)-4,5-dihydro-imidazole-1-carbonyl]-piperazin-1-yl}-ethanone (22 mg, 65%). HR-MS (ES, m/z) calculated for $C_{32}H_{36}N_5O_4Cl_2[(M+H)^+]$624.2139, observed 624.2147.

EXAMPLE 13

In a similar manner as described in example 12, the following compounds were prepared.

a) 1-{4-[4,5-Bis-(4-chloro-phenyl)-2-(2-isopropoxy-4-methoxy-phenyl)-4,5-dihydro-imidazole-1-carbonyl]-piperazin-1-yl}-ethanone. HR-MS (ES, m/z) calculated for $C_{32}H_{35}N_4O_5Cl_2[(M+H)^+]$625.1979, observed 625.1984

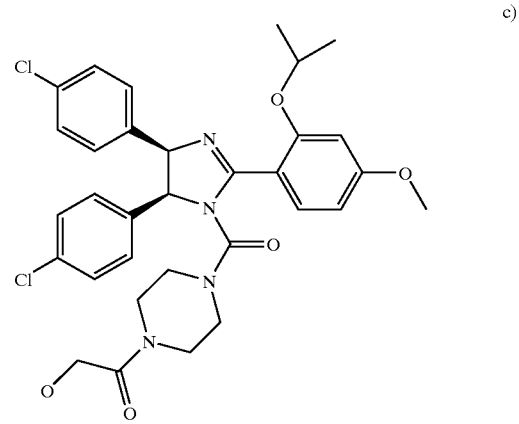

c)

b) 1-{4-[4,5-Bis-(4-chloro-phenyl)-2-(2-isopropoxy-4-methoxy-phenyl)-4,5-dihydro-imidazole-1-carbonyl]-piperazin-1-yl}-2,3-dihydroxy-propan-1-one. HR-MS (ES, m/z) calculated for $C_{33}H_{37}N_4O_6Cl_2[(M+H)^+]$ 655.2085, observed 655.2090.

EXAMPLE 14
[4,5-Bis-(4-chloro-phenyl)-2-(2-isopropoxy-4-methoxy-phenyl)-4,5-dihydro-imidazol-1-yl]-[4-(2,3-dihydroxy-propyl)-piperazin-1-yl]-methanone

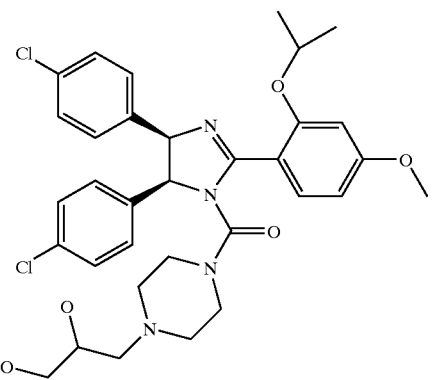

[4,5-Bis-(4-chloro-phenyl)-2-(2-isopropoxy-4-methoxy-phenyl)-4,5-dihydro-imidazol-1-yl]-piperazin-1-yl-methanone (50 mg, 0.088 mmol, example 10 g) was dissolved in anhydrous methanol (10 mL). Glycidol (0.15 mL, 2.26 mmol) was added and the reaction was heated at 40° C. for 20 h. The mixture was cooled to room temperature and concentrated in vacuo. Chromatography of the residue over silica gel using 1–6% methanol in methylene chloride gave [4,5-bis-(4-chloro-phenyl)-2-(2-isopropoxy-4-methoxy-phenyl)-4,5-dihydro-imidazol-1-yl]-[4-(2,3-dihydroxy-propyl)-piperazin-1-yl]-methanone (25 mg, 44%). HR-MS (ES, m/z) calculated for $C_{33}H_{39}N_4O_5Cl_2[(M+H)^+]$ 641.2292, observed 641.2300.

EXAMPLE 15
4-[4,5-Bis-(4-chloro-phenyl)-2-(2-isopropoxy-4-methoxy-phenyl)-4,5-dihydro-imidazole-1-carbonyl]-piperazin-1-carboxylic acid dimethylamide

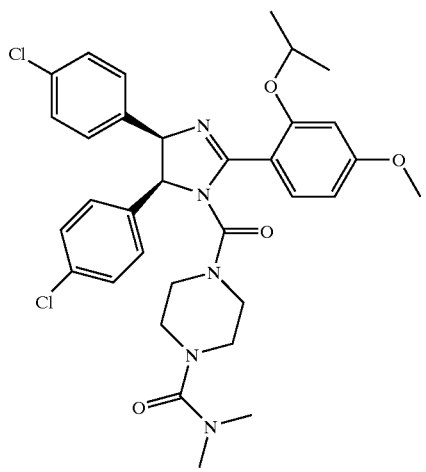

Phosgene (0.26 mL, 0.5 mmol, 1.93 M in toluene) was added to a solution of 4,5-bis-(4-chloro-phenyl)-2-(2-isopropoxy-4-methoxy-phenyl)-4,5-dihydro-imidazol-1-yl]-piperazin-1-yl-methanone (60 mg, 0.11 mmol, example 10 g) and triethylamine (97 μL, 0.70 mmol) in methylene chloride (10 mL). The reaction mixture was stirred for 1 h. The solvents were evaporated and the residue was dried under high vacuum for 30 min. The residue was redissolved in methylene chloride (10 mL). Dimethylamine (0.993 mL, 1.986 mmol, 2 M in THF) was added and the reaction mixture was stirred overnight. The mixture was washed with brine and the aqueous layer was extracted with methylene chloride. The combined organic extracts were dried (MgSO₄) and evaporated. Purification of the residue using reversed phase HPLC gave 4-[4,5-bis-(4-chloro-phenyl)-2-(2-isopropoxy-4-methoxy-phenyl)-4,5-dihydro-imidazole-1-carbonyl]-piperazin-1-carboxylic acid dimethylamide (48 mg, 68%). HR-MS (ES, m/z) calculated for $C_{33}H_{38}N_5O_4Cl_2[(M+H)^+]$638.2296, observed 638.2299.

EXAMPLE 16
4-[4,5-Bis-(4-chloro-phenyl)-2-(2-isopropoxy-4-methoxy-phenyl)-4,5-dihydro-imidazole-1-carbonyl]-piperazin-1-carboxylic acid amide

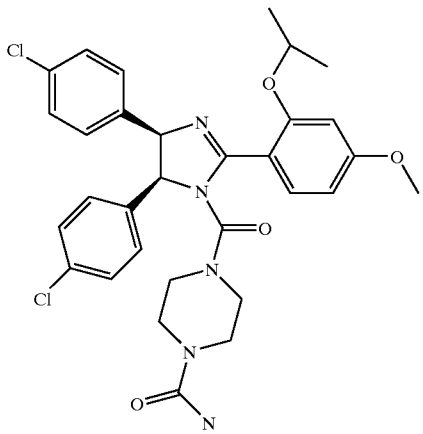

The named compound was prepared in a similar manner as described in example 15. HR-MS (m/z) calculated for $C_{31}H_{34}N_5O_4Cl_2[(M+H)^+]$610.1983, observed 610.1985.

EXAMPLE 17
[4,5-Bis-(4-chloro-phenyl)-2-(2,4-diethoxy-phenyl)-4,5-dihydro-imidazol-1-yl]-piperazin-1-yl-methanone trifluoroacetate salt

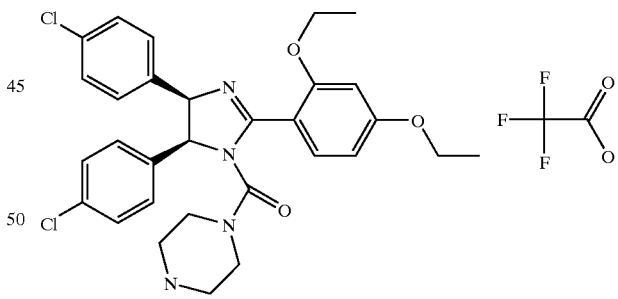

A mixture of 2,4-diethoxybenzaldehyde (5.0 g, 25.7 mmol), sodium acetate (4.23 g, 51.6 mmol), nitroethane (3.86 g, 51.4 mmol) in acetic acid (7 mL) was heated at reflux for 6 h. The mixture was then cooled and poured onto ice-water. The solids were filtered off, washed with water and dried. Chromatography of the residue over silica gel using 2–5% ethyl acetate in hexanes followed recrystallization in ethyl acetate gave 2,4-diethoxybenzonitrile (1.86 g, 38%).

Hydrogen chloride gas was passed through a solution of 2,4-diethoxybenzonitrile (1.86 g, 9.7 mmol) in absolute ethanol (20 mL) in a pressure tube for 1 h at −10° C. The tube was sealed and stirred at room temperature for 12 d.

Evaporation of the solvents and trituration of the residue in diethyl ether gave ethyl 2,4-diethoxy-benzimidate hydrochloride (2.53 g, 95%).

A mixture of ethyl 2,4-diethoxy-benzimidate hydrochloride (0.76 g, 2.79 mmol), meso-1,2-bis-(4-chloro-phenyl)-ethane-1,2-diamine (0.65 mg, 2.327 mmol, prepared according to the procedure described by Vogtle, F.; Goldschmitt, E. *Chem. Ber.* 1976, 109, 1–40) and triethylamine (0.489 mL, 3.49 mmol) in ethanol (10 mL) was heated at reflux for 4 h. The solvent was removed to give a yellow paste. Aqueous sodium bicarbonate was added and it was extracted with methylene chloride. The combined organic extracts were washed with water and brine, and dried over sodium sulfate. Chromatography of the residue over silica gel with 70% ethyl acetate-hexane gave 4,5-bis-(4-chloro-phenyl)-2-(2,4-diethoxy-phenyl)-4,5-dihydro-1H-imidazole (0.50 g, 47%).

Phosgene (0.558 mL, 1.1 mmol, 1.93 M in toluene) was added dropwise to a mixture of triethylamine (0.216 mL, 1.54 mmol) and 4,5-bis-(4-chloro-phenyl)-2-(2,4-diethoxy-phenyl)-4,5-dihydro-1H-imidazole (0.10 g, 0.22 mmol) in methylene chloride (10 mL) at 0° C. The reaction mixture was stirred for 1 h at 0° C. and evaporated. The residue was kept under high vacuum for 30 min. Methylene chloride (5 mL) was added to the residue and the solution was added dropwise to a solution of piperazine (0.38 g, 4.4 mmol) in methylene chloride (5 mL) at 0° C. over 15 min. After 1 h, the reaction was worked up with aqueous sodium bicarbonate. The mixture was extracted with methylene chloride and washed with water and brine. The organic extracts were dried over sodium sulfate and evaporated. Purification using HPLC gave [4,5-Bis-(4-chloro-phenyl)-2-(2,4-diethoxy-phenyl)-4,5-dihydro-imidazol-1-yl]-piperazin-1-yl-methanone, trifluoroacetic acid salt (4.07 g, 87%). HR-MS (ES, m/z) calculated for $C_{30}H_{33}N_4O_3Cl_2[(M+H)^+]$ 567.1924, observed 567.1928.

EXAMPLE 18

In a similar manner as described in example 17 the following compounds were prepared.

a) [4,5-Bis-(4-chloro-phenyl)-2-(2,4-diethoxy-phenyl)-4,5-dihydro-imidazol-1-yl]-morpholin-4-yl-methanone. HR-MS (ES, m/z) calculated for $C_{30}H_{32}N_3O_4Cl_2[(M+H)^+]$568.1765, observed 568.1766

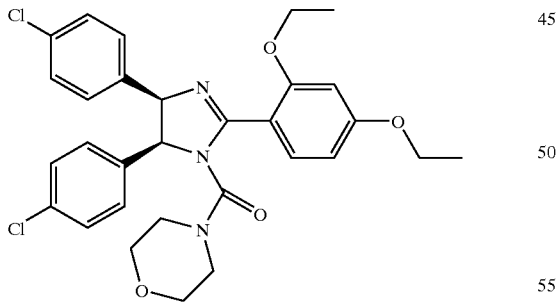

b) [4,5-Bis-(4-chloro-phenyl)-2-(2,4-diethoxy-phenyl)-4,5-dihydro-imidazol-1-yl]-[4-(2-hydroxy-ethyl)-piperazin-1-yl-]-methanone. HR-MS (ES, m/z) calculated for $C_{32}H_{37}N_4O_4Cl_2[(M+H)^+]$611.2187, observed 611.2203.

c) [4,5-Bis-(4-chloro-phenyl)-2-(2,4-diethoxy-phenyl)-4,5-dihydro-imidazol-1-yl]-(4-methyl-piperazin-1-yl)-methanone. HR-MS (ES, m/z) calculated for $C_{31}H_{35}N_4O_3Cl_2[(M+H)^+]$581.2081, observed 581.2087.

d) 1-{4-[4,5-Bis-(4-chloro-phenyl)-2-(2,4-diethoxy-phenyl)-4,5-dihydro-imidazole-1-carbonyl]-piperazin-1-yl}-ethanone. HR-MS (ES, m/z) calculated for $C_{32}H_{35}N_4O_4Cl_2[(M+H)^+]$609.2030, observed 609.2035.

e) [4,5-Bis-(4-chloro-phenyl)-2-(2,4-diethoxy-phenyl)-4,5-dihydro-imidazol-1-yl]-(4-methanesulfonyl-piperazin-1-yl)-methanone was prepared by sulfonylation of [4,5-bis-(4-chloro-phenyl)-2-(2,4-diethoxy-phenyl)-4,5-dihydro-imidazol-1-yl]-piperazin-1-yl-methanone (example 17). HR-MS (ES, m/z) calculated for $C_{31}H_{35}N_4O_5SCl_2[(M+H)^+]$645.1700, observed 645.1704.

f) [4,5-Bis-(4-chloro-phenyl)-2-(2,4-diethoxy-phenyl)-4,5-dihydro-imidazol-1-yl]-(4-pyrrolidin-1-yl-piperidin-1-yl)-methanone. HR-MS (ES, m/z) calculated for $C_{35}H_{41}N_4O_3Cl_2[(M+H)^+]$635.2550, observed 635.2561.

g) [4,5-Bis-(4-bromo-phenyl)-2-(2,4-diethoxy-phenyl)-4,5-dihydro-imidazol-1-yl]-(4-methyl-piperazin-1-yl)-methanone. HR-MS (ES, m/z) calculated for $C_{31}H_{35}N_4O_3Br_2[(M+H)^+]$669.1071, observed 669.1074.

h) [4,5-Bis-(4-bromo-phenyl)-2-(2,4-diethoxy-phenyl)-4,5-dihydro-imidazol-1-yl]-(4-ethyl-piperazin-1-yl-)-methanone. HR-MS (ES, m/z) calculated for $C_{32}H_{37}N_4O_3Br_2[(M+H)^+]$683.1227, observed 683.1228.

i) [4,5-Bis-(4-bromo-phenyl)-2-(2,4-diethoxy-phenyl)-4,5-dihydro-imidazol-1-yl]-morpholin-4-yl-methanone. HR-MS (ES, m/z) calculated for $C_{30}H_{32}N_3O_4Br_2[(M+H)^+]$656.0754, observed 656.0760.

EXAMPLE 19

In a similar manner as described in example 15, the following compounds were prepared from [4,5-bis-(4-chloro-phenyl)-2-(2,4-diethoxy-phenyl)-4,5-dihydro-imidazol-1-yl]-piperazin-1-yl-methanone (example 17).

a) 4-[4,5-Bis-(4-chloro-phenyl)-2-(2,4-diethoxy-phenyl)-4,5-dihydro-imidazole-1-carbonyl]-piperazine-1-carboxylic acid amide. HR-MS (ES, m/z) calculated for $C_3H_{34}N_5O_4Cl_2[(M+H)^+]$610.1983, observed 610.1983

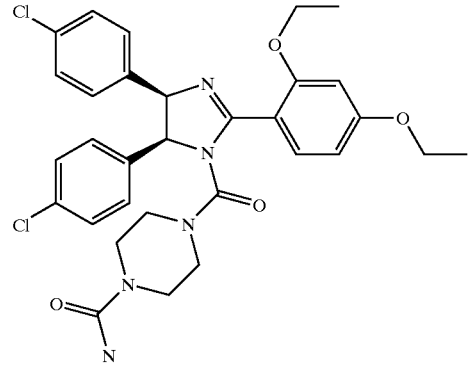

b) 4-[4,5-Bis-(4-chloro-phenyl)-2-(2,4-diethoxy-phenyl)-4,5-dihydro-imidazole-1-carbonyl]-piperazine-1-carboxylic acid dimethylamide. HR-MS (ES, m/z) calculated for $C_{33}H_{38}N_5O_4Cl_2[(M+H)^+]$638.2296, observed 638.2297.

EXAMPLE 20

[4,5-Bis-(4-chloro-phenyl)-2-(4-dimethylamino-2-ethoxy-phenyl)-4,5-dihydro-imidazol-1-yl]-piperazin-1-yl-methanone

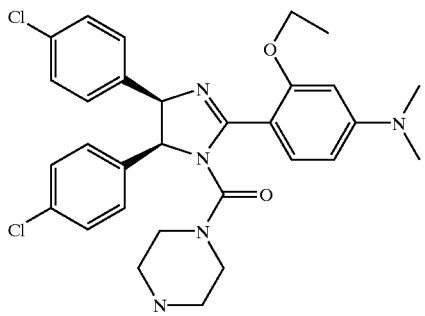

Iodine (6.35 g, 25 mmol) in methylene chloride (300 mL) was added dropwise over 3 h to a stirred suspension of thallium(I) acetate (7.90 g, 30 mmol) and 3-dimethylaminophenol (3.43 g, 25 mmol) in methylene chloride (300 mL). The resulting mixture was stirred at room temperature for 24 h and filtered. Evaporation of the solvents and chromatography of the residue over silica gel using 0–5% diethyl ether in hexanes gave 5-dimethylamino-2-iodophenol (2.35 g, 36%).

A mixture of 5-dimethylaminol-2-iodophenol (0.90 g, 3.42 mmol), cesium carbonate (2.79 g, 8.55 mmol) and iodoethane (0.81 mL, 10 mmol) in acetone (5 mL) was heated at reflux for 2 h. The reaction mixture was cooled to room temperature and water was added. The mixture was extracted with diethyl ether (3×). The combined organic extracts were washed with brine, dried over magnesium sulfate and evaporated. Chromatography of the residue over silica gel using hexanes gave N,N-dimethyl-2-ethoxy-4-iodo-aniline (0.75 g, 76%).

N,N-dimethyl-2-ethoxy-4-iodo-aniline (0.75 g, 2.58 mmol) was dissolved in DMF (4 mL). Zinc cyanide (0.18 g, 1.54 mmol) was added. Argon was passed through the mixture for 10 min. Tetrakis(triphenylphosphine)palladium (148 mg, 0.13 mmol) was added and the mixture was heated at 110° C. for 24 h. The reaction mixture was cooled and poured into water. The mixture was extracted with ethyl acetate, washed with brine and dried over magnesium sulfate. Evaporation of the solvents and chromatography of the residue over silica gel using 20% ethyl acetate in hexanes gave N,N-dimethyl-2-ethoxy-4-cyano-aniline (187 mg, 38%).

Hydrogen chloride gas was passed through a solution of N,N-dimethyl-2-ethoxy-4-cyano-aniline (0.185 g, 0.97 mmol) in ethanol (5 mL) at 0° C. for 30 min. The pressure tube was sealed and stirred for 2 d at room temperature. The tube was cooled to 0° C. before the pressure was released. Evaporation of the solvents and trituration of the residue in diethyl ether gave ethyl 4-(N,N-dimethylamino)-2-ethoxy-benzimidate hydrochloride as a white powder (0.25 g, 95%).

Triethylamine (0.28 mL, 2.0 mmol) was added to a mixture of 4-(N,N-dimethylamino)-2-ethoxy-benzimidate hydrochloride (250 mg, 0.92 mmol) and meso-1,2-bis-(4-chloro-phenyl)-ethane-1,2-diamine (190 mg, 0.68 mmol, prepared according to the procedure described by Vogtle, F.; Goldschmitt, E. Chem. Ber. 1976, 109, 1–40) in ethanol (5 mL). The mixture was heated at reflux overnight. The reaction was worked up with aqueous sodium bicarbonate and extracted with methylene chloride. The organic extracts were washed with brine and dried over sodium sulfate. Evaporation of the solvents and chromatography of the residue over silica gel using 10–30% methanol in methylene chloride gave {4-[4,5-bis-(4-chloro-phenyl)-4,5-dihydro-1H-imidazol-2-yl]-3-ethoxy-phenyl}-dimethyl-amine as a white foam (0.18 g, 59%).

Phosgene (0.47 mL, 0.91 mmol, 1.93 M in toluene) was added to a stirred solution of {4-[4,5-bis-(4-chloro-phenyl)-4,5-dihydro-1H-imidazol-2-yl]-3-ethoxy-phenyl}-dimethyl-amine (83 mg, 0.18 mmol) and triethylamine (0.14 mL, 1 mmol) in THF (3 mL) at 0° C. over a period of 5 min. The mixture was stirred for 1 h and evaporated. The residue was dissolved in methylene chloride (2 mL) and added dropwise to a stirred solution of piperazine (0.239 g, 2.77 mmol) in methylene chloride (2 mL) at room temperature for 1 h. The mixture was diluted with aqueous sodium bicarbonate and extracted with methylene chloride. The organic extracts were washed with brine and dried over sodium sulfate. Evaporation of the solvents and chromatography of the residue over silica gel using 0–10% methanol in methylene chloride gave [4,5-bis-(4-chloro-phenyl)-2-(4-dimethylamino-2-ethoxy-phenyl)-4,5-dihydro-imidazol-1-yl]-piperazin-1-yl-methanone as a white foam (68 mg, 66%). HR-MS (ES, m/z) calculated for $C_{30}H_{34}N_5O_2Cl_2$ [(M+H)$^+$]566.2084, observed 566.2088.

EXAMPLE 21

In a similar manner as described in example 20 the following compounds were prepared.

a) [4,5-Bis-(4-chloro-phenyl)-2-(2-ethoxy-4-ethyl-phenyl)-4,5-dihydro-imidazol-1-yl]-piperazin-1-yl-methanone. HR-MS (ES, m/z) calculated for $C_{30}H_{33}N_4O_2Cl_2$[(M+H)$^+$]551.1975, observed 551.1984

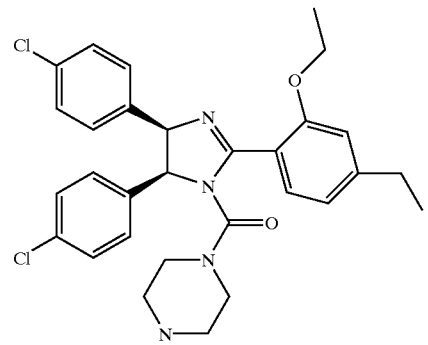

b) [4,5-Bis-(4-chloro-phenyl)-2-(2-ethoxy-4-methyl-phenyl)-4,5-dihydro-imidazol-1-yl]-piperazin-1-yl-methanone. HR-MS (ES, m/z) calculated for $C_{29}H_{31}N_4O_2Cl_2$[(M+H)$^+$]537.1819, observed 537.1824.

c) [4,5-Bis-(4-chloro-phenyl)-2-(4-ethyl-2-isopropoxy-phenyl)-4,5-dihydro-imidazol-1-yl]-piperazin-1-yl-methanone. HR-MS (ES, m/z) calculated for $C_{31}H_{35}N_4O_2Cl_2$[(M+H)$^+$]565.2132, observed 565.2135.

d) [4,5-Bis-(4-chloro-phenyl)-2-(2-isopropoxy-4-methyl-phenyl)-4,5-dihydro-imidazol-1-yl]-piperazin-1-yl-methanone. HR-MS (ES, m/z) calculated for $C_{30}H_{33}N_4O_2Cl_2$[(M+H)$^+$]551.1975, observed 551.1980.

e) 1-{4-[4,5-Bis-(4-chloro-phenyl)-2-(4-dimethylamino-2-ethoxy-phenyl)-4,5-dihydro-imidazole-1-carbonyl]-piperazin-1-yl}-ethanone. HR-MS (ES,m/z) calculated for $C_{32}H_{36}N_5O_3Cl_2$[(M+H)$^+$]608.2190, observed 608.2201.

EXAMPLE 22

In a similar manner as described in example 20, the following compounds were prepared.

a) [4,5-Bis-(4-chloro-phenyl)-2-(2-ethoxy-5-methyl-phenyl)-4,5-dihydro-imidazol-1-yl]-piperazin-1-yl-methanone, trifluoroacetic acid salt. HR-MS (ES, m/z) calculated for $C_{32}H_{31}N_4O_2Cl_2[(M+H)^+]537.1819$, observed 537.1826

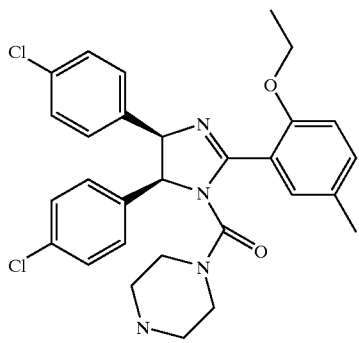

b) [4,5-Bis-(4-chloro-phenyl)-2-(2-ethoxy-4-fluoro-phenyl)-4,5-dihydro-imidazol-1-yl]-(4pyrrolidin-1yl-piperidin-1-yl)-methanone. HR-MS (ES, m/z) calculated for $C_{33}H_{36}N_4O_2Cl_2F[(M+H)^+]609.2194$, observed 609.2204.

c) [4,5-Bis-(4-chloro-phenyl)-2-(2-ethoxy-4-fluoro-phenyl)-4,5-dihydro-imidazol-1-yl]-(4-dimethylamino-piperidin-1-yl)-methanone. HR-MS (ES, m/z) calculated for $C_{31}H_{34}N_4O_2Cl_2F[(M+H)^+]583.2038$, observed 583.2041.

d) [4,5-Bis-(4-chloro-phenyl)-2-(2-ethoxy-4-fluoro-phenyl)-4,5-dihydro-imidazol-1-yl]-piperazin-1-yl-methanone. HR-MS (ES, m/z) calculated for $C_{28}H_{28}N_4O_2Cl_2F[(M+H)^+]541.1568$, observed 541.1571.

e) [4,5-Bis-(4-chloro-phenyl)-2-(4-fluoro-2-isopropoxy-phenyl)-4,5-dihydro-imidazol-1-yl]-(4-pyrrolidin-1-yl-piperidin-1-yl)-methanone. HR-MS (ES, m/z) calculated for $C_{34}H_{38}N_4O_2FCl_2[(M+H)^+]623.2351$, observed 623.2360.

f) [4,5-Bis-(4-chloro-phenyl)-2-(4-fluoro-2-isopropoxy-phenyl)-4,5-dihydro-imidazol-1-yl]-(4dimethylamino-piperidin-1-yl)-methanone. HR-MS (ES, m/z) calculated for $C_{32}H_{36}N_4O_2FCl_2[(M+H)^+]597.2194$, observed 597.2197.

g) [4,5-Bis-(4-chloro-phenyl)-2-(4-fluoro-2-isopropoxy-phenyl)-4,5-dihydro-imidazol-1-yl]-(4-methyl-piperazin-1-yl)-methanone. HR-MS (ES, m/z) calculated for $C_{30}H_{32}N_4O_2FCl_2[(M+H)^+]569.1881$, observed 569.1887.

h) [4,5-Bis-(4-chloro-phenyl)-2-(4-fluoro-2-isopropoxy-phenyl)-4,5-dihydro-imidazol-1-yl]-piperazin-1-yl-methanone. HR-MS (ES, m/z) calculated for $C_{29}H_{30}N_4O_2FCl_2[(M+H)^+]551.1725$, observed 551.1726.

i) [4,5-Bis-(4-chloro-phenyl)-2-(4-fluoro-2-isopropoxy-phenyl)-4,5-dihydro-imidazol-1-yl]-(4-methanesulfonyl-piperazin-1-yl)-methanone. HR-MS (ES, m/z) calculated for $C_{30}H_{32}N_4O_4SFCl_2[(M+H)^+]633.1500$, observed 633.1506.

j) 4-[4,5-Bis-(4-chloro-phenyl)-2-(4-fluoro-2-isopropoxy-phenyl)-4,5-dihydro-imidazole-1-carbonyl]-piperazin-2-one. HR-MS (ES, m/z) calculated for $C_{29}H_{28}N_4O_3FCl_2[(M+H)^+]569.1517$, observed 569.1529.

k) [4,5-Bis-(4-chloro-phenyl)-2-chroman-8-yl-4,5-dihydro-imidazol-1-yl]-piperazin-1-yl-methanone was prepared from 8-bromo-chroman (prepared from 2,6-dibromo-phenol using the procedure reported by Thomas, G. H. et al. *Tetrahedron Lett.* 1998, 39, 2219–22). HR-MS (ES, m/z) calculated for $C_{29}H_{29}N_4O_2Cl_2[(M+H)^+]535.1662$, observed 535.1672.

l) 4-[4,5-Bis-(4-bromo-phenyl)-2-(2-ethoxy-4-fluoro-phenyl)-4,5-dihydro-imidazole-1-carbonyl]-piperazin-2-one. HR-MS (ES, m/z) calculated for $C_{28}H_{26}N_4O_3FBr_2[(M+H)^+]643.0350$, observed 643.0349.

m) [4,5-Bis-(4-bromo-phenyl)-2-(2-ethoxy-4-fluoro-phenyl)-4,5-dihydro-imidazol-1-yl]-morpholin-4-yl-methanone. HR-MS (ES, m/z) calculated for $C_{28}H_{27}N_3O_3FCl_2[(M+H)^+]630.0398$, observed 630.0414.

n) [4,5-Bis-(4-bromo-phenyl)-2-(2-ethoxy-4-fluoro-phenyl)-4,5-dihydro-imidazol-1-yl]-(4-pyrrolidin-1-yl-piperidin-1-yl)-methanone. HR-MS (ES, m/z) calculated for $C_{33}H_{36}N_4O_2FBr_2[(M+H)^+]697.1184$, observed 697.1188.

o) [4,5-Bis-(4-bromo-phenyl)-2-(2-ethoxy-4-fluoro-phenyl)-4,5-dihydro-imidazol-1-yl]-(4-dimethylamino-piperidin-1-yl)-methanone. HR-MS (ES, m/z) calculated for $C_3H_{34}N_4O_2FBr_2[(M+H)^+]$ 671.1027, observed 671.1036.

p) [4,5-Bis-(4-bromo-phenyl)-2-(2-ethoxy-4-fluoro-phenyl)-4,5-dihydro-imidazol-1-yl]-piperazin-1-yl-methanone. HR-MS (ES, m/z) calculated for $C_{28}H_{28}N_4O_2FBr_2[(M+H)^+]629.0558$, observed 629.0569.

EXAMPLE 23

[4,5-Bis-(4-chloro-phenyl)-2-(2-cyclopentyloxy-4-methoxy-phenyl)-4,5-dihydro-imidazol-1-yl]-piperazin-1-yl-methanone

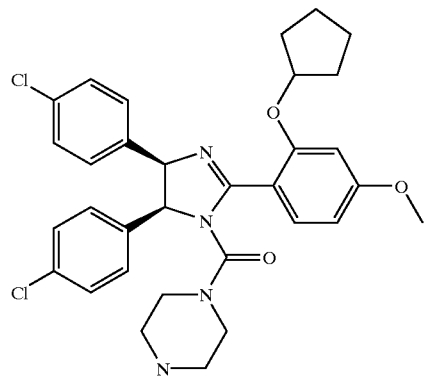

To a solution of 2-hydroxy-4-methoxy-benzonitrile (90 mg, 0.60 mmol, example 9), cyclopentanol (55 mg, 0.64 mmol) and triphenylphosphine (167 mg, 0.64 mmol) in THF (3 mL) at −78° C. was added diethyl azodicarboxylate (0.16 mL, 0.860 mmol, 85%). The cooling bath was removed and the reaction was allowed to warm up to room temperature over 1.5 h. The reaction mixture was concentrated in vacuo, and purification of the residue by flash chromatography (Biotage system, KP-Sil™ 32–63 μm, 60 Å silica gel)

eluting with 0–8% diethyl ether in hexanes yielded 2-cyclopentyloxy-4-methoxy-benzonitrile as a clear liquid (125 mg, 90%).

Hydrogen chloride gas was passed through a solution of 2-cyclopentyloxy-4-methoxy-benzonitrile (0.12 g, 0.55 mmol) in absolute ethanol (15 mL) in a pressure tube for 1 h at 0° C. The tube was sealed and stirred at room temperature for 3 d. Evaporation of the solvents and trituration of the residue in diethyl ether gave ethyl 2-cyclopentyloxy-4-methoxy-benzimidate hydrochloride (0.17 g, 100%).

A mixture of ethyl 2-cyclopentyloxy-4-methoxy-benzimidate hydrochloride (0.16 g, 0.57 mmol), meso-1,2-bis-(4-chloro-phenyl)-ethane-1,2-diamine (0.17 g, 0.56 mmol, prepared according to the procedure described by Vogtle, F.; Goldschmitt, E. Chem. Ber. 1976, 109, 1–40) in ethanol (2 mL) was heated at reflux for 18 h. The solvent was removed to give a yellow paste. Aqueous sodium bicarbonate was added and it was extracted with methylene chloride. The combined organic extracts were washed with water and brine, and dried over sodium sulfate. Chromatography of the residue over silica gel with 0–5% methanol in methylene chloride gave 4,5-bis-(4-chloro-phenyl)-2-(2-cyclopentyloxy-4-methoxy-phenyl)-4,5-dihydro-1H-imidazole.

Phosgene (0.48 mL, 0.925 mmol, 1.93 M in toluene) was added dropwise to a mixture of triethylamine (0.14 mL, 1.0 mmol) and 4,5-bis-(4-chloro-phenyl)-2-(2-cyclopentyloxy-4-methoxy-phenyl)-4,5-dihydro-1H-imidazole (89 mg in THF (2 mL) at 0° C. The reaction mixture was stirred for 1 h at 0° C. and evaporated. The residue was kept under high vacuum for 30 min. Methylene chloride (2 mL) was added to the residue and the solution was added dropwise to a solution of piperazine (0.24 g, 2.78 mmol) in methylene chloride (2 mL) at 0° C. After 1 h, the reaction was worked up with aqueous sodium bicarbonate. The mixture was extracted with methylene chloride and washed with water and brine. The organic layer was extracted with 0.5 N HCl (2×50 mL). The combined aqueous layers were cooled to 0° C. and basified using 2 N NaOH. The mixture was extracted with methylene chloride (3×50 mL). The organic extracts were dried over sodium sulfate and evaporated. Flash chromatography of the residue over silica gel using 3–6% methanol in methylene chloride gave [4,5-Bis-(4-chloro-phenyl)-2-(2-cyclopentyloxy-4-methoxy-phenyl)-4,5-dihydro-imidazol-1-yl]-piperazin-1-yl-methanone (89 mg, 81%). HR-MS (ES, m/z) calculated for $C_{32}H_{35}N_4O_3Cl_2$ $[(M+H)^+]$593.2081, observed 593.2084.

EXAMPLE 24

In a similar manner as described in example 23 and example 9, the following compounds were prepared.

a) {4,5-Bis-(4-chloro-phenyl)-2-[2-(2-dimethylamino-ethoxy)-4-methoxy-phenyl]-4,5-dihydro-imidazol-1-yl}-piperazin-1-yl-methanone. HR-MS (ES, m/z) calculated for $C_3H_{36}N_5O_3Cl_2[(M+H)^+]$596.2190, observed 596.2196

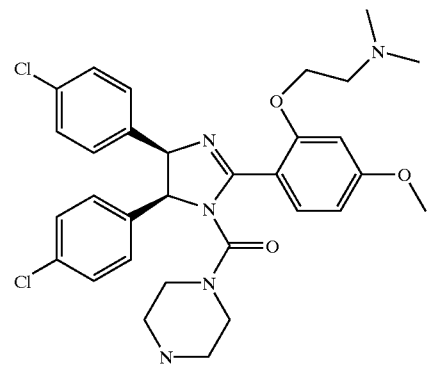

b) {4,5-Bis-(4-chloro-phenyl)-2-[2-(2-imidazol-1-yl-ethoxy)-4-methoxy-phenyl]-4,5-dihydro-imidazol-1-yl}-piperazin-1-yl-methanone. HR-MS (ES, m/z) calculated for $C_{32}H_{33}N_6O_3Cl_2[(M+H)^+]$619.1986, observed 619.1988.

EXAMPLE 25
[2-(4-Chloro-2-ethoxy-phenyl)-4,5-bis-(4-chloro-phenyl)-4,5-dihydro-imidazol-1-yl]-piperazin-1-yl-methanone hydrochloride

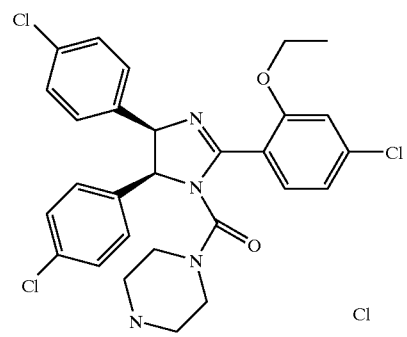

To a solution of 4-chloro-2-fluoro-benzonitrile (1.0 g, 6.428 mmol) in ethanol (10 mL) were added sodium ethoxide solution (4.8 mL, 12.86 mmol, 21% wt in ethanol). The reaction mixture was heated at gently reflux for 12 h. The solvent was removed and the residue was partitioned between water (10 mL) and diethyl ether (20 mL). The layers were separated and the product was extracted with diethyl ether (20 mL). The organic layers were washed with brine (5 mL) and dried over anhydrous sodium sulfate. The solids were filtered off and the filtrate was concentrated in vacuo. Purification of the residue by flash chromatography (Biotage system, KP-Sil™ 32–63 μm, 60 Å silica gel) eluting with 5% ethyl acetate in hexanes yielded 4-chloro-2-ethoxy-benzonitrile (0.67 g, 57%).

[2-(4-Chloro-2-ethoxy-phenyl)-4,5-bis-(4-chloro-phenyl)-4,5-dihydro-imidazol-1-yl]-piperazin-1-yl-methanone hydrochloride was prepared from 4-chloro-2-ethoxy-benzonitrile in a similar manner as described in example 23. HR-MS (ES, m/z) calculated for $C_{28}H_{28}N_4O_2Cl_3[(M+H)^+]$557.1273, observed 557.1277.

EXAMPLE 26

In a similar manner as described in example 23 and example 25, the following compounds were prepared.

a) [2-(4-Chloro-2-ethoxy-phenyl)-4,5-bis-(4-chloro-phenyl)-4,5-dihydro-imidazol-1-yl]-(4-methylpiperazin-1-yl)-methanone hydrochloride. HR-MS (ES, m/z) calculated for $C_{29}H_{30}N_4O_2Cl_2[(M+H)^+]$ 571.1429, observed 571.1438

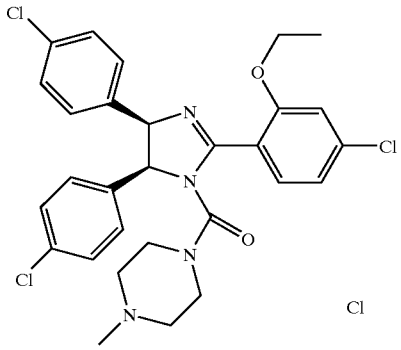

b) [2-(4-Chloro-2-ethoxy-phenyl)-4,5-bis-(4-chloro-phenyl)-4,5-dihydro-imidazol-1-yl]-(4-pyrrolidin-1-yl-piperidin-1-yl)-methanone hydrochloride. HR-MS (ES, m/z) calculated for $C_{33}H_{36}N_4O_2Cl_3[(M+H)^+]$ 625.1899, observed 625.1908.

c) [2-(4-Chloro-2-ethoxy-phenyl)-4,5-bis-(4-chloro-phenyl)-4,5-dihydro-imidazol-1-yl]-morpholin-4-yl-methanone. HR-MS (ES, m/z) calculated for $C_{28}H_{27}N_3O_3Cl_3[(M+H)^+]$ 558.1113, observed 558.1118.

d) 1-{4-[2-(4-Chloro-2-ethoxy-phenyl)-4,5-bis-(4-chloro-phenyl)-4,5-dihydro-imidazole-1-carbonyl]-piperazin-1-yl}-ethanone. HR-MS (ES, m/z) calculated for $C_{30}H_{30}N_4O_3Cl_3[(M+H)^+]$ 599.1378, observed 599.1388.

e) [2-(4-Chloro-2-ethoxy-phenyl)-4,5-bis-(4-chloro-phenyl)-4,5-dihydro-imidazol-1-yl]-[4-(2-hydroxy-ethyl-piperazin-1-yl]-methanone hydrochloride. HR-MS (ES, m/z) calculated for $C_{30}H_{32}N_4O_3Cl_3[(M+H)^+]$ 601.1535, observed 601.1543.

f) 4-[2-(4-Chloro-2-ethoxy-phenyl)-4,5-bis-(4-chloro-phenyl)-4,5-dihydro-imidazole-1-carbonyl-piperazin-2-one. HR-MS (ES, m/z) calculated for $C_{28}H_{26}N_4O_3Cl_3[(M+H)^+]$ 571.1065, observed 571.1071.

EXAMPLE 27

[4,5-Bis-(4-chloro-phenyl)-2-(4-ethoxy-2-isopropoxy-phenyl)-4,5-dihydro-imidazol-1-yl]-piperazin-1-yl-methanone

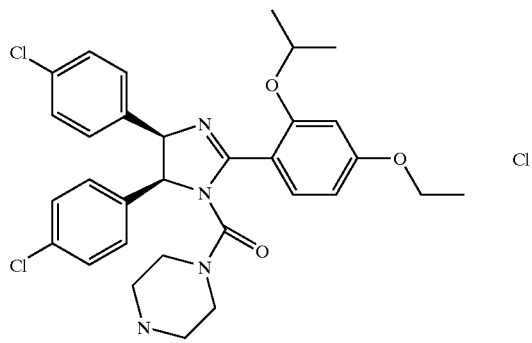

To a solution of 4-bromo-benzene-1,3-diol (1.50 g, 7.94 mmol) in acetone (10 mL) were added potassium carbonate (1.1 g, 7.94 mmol) and 2-iodopropane (1.58 mL, 15.87 mmol). The reaction mixture was heated at gentle reflux for 12 h. The solvent was removed to give a white paste. It was then taken in diethyl ether (50 mL). The white solids were filtered off and the filtrate was concentrated. Purification of the residue by Biotage flash chromatography eluting with 10% ethyl acetate in hexanes gave 4-bromo-3-isopropoxy-phenol (0.77 g, 42%).

To a solution of 4-bromo-3-isopropoxy-phenol (0.50 g, 2.16 mmol) in acetone (3 mL) were added potassium carbonate (0.30 g, 2.16 mmol) and ethyl iodide (0.35 mL, 4.33 mmol). The reaction mixture was heated at gentle reflux for 12 h. The solvent was removed to give a white paste. It was then taken in diethyl ether (50 mL). The white solids were filtered off and the filtrate was concentrated. Purification of the residue by Biotage flash chromatography eluting with 10% ethyl acetate in hexanes gave 1-bromo-4-ethoxy-2-isopropoxy-benzene (0.48 g, 86%).

To a solution of 1-bromo-4-ethoxy-2-isopropoxy-benzene (0.48 g, 1.85 mmol) in DMF (5 mL) was added zinc cyanide (217 mg, 1.85 mmol). The reaction was degassed by passing argon through the mixture for 2 h before tetrakis (triphenylphosphine)-palladium (0) (0.21 g, 0.185 mmol) was added. The reaction mixture was heated at 100–105° C. under argon for 12 h. The reaction mixture was taken up in diethyl ether (50 mL) and saturated sodium bicarbonate solution (5 mL). The product was extracted with diethyl ether (2×30 mL). The organic layers were washed with water (1×10 mL) and brine (1×10 mL), dried (sodium sulfate) and concentrated. Purification of the crude by Biotage flash chromatography eluting with 10–15% ethyl acetate in hexanes gave 4-ethoxy-2-isopropoxy-benzonitrile as a clear oil (0.31 g, 81%).

Hydrogen chloride gas was passed through a solution of 4-ethoxy-2-isopropoxy-benzonitrile (0.30 g, 1.46 mmol) in absolute ethanol (100 mL) in a pressure tube for 45 min at 0° C. The tube was sealed and stirred at room temperature for 4 d. The pressure was released only after the tube is cooled to 0° C. Evaporation of the solvents and trituration of the residue in diethyl ether gave ethyl 4-ethoxy-2-isopropoxy-benzimidate hydrochloride which was used without further purification.

A mixture of crude ethyl 4-ethoxy-2-isopropoxy-benzimidate hydrochloride and meso-1,2-bis-(4-chloro-phenyl)-ethane-1,2-diamine (0.41 g, 1.46 mmol, prepared according to the procedure described by Vogtle, F.; Goldschmitt, E. *Chem. Ber.* 1976, 109, 1–40) and triethylamine (0.205 mL, 1.46 mmol) in ethanol (25 mL) was heated at reflux for 3 h. The solvent was removed to give a yellow paste. Aqueous sodium bicarbonate was added and it was extracted with methylene chloride. The combined organic extracts were washed with water and brine, and dried over sodium sulfate. Chromatography of the residue over silica gel with 70% ethyl acetate-hexane gave 4,5-bis-(4-chloro-phenyl)-2-(4-ethoxy-2-isopropoxy-phenyl)-4,5-dihydro-1H-imidazole (0.50 g, 47%).

Phosgene (0.325 mL, 0.64 mmol, 1.93 M in toluene) was added dropwise to a mixture of triethylamine (0.126 mL, 0.896 mmol) and 4,5-bis-(4-chloro-phenyl)-2-(4-ethoxy-2-isopropoxy-phenyl)-4,5-dihydro-1H-imidazole (60 mg, 0.128 mmol) in methylene chloride (5 mL) at 0° C. The reaction mixture was stirred for 30 min at 0° C. and evaporated. The residue was kept under high vacuum for 30 min. Methylene chloride (5 mL) was added to the residue and the solution was added dropwise to a solution of piperazine (0.22 mg, 2.56 mmol) in methylene chloride (5 mL) at 0° C. over 15 min. After 1 h, the reaction was worked up with aqueous sodium bicarbonate. The mixture was extracted with methylene chloride and washed with water and brine. The organic extracts were dried over sodium sulfate and evaporated. Purification using reverse phase HPLC gave [4,5-bis-(4-chloro-phenyl)-2-(4-ethoxy-2-isopropoxy-phenyl)-4,5-dihydro-imidazol-1-yl]-piperazin-1-yl-methanone (6.5 mg, 8%). HR-MS (ES, m/z) calculated for $C_{31}H_{35}N_4O_3Cl_2[(M+H)^+]581.2081$, observed 581.2086.

EXAMPLE 28

In a similar manner as described in example 27 the following compounds were prepared.

a) [4,5-Bis-(4-chloro-phenyl)-2-(2-ethoxy-5-methoxy-phenyl)-4,5-dihydro-imidazol-1-yl]-piperazin-1-yl-methanone, trifluoroacetic acid salt. HR-MS (ES, m/z) calculated for $C_{29}H_{31}N_4O_3Cl_2[(M+H)^+]553.1768$, observed 553.1776

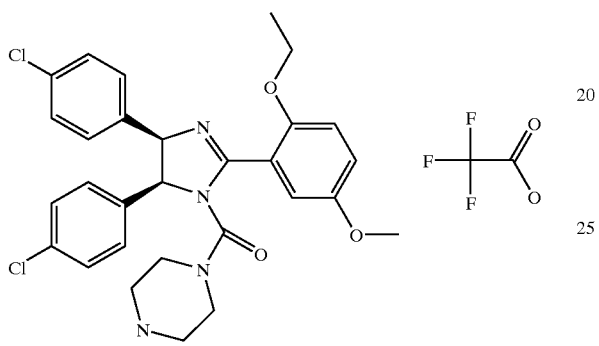

b) [4,5-Bis-(4-chloro-phenyl)-2-(2-ethoxy-5-methoxy-phenyl)-4,5-dihydro-imidazol-1-yl]-(4-methanesulfonyl-piperazin-1-yl)-methanone was prepared by sulfonylation of [4,5-bis-(4-chloro-phenyl)-2-(2-ethoxy-5-methoxy-phenyl)-4,5-dihydro-imidazol-1-yl]-piperazin-1-yl-methanone (example 28a). HR-MS (ES, m/z) calculated for $C_{30}H_{33}N_4O_5SCl_2[(M+H)^+]$ 631.1543, observed 631.1548.

c) [4,5-Bis-(4-chloro-phenyl)-2-(2-ethoxy-5-methoxy-phenyl)-4,5-dihydro-imidazol-1-yl]-[4-(2-hydroxy-ethyl)-piperazin-1-yl]-methanone hydrochloride. HR-MS (ES, m/z) calculated for $C_{31}H_{35}N_4O_4Cl_2[(M+H)^+]597.2030$, observed 597.2037.

d) [4,5-Bis-(4-chloro-phenyl)-2-(2,5-diethoxy-phenyl)-4,5-dihydro-imidazol-1-yl]-piperazin-1-yl-methanone hydrochloride. HR-MS (ES, m/z) calculated for $C_{30}H_{33}N_4O_3Cl_2[(M+H)^+]567.1924$, observed 567.1928.

e) [4,5-Bis-(4-chloro-phenyl)-2-(2,5-diethoxy-phenyl)-4,5-dihydro-imidazol-1-yl]-(4-methanesulfonyl-piperazin-1-yl)-methanone was prepared by sulfonylation of [4,5-bis-(4-chloro-phenyl)-2-(2,5-diethoxy-phenyl)-4,5-dihydro-imidazol-1-yl]-piperazin-1-yl-methanone (example 28d). HR-MS (ES, m/z) calculated for $C_{31}H_{35}N_4O_5SCl_2[(M+H)^+]645.1700$, observed 645.1714.

f) [4,5-Bis-(4-chloro-phenyl)-2-(4-ethoxy-2-isopropoxy-phenyl)-4,5-dihydro-imidazol-1-yl]-[4-(2-hydroxy-ethyl)-piperazin-1-yl]-methanone. HR-MS (ES, m/z) calculated for $C_{33}H_{39}N_4O_4Cl_2[(M+H)^+]625.2343$, observed 625.2350.

g) 4-[4,5-Bis-(4-chloro-phenyl)-2-(4-ethoxy-2-isopropoxy-phenyl)-4,5-dihydro-imidazole-1-carbonyl]-piperazin-2-one. HR-MS (ES, m/z) calculated for $C_{31}H_{33}N_4O_4Cl_2[(M+H)^+]595.1874$, observed 595.1879.

h) [4,5-Bis-(4-chloro-phenyl)-2-(5-ethoxy-2-isopropoxy-phenyl)-4,5-dihydro-imidazol-1-yl]-piperazin-1-yl-methanone. HR-MS (ES, m/z) calculated for $C_{31}H_{35}N_4O_3Cl_2[(M+H)^+]581.2081$, observed 581.2088.

i) [4,5-Bis-(4-chloro-phenyl)-2-(5-ethoxy-2-isopropoxy-phenyl)-4,5-dihydro-imidazol-1-yl]-(4-methanesulfonyl-piperazin-1-yl)-methanone was prepared by sulfonylation of [4,5-bis-(4-chloro-phenyl)-2-(5-ethoxy-2-isopropoxy-phenyl)-4,5-dihydro-imidazol-1-yl]-piperazin-1-yl-methanone (example 28h). HR-MS (ES, m/z) calculated for $C_{32}H_{37}N_4O_5SCl_2[(M+H)^+]659.1856$, observed 659.1864.

j) [4,5-Bis-(4-chloro-phenyl)-2-(5-ethoxy-2-isopropoxy-phenyl)-4,5-dihydro-imidazol-1-yl]-[4-(2-hydroxy-ethyl)-piperazin-1-yl]-methanone hydrochloride. HR-MS (ES, m/z) calculated for $C_{33}H_{39}N_4O_4Cl_2[(M+H)^+]625.2343$, observed 625.2352.

k) 1-{4-[4,5-Bis-(4-chloro-phenyl)-2-(4-ethoxy-2-isopropoxy-phenyl)-4,5-dihydro-imidazole-1-carbonyl]-piperazin-1-yl}-ethanone. HR-MS (ES, m/z) calculated for $C_{33}H_{37}N_4O_4Cl_2[(M+H)^+]623.2187$, observed 623.2194.

l) 1-{4-[4,5-Bis-(4-chloro-phenyl)-2-(5-ethoxy-2-isopropoxy-phenyl)-4,5-dihydro-imidazole-1-carbonyl]-piperazin-1-yl}-ethanone. HR-MS (ES, m/z) calculated for $C_{33}H_{37}N_4O_4Cl_2[(M+H)^+]623.2187$, observed 623.2195.

m) [4,5-Bis-(4-chloro-phenyl)-2-(4-ethoxy-2-isopropoxy-phenyl)-4,5-dihydro-imidazol-1-yl]-(4-pyrrolidin-1-yl-piperazin-1-yl)-methanone. HR-MS (ES, m/z) calculated for $C_{36}H_{43}N_4O_3Cl_2[(M+H)^+]$ 649.2707, observed 649.2717.

n) [4,5-Bis-(4-chloro-phenyl)-2-(2-isopropoxy-5-methoxy-phenyl)-4,5-dihydro-imidazol-1-yl]-piperazin-1-yl-methanone, trifluoroacetic acid salt. HR-MS (ES, m/z) calculated for $C_{30}H_{33}N_4O_3Cl_2[(M+H)^+]567.1924$, observed 567.1929.

o) [4,5-Bis-(4-chloro-phenyl)-2-(2,4-diisopropoxy-phenyl)-4,5-dihydro-imidazol-1-yl]-piperazin-1-yl-methanone. HR-MS (ES, m/z) calculated for $C_{32}H_{37}N_4O_3Cl_2[(M+H)^+]595.2237$, observed 595.2244.

p) [4,5-Bis-(4-chloro-phenyl)-2-(2,5-diisopropoxy-phenyl)-4,5-dihydro-imidazol-1-yl]-piperazin-1-yl-methanone hydrochloride. HR-MS (ES, m/z) calculated for $C_{32}H_{37}N_4O_3Cl_2[(M+H)^+]595.2237$, observed 595.2243.

EXAMPLE 29

1-[4,5-Bis-(4-chloro-phenyl)-2-(2-methoxy-5-morpholin-4-yl-methyl-phenyl)-4,5-dihydro-imidazol-1-yl]-2-methyl-propan-1-one

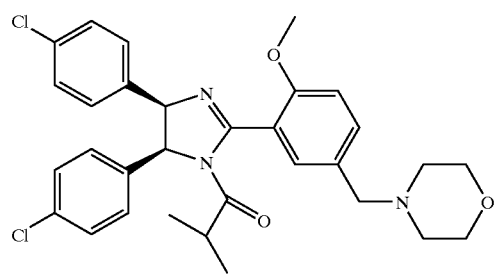

To a solution of 4-{3-[4,5-bis-(4-chloro-phenyl)-4,5-dihydro-1H-imidazol-2-yl]-4-methoxy-benzyl}-morpholine (100 mg, 0.20 mmol, as in the U.S. Provisional applications incorporated by reference herein, Example 31) in methylene chloride (10 mL) were sequentially added triethylamine (0.10 mL, 0.712 mmol) and isobutyryl chloride (42 μL, 0.392 mmol). The reaction mixture was stirred for 12 h. The solvents were removed under reduced pressure. Saturated sodium bicarbonate (2 mL) and methylene chloride (20 mL) were added and the layers were separated. The aqueous layer was extracted with methylene chloride (1×100 mL). The combined organic extracts were evaporated. Purification of the crude residue by Biotage flash chromatography eluting with 0–5% methanol in ethyl acetate gave 1-[4,5-bis-(4-chloro-phenyl)-2-(2-methoxy-5-morpholin-4-ylmethyl-phenyl)-4,5-dihydro-imidazol-1-yl]-2-methyl-propan-1-one. HR-MS (ES, m/z) calculated for $C_{31}H_{34}N_3O_3Cl_2[(M+H)^+]$566.1972, observed 566.1977.

EXAMPLE 30

In an analogous manner as described in example 29, the following compounds were prepared.

a) 1-[4,5-Bis-(4-chloro-phenyl)-2-(3-hydroxymethyl-5-methoxy-phenyl)-4,5-dihydro-imidazol-1-yl]-2-methyl-propan-1-one from {3-[4,5-bis-(4-chloro-phenyl)-4,5-dihydro-1H-imidazol-2-yl]-5-methoxy-phenyl}-methanol, as in the U.S. Provisional applications incorporated by reference herein, Example 33. HR-MS (ES, m/z) calculated for $C_{27}H_{27}N_2O_3Cl_2[(M+H)^+]$497.1393, observed 497.1402

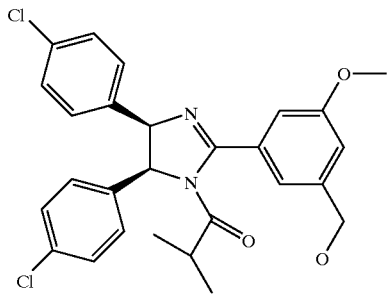

b) 1-[4,5-Bis-(4-chloro-phenyl)-2-(3-hydroxymethyl-5-methoxymethyl-phenyl)-4,5-dihydro-imidazol-1-yl]-ethanone from sodium {3-[4,5-bis-(4-chloro-phenyl)-4,5-dihydro-1H-imidazol-2-yl]-5-methoxymethyl-phenyl}-methanol, as in the U.S. Provisional applications incorporated by reference herein, Example 35. HR-MS (EI, m/z) calculated for $C_{26}H_{24}N_2O_3Cl_2$ (M+) 482.1164, observed 482.1161.

c) 1-[4,5-Bis-(4-chloro-phenyl)-2-(3-methoxy-5-methoxymethyl-phenyl)-4,5-dihydro-imidazol-1-yl]-2-methyl-propan-1-one from 4,5-bis-(4-chloro-phenyl)-2-(3-methoxy-5-methoxymethyl-phenyl)-4,5-dihydro-1H-imidazole, as in the U.S. Provisional applications incorporated by reference herein, Example 34, HR-MS (m/z) calculated for $C_{28}H_{29}N_2O_3Cl_2[(M+H)^+]$ 511.1550, observed 511.1556.

d) 3-[4,5-Bis-(4-chloro-phenyl)-1-isobutyryl-4,5-dihydro-1H-imidazol-2-yl]-5-methoxymethyl-benzoic acid from 3-[4,5-bis-(4-chloro-phenyl)-4,5-dihydro-1H-imidazol-2-yl]-5-methoxymethyl-benzoate, as in the U.S. Provisional applications incorporated by reference herein, Example 40, HR-MS (ES, m/z) calculated for $C_{28}H_{27}N_2O_4Cl_2[(M+H)^+]$525.1343, observed 525.1347.

e) 1-[4,5-Bis-(4-chloro-phenyl)-2-(5-ethoxymethyl-2,4-dimethoxy-phenyl)-4,5-dihydro-imidazol-1-yl]-2-methyl-propan-1-one from 4,5-Bis-(4-chloro-phenyl)-2-(5-ethoxymethyl-2,4-dimethoxy-phenyl)-4,5-dihydro-1H-imidazole as in the U.S. Provisional applications incorporated by reference herein, Example 32.

EXAMPLE 31

[1,5-Bis-(4-chloro-phenyl)-2-(2-ethoxy-6-methoxy-phenyl)-4,5-dihydro-imidazol-1-yl]-piperazin-1-yl-methanone

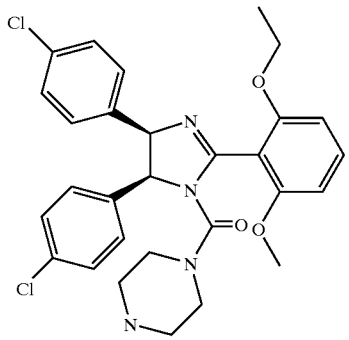

Phosgene (0.147 mL, 0.283 mmol, 1.93 M in toluene) was added to a stirred solution of 4,5-bis-(4-chloro-phenyl)-2-(2-ethoxy-6-methoxy-phenyl)-4,5-dihydro-1H-imidazole (described in previous patent) (25 mg, 0.0566 mmol) and triethylamine (39 μL, 0.283 mmol) in THF (2 mL) at 0° C. over a period of 5 min. The mixture was stirred for 3 h and evaporated. The residue was dissolved in methylene chloride (2 mL) and added dropwise to a stirred solution of piperazine (24 mg, 0.283 mmol) in methylene chloride (2 mL) at room temperature for 3 h. The mixture was diluted with aqueous sodium bicarbonate and extracted with methylene chloride. The organic extracts were washed with brine and dried over sodium sulfate. Evaporation of the solvents and chromatography of the residue over silica gel using 0–10% methanol in methylene chloride gave [4,5-bis-(4-chloro-phenyl)-2-(2-ethoxy-6-methoxy-phenyl)-4,5-dihydro-imidazol-1-yl]-piperazin-1-yl-methanone (19 mg, 61%). HR-MS (ES, m/z) calculated for $C_{29}H_{31}N_4O_3Cl_2[(M+H)^+]$553.1768, observed 553.1770.

EXAMPLE 32

[4,5-bis-(4-chloro-phenyl)-2-(5-ethoxymethyl-2,4-dimethoxy-phenyl)-4,5-dihydro-imidazol-1-yl]-piperazin-1-yl-methanone

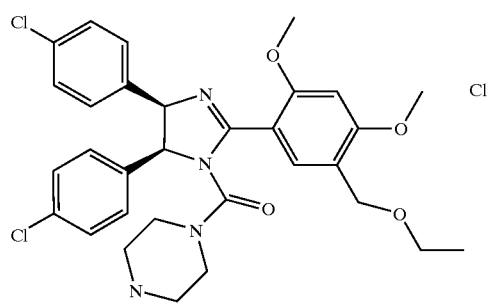

In a similar manner as described in example 31, the named compound was prepared from 4,5-bis-(4-chloro-phenyl)-2-(5-ethoxymethyl-2,4-dimethoxy-phenyl)-4,5-dihydro-1H-imidazole (described in previous patent). HR-MS (ES, m/z) calculated for $C_{31}H_{35}N_4O_4Cl_2[(M+H)^+]$ 597.2030, observed 597.2034.

EXAMPLE 33

[4,5-Bis-(4-chloro-phenyl)-2-(2-isopropoxy-4-methoxy-phenyl)-4,5-dihydro-imidazol-1-yl]-[4-(2-hydroxy-propyl)-piperazin-1-yl]-methanone

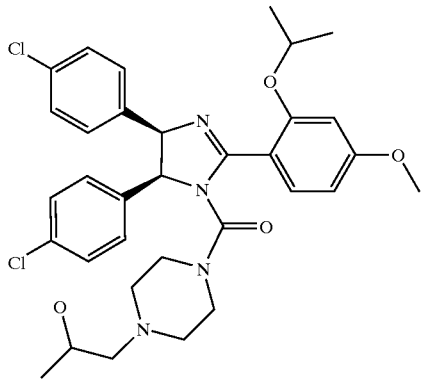

The compound was prepared by the treatment of [4,5-bis-(4-chloro-phenyl)-2-(2-isopropoxy-4-methoxy-phenyl)-4,5-dihydro-imidazol-1-yl]-piperazin-1-yl-methanone (example 10 g) with propylene oxide in methanol for 7 h at 45° C. in a sealed tube. HR-MS (ES, m/z) calculated for $C_{33}H_{38}N_4O_4Cl_2[(M+H)^+]$625.2343, observed 625.2350.

EXAMPLE 34

In a similar manner as described in examples 33, the following compounds were prepared.

a) [4,5-Bis-(4-chloro-phenyl)-2-(2-isopropoxy-4-methoxy-phenyl)-4,5-dihydro-imidazol-1-yl]-threo[4-(2-hydroxy-1-methyl-propyl)-piperazin-1-yl]-methanone. HR-MS (ES, m/z) calculated for $C_{34}H_{40}N_4O_4Cl_2[(M+H)^+]$639.2500, observed 639.2508.

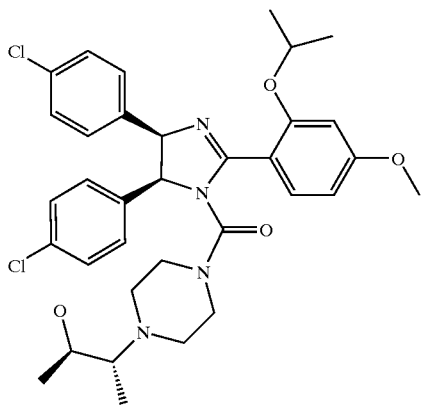

b) [4,5-Bis-(4-chloro-phenyl)-2-(2-isopropoxy-4-methoxy-phenyl)-4,5-dihydro-imidazol-1-yl]-erythro[4-(2-hydroxy-1-methyl-propyl)-piperazin-1-yl]-methanone. HR-MS (ES, m/z) calculated for $C_{34}H_{40}N_4O_4Cl_2[(M+H)^+]$639.2500, observed 639.2507.

EXAMPLE 35

1-{4-[4,5-Bis-(4-chloro-phenyl)-2-(2-isopropoxy-4-methoxy-phenyl)-4,5-dihydro-imidazole-1-carbonyl]-piperazin-1-yl}-propan-2-one

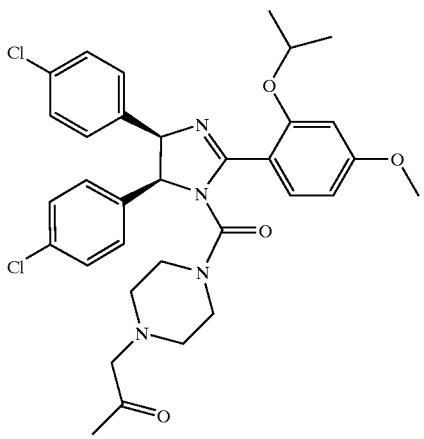

The compound was prepared by the treatment of [4,5-bis-(4-chloro-phenyl)-2-(2-isopropoxy-4-methoxy-phenyl)-4,5-dihydro-imidazol-1-yl]piperazin-1-yl-methanone (example 10 g) with chloroacetone and triethylamine at 40° C. overnight. HR-MS (ES, m/z) calculated for $C_{33}H_{36}N_4O_4Cl_2[(M+H)^+]$623.2187, observed 623.2194.

EXAMPLE 36

In a similar manner as described in examples 9, the following compounds were prepared.

a) [4,5-Bis-(4-chloro-phenyl)-2-(2-isopropoxy-4-methoxy-phenyl)-4,5-dihydro-imidazol-1-yl]-[1,4]diazepan-1-yl-methanone. HR-MS (ES, m/z) calculated for $C_{31}H_{34}N_4O_3Cl_2[(M+H)^+]$581.2081, observed 581.2086.

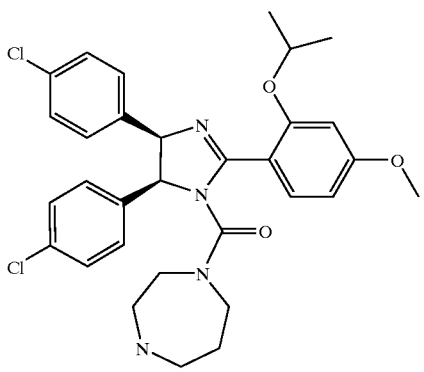

b) 4-[4,5-Bis-(4-chloro-phenyl)-2-(2-isopropoxy-4-methoxy-phenyl)-4,5-dihydro-imidazole-1-carbonyl]-1-methyl-piperazin-2-one. HR-MS (ES, m/z) calculated for $C_{31}H_{32}N_4O_4Cl_2[(M+H)^+]$595.1874, observed 595.1880.

c) 1-{4-[4,5-Bis-(4-chloro-phenyl)-2-(2-isopropoxy-4-methoxy-phenyl)-4,5-dihydro-imidazole-1-carbonyl]-piperazin-1-yl}-2-methyl-propan-1-one. HR-MS (ES, m/z) calculated for $C_{34}H_{38}N_4O_4Cl_2[(M+H)^+]$637.2343, observed 637.2348.

d) 4-[4,5-Bis-(4-chloro-phenyl)-2-(2-isopropoxy-4-methoxy-phenyl)-4,5-dihydro-imidazole-1-carbonyl]- piperazine-1-carbaldehyde. HR-MS (ES, m/z) calculated for $C_{31}H_{32}N_4O_4Cl_2[(M+H)^+]$595.1874, observed 595.1882.

EXAMPLE 37

In a similar manner as described in example 9, the following compounds were prepared:

a) 4-{4,5-Bis-(4-chloro-phenyl)-2-[4-methoxy-2-(2,2,2-trifluoro-ethoxy)-phenyl]-4,5-dihydro-imidazole-1-carbonyl}-piperazin-2-one

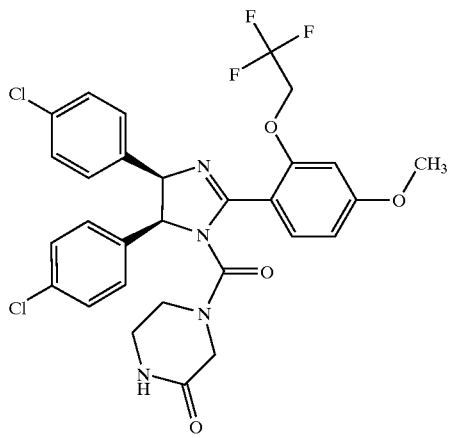

The compound was prepared from 4,5-bis-(4-chloro-phenyl)-2-[4-methoxy-2-(2,2,2-trifluoro-ethoxy)-phenyl]-4,5-dihydro-1H-imidazole, as in the U.S. Provisional applications incorporated by reference herein, example 47a. HR-MS (ES, m/z) calculated for $C_{29}H_{25}N_4O_4F_3Cl_2[(M+H)^+]$621.1278, observed 621.1285.

b) 4-{4,5-Bis-(4-bromo-phenyl)-2-[4-methoxy-2-(2,2,2-trifluoro-ethoxy)-phenyl]-4,5-dihydro-imidazole-1-carbonyl}-piperazin-2-one from 4,5-bis-(4-bromo-phenyl)-2-[4-methoxy-2-(2,2,2-trifluoro-ethoxy)-phenyl]-4,5-dihydro-1H-imidazole, as in the U.S. Provisional applications incorporated by reference herein, example 47b. HR-MS (ES, m/z) calculated for $C_{29}H_{25}N_4O_4F_3Br_2[(M+H)^+]$709.0268, observed 709.0280.

c) [4,5-Bis-(4-ethynyl-phenyl)-2-(2-isopropoxy-4-methoxy-phenyl)-4,5-dihydro-imidazol-1-yl]-(4-pyrrolidin-1-yl-piperidin-1-yl)-methanone from 4,5-bis-(4-ethynyl-phenyl)-2-(2-isopropoxy-4-methoxy-phenyl)-4,5-dihydro-1H-imidazole, as in the U.S. Provisional applications incorporated by reference herein, example 47d. HR-MS (ES, m/z) calculated for $C_{29}H_{25}N_4O_4F_3Br_2[(M+H)^+]$615.3330, observed 615.3319.

d) 1-{4-[2-(5-Chloro-2-isopropoxy-phenyl)-4,5-bis-(4-chloro-phenyl)-4,5-dihydro-imidazole-1-carbonyl]-piperazin-1-yl}-ethanone from 2-(5-Chloro-2-isopropoxy-phenyl)-4,5-bis-(4-chloro-phenyl)-4,5-dihydro-1H-imidazole, as in the U.S. Provisional applications incorporated by reference herein, example 46. HR-MS (ES, m/z) calculated for $C_{31}H_{31}N_3O_3Cl_3[(M+H)^+]$613.1535, observed 613.1543.

EXAMPLE 38

In a similar manner as described in examples 3, the following compounds were prepared from 4-(4-chloro-phenyl)-5-(4-ethynyl-phenyl)-2-(2-isopropoxy-4-methoxy-phenyl)-4,5-dihydro-1H-imidazole, as in the U.S. Provisional applications incorporated by reference herein, example 47e:

a) [5-(4-Chloro-phenyl)-4-(4-ethynyl-phenyl)-2-(2-isopropoxy-4-methoxy-phenyl)-4,5-dihydro-imidazol-1-yl]-(4-pyrrolidin-1-yl)-methanone. HR-MS (ES, m/z) calculated for $C_{37}H_{41}N_4O_3Cl[(M+H)^+]$625.2940, observed 625.2943.

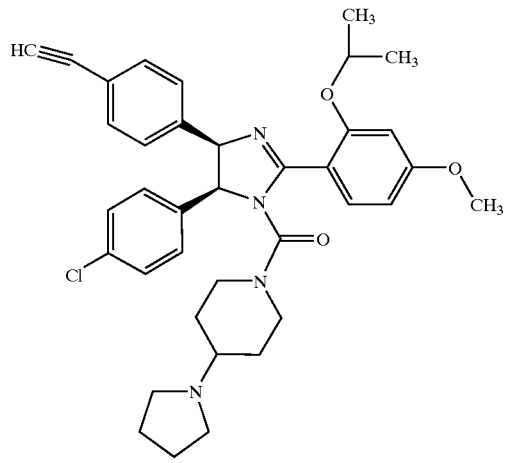

b) 4-{4,5-Bis-(4-bromo-phenyl)-2-[4-methoxy-2-(2,2,2-trifluoro-ethoxy)-phenyl]-4,5-dihydro-imidazole-1-carbonyl}-piperazin-2-one[4-(4-Chloro-phenyl)-5-(4-ethynyl-phenyl)-2-(2-isopropoxy-4-methoxy-phenyl)-4,5-dihydro-imidazol-1-yl]-(4-pyrrolidin-1-yl-piperidin-1-yl)-methanone. HR-MS (ES, m/z) calculated for $C_{37}H_{41}N_4O_3Cl[(M+H)^+]$625.2940, observed 625.2943.

EXAMPLE 39

In Vitro Activity Assay

The ability of the compounds to inhibit the interaction between p53 and MDM2 proteins was measured by an ELISA (Enzyme-Linked Immuno Sorbent Assay) in which recombinant GST-tagged MDM2 binds to a peptide that resembles the MDM2-interacting region of p53 (Böttger et al., J. Mol. Bio. 1997, Vol. 269, pgs. 744–756). This peptide is immobilized to the surface of a 96 well plate via N-terminal biotin which binds to streptavidin-coated wells. MDM2 is added to each well in the presence of anti-MDM2 mouse monoclonal antibody (SMP-14, Santa Cruz Biotech). After removal of the unbound MDM2 protein, a peroxydase-linked secondary antibody (anti-mouse IgG, Roche Molecular Biochemicals) and the amount of peptide-bound MDM2 is determined colorimetrically by the addition of a peroxydase substrate (MTB Microwell Peroxydase Substrate System, Kirkegaard & Perry Labs).

Test plates were prepared by coating with streptavidin (5 mg/ml in PBS) for 2 hours followed by a PBS (phosphate-buffered saline) wash and overnight blocking with 150 μl of blocking buffer containing 2 mg/ml bovine serum albumin (Sigma) and 0.05% Tween 20 (Sigma) in PBS at 4° C. Biotinylated peptide (1 μM) is added to each well in 50 μl of blocking buffer and washed extensively after 1 h incubation. Test compounds were diluted in a separate 96 well plate and added in triplicate to a compound incubation plate containing a mix of the MDM2 protein and anti-MDM2 antibody. After 20 min incubation, the content of the plate is transferred to the test plate and incubated for an additional 1 hour. The secondary anti-mouse IgG antibody is added to the test plate preceeded and followed by a triple wash with 0.05% Tween 20 in PBS. Finally, peroxydase substrate is added to each well and the absorption was read using a plate reader (MR7000, Dynatech) at 450 nm. The inhibitory activity of the test compounds was measured as a percentage of the bound MDM2 in treated vs. untreated wells and $IC_{50}$ was calculated.

What is claimed is:

1. At least one compound selected from a compound of formula I

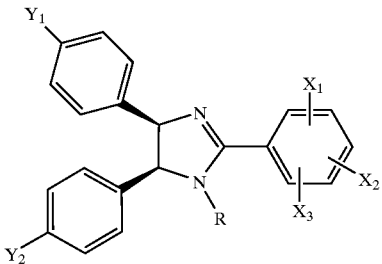

or pharmaceutically acceptable salts or esters thereof, wherein

R is —C=OR1, wherein R1 is selected from C1–C4 alkyl, —C=CHCOOH, —NHCH$_2$CH$_2$R$_2$, —N(CH$_2$CH$_2$OH)CH$_2$CH$_2$OH, —N(CH$_3$)CH$_2$CH$_2$NCH$_3$, —N(CH$_3$)CH$_2$CH$_2$N(CH$_3$)CH$_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, —C=O—R5, —OH, lower alkyl substituted with hydroxy, lower alkyl substituted with —NH$_2$, N-lower alkyl, —SO$_2$CH$_3$, =O, —CH$_2$C=OCH$_3$, and 5- and 6-membered saturated rings containing at least one hetero atom selected from S, N and O, wherein R5 is selected from H, lower alkyl, —NH$_2$, —N-lower alkyl, lower alkyl substituted with hydroxy, and lower alkyl substituted with NH$_2$, wherein R2 is selected from —N(CH$_3$)CH$_3$, —NHCH$_2$CH$_2$NH$_2$, —NH$_2$, morpholinyl and piperazinyl, $X_1$, $X_2$ and $X_3$ are independently selected from —OH, C1–C2 alkyl, C1–C5 alkoxy, —Cl, —Br, —F, —CH$_2$OCH$_3$, and —CH$_2$OCH$_2$CH$_3$, or one of $X_1$, $X_2$ or $X_3$ is H and the other two are independently selected from hydroxy, lower alkyl, lower alkoxy, Cl, Br, F, —CF$_3$, —CH$_2$OCH$_3$, —CH$_2$OCH$_2$CH$_3$, —OCH$_2$CH$_2$R$^3$, —OCH$_2$CF$_3$, and —OR4, or one of $X_1$, $X_2$ or $X_3$ is H and the other two taken together with the two carbon atoms and the bonds between them from the benzene ring to which they are substituted form a 5- or 6-membered saturated ring that contains at least one hetero atom selected from S, N, and O, wherein R3 is selected from —F, —OCH$_3$, —N(CH$_3$)CH$_3$, unsaturated 5- and 6-membered rings containing at least one hetero atom wherein the hetero atom is selected from S, N and O, wherein R4 is a 3- to 5-membered saturated ring and $Y_1$ and $Y_2$ are each independently selected from —Cl, —Br, —NO$_2$, —C≡N, and —C≡CH.

2. The compound according to claim 1, wherein $Y_1$ and $Y_2$ are each independently selected from —Cl and —Br.

3. The compound according to claim 1, wherein R1 is selected from morpholinyl, piperazinyl, piperidinyl, cyclopentyl, cyclohexyl, thiophenyl, isoxazolyl, and furanyl, piperazinyl substituted with at least one group selected from C1–C3 alkyl, —C1–C2 alkoxy, —C=OCH$_3$, —SO$_2$CH$_3$, —C=O, —OH, —CH$_2$NH$_2$, —C=OCH$_2$NH$_2$, —C=OCH$_2$OH, —C=OC(OH)CH$_2$OH, —CH$_2$C(OH)—CH$_2$OH, —C=ON(CH$_2$—)$_2$, —C=ONH2, and —C=ON(CH$_3$)CH$_3$, —C=OCH(CH$_3$)$_2$, —CH$_2$C=OCH$_3$, —CH$_2$CH(OH)CH$_3$, —CH(CH$_3$)CH(OH)CH$_3$ and piperidinyl substituted with at least one group selected from C1–C3 alkyl, —C1–C2 alkoxy, —C=OCH$_3$, —SO$_2$CH$_3$, —C=O, —OH, —CH$_2$NH$_2$, —C=OCH$_2$NH$_2$, —C=OCH$_2$OH, —C=OC(OH)CH$_2$OH, —CH$_2$C(OH)CH$_2$OH, —C=ON(CH$_2$)$_2$, —C=ONH$_2$, and —C=ON(CH$_3$)CH$_3$, —N(CH$_3$)CH$_3$, pyrrolidinyl and piperidinyl.

4. The compound according to claim 1, wherein where one of $X_1$, $X_2$ and $X_3$ is H, the remaining two are independently selected from hydroxy, lower alkoxy which is C1–C5 alkoxy, Cl, Br, F, —CH$_2$OCH$_3$, —CH$_2$OCH$_2$CH$_3$, lower alkyl selected from C1 and C2 alkyl, or one of $X_1$, $X_2$ or $X_3$ is H and the other two taken together with the two carbon atoms and the bonds between them from the benzene ring to which they are substituted form a 5-membered saturated ring that contains at least one hetero atom selected from S, N and O.

5. The compound according to claim 4, wherein where one of $X_1$, $X_2$ or $X_3$ is H, the other two are independently selected from —OCH$_3$ and —CH$_2$OCH$_2$CH$_3$.

6. The compound according to claim 4, wherein when one of $X_1$, $X_2$ or $X_3$ is H, and one or both of the other two is lower alkoxy selected from —O—C1 alkyl, —O—C2 alkyl and —O—C3 alkyl.

7. The compound according to claim 1, wherein when one of $X_1$, $X_2$ or $X_3$ is H, the other two are independently selected from —OCH$_2$CH$_2$R3 and —OR4, wherein R3 is selected from —F, —OCH$_3$, —N(CH$_3$)CH$_3$, unsaturated 5-membered rings containing at least one hetero atom wherein the hetero atom is selected from S, N and O, and wherein R4 is cyclopentyl.

8. The compound according to claim 7, wherein R3 is imidazolyl.

9. The compound according to claim 1, wherein $X_3$ is H and $X_1$ and $X_2$ together with the two carbon atoms and the bonds between them from the benzene ring to they are substituted form a 6-membered saturated ring that contains one hetero atom which is O.

10. The compound according to claim 1, wherein when one of the groups $X_1$, $X_2$ or $X_3$ is H at meta position, the group at ortho position is selected from lower alkoxy and —OCH$_2$CF$_3$, and the group at para position is lower alkoxy.

11. The compound according to claim 10, wherein the $X_1$, $X_2$ or $X_3$ group at ortho position is selected from ethoxy, isopropoxy and —OCH$_2$CF$_3$, and the group at para position is selected from methoxy and ethoxy.

12. The compound according to claim 11, wherein R1 is selected from piperazinyl and substituted piperazinyl.

13. The compound according to claim 1, wherein where one of the groups $X_1$, $X_2$ or $X_3$ is H at meta position, the group at the ortho position is lower alkoxy and the group at the para position is —Cl, —Br or —F, or where one of the groups $X_1$, $X_2$ or $X_3$ is H at para position, the groups at ortho position is lower alkoxy and the group at meta position is —Cl, —Br or —F.

14. At least one compound selected from a compound of formula II

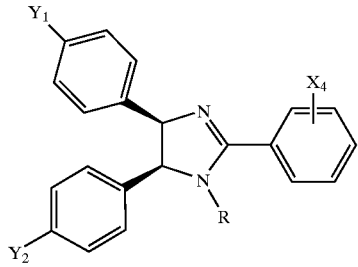

or pharmaceutically acceptable salts or esters thereof, wherein

R is —C=OR1,
wherein R1 is selected from C1–C4 alkyl, saturated 5- and 6-membered rings, saturated 5- and 6-membered rings containing at least one hetero atom wherein the hetero atom is selected from S, N and O and being optionally substituted with a group selected from C1–C2 alkyl, C1–C3 alcohol, —N(CH$_3$)CH$_3$, —C=OCH$_3$, and 5- and 6-membered rings containing at least one hetero atom wherein the hetero atom is selected from S, N, and O, $X_4$ is selected from C1–C2 alkyl, lower alkoxy, fluoroethoxy, —Cl, —Br, —F, —OCH$_2$C=OOQ, —O-lower alkyl, —OCH$_2$-cyclopropyl, —CH$_2$OCH$_2$-phenyl, saturated and unsaturated 5- and 6-membered rings, saturated and unsaturated 5- and 6-membered rings containing at least one hetero atom wherein the hetero atom is selected from S, N and O, wherein Q is selected from H, and lower alkyl, $Y_1$ and $Y_2$ are independently selected from —Cl, —Br, —NO$_2$, —C≡N and —C≡CH, with the proviso that where $Y_1$ and $Y_2$ are both —Cl, and R1 is —CH$_3$, then $X_4$ is not —Cl.

15. The compound according to claim 14, wherein $X_4$ is selected from —CH$_3$, C1–C5 alkoxy, —Cl, —Br, —OCH$_2$C=OOQ, phenyl and pyrrolidinyl, wherein Q is H or —CH$_2$CH$_3$.

16. The compound according to claim 15, wherein $X_4$ is selected from —CH$_3$, C1–C5 alkoxy, —OCH$_2$C=OOQ, phenyl and pyrrolidinyl, wherein Q is H or —CH$_2$CH$_3$.

17. The compound according to claim 14, wherein R1 is selected from —CH(CH$_3$)CH$_3$, piperazinyl, piperazinyl substituted with a group selected from —CH$_3$, —CH$_2$CH$_2$OH, and —C=OCH$_3$, piperidinyl, and piperidinyl substituted with a group selected from -pyrrolidinyl, piperidinyl, and —N(CH$_3$)CH$_3$.

18. The compound according to claim 14, wherein lower alkyl is selected from C1 alkyl, C2 alkyl and C3 alkyl.

19. The compound according to claim 14, wherein $Y_1$ and $Y_2$ are independently selected from —Cl and —Br.

20. The compound according to claim 19, wherein $X_4$ is lower alkoxy at ortho position.

21. The compound according to claim 20, wherein $X_4$ is selected from ethoxy, isopropoxy and 2-fluoroethoxy.

22. The compound according to claim 21, wherein R1 is selected from piperazinyl and substituted piperazinyl.

23. The compound according to claim 1, selected from the group of:

1-[4,5-Bis-(4-chloro-phenyl)-2-(2,4-dimethoxy-phenyl)-4,5-dihydro-imidazol-1-yl]-2-methyl-propan-1-one;

1-[4,5-Bis-(4-chloro-phenyl)-2-(2,4-dimethoxy-phenyl)-4,5-dihydro-imidazol-1-yl]ethanone;

1-[4,5-Bis-(4-chloro-phenyl)-2-(2,4-dimethoxy-phenyl)-4,5-dihydro-imidazol-1-yl]-2,2-dimethyl-propan-1-one;

[4,5-Bis-(4-chloro-phenyl)-2-(2,4-dimethoxy-phenyl)-4,5-dihydro-imidazol-1-yl]-cyclopentyl-methanone;

[4,5-Bis-(4-chloro-phenyl)-2-(2,4-dimethoxy-phenyl)-4,5-dihydro-imidazol-1-yl]-cyclohexyl-methanone;

[4,5-Bis-(4-chloro-phenyl)-2-(2,4-dimethoxy-phenyl)-4,5-dihydro-imidazol-1-yl]-thiophen-2-yl-methanone;

[4,5-Bis-(4-chloro-phenyl)-2-(2,4-dimethoxy-phenyl)-4,5-dihydro-imidazol-1-yl]-isoxazol-5-yl-methanone;

[4,5-Bis-(4-chloro-phenyl)-2-(2,4-dimethoxy-phenyl)-4,5-dihydro-imidazol-1-yl]-furan-2-yl-methanone;

1-[4,5-Bis-(4-chloro-phenyl)-2-(2,3-dimethoxy-phenyl)-4,5-dihydro-imidazol-1-yl]-2-methyl-propan-1-one; and

[4,5-Bis-(4-chloro-phenyl)-2-(2,4-dimethoxy-phenyl)-4,5-dihydro-imidazol-1-yl]-(4-methyl-piperazin-1-yl)-methanone.

24. The compound according to claim 1, selected from:

1-{4-[4,5-Bis-(4-bromo-phenyl)-2-(2-isopropoxy-4-methoxy-phenyl)-4,5-dihydro-imidazole-1-carbonyl]-piperazin-1-yl}-ethanone;

[4,5-Bis-(4-bromo-phenyl)-2-(2-isopropoxy-4-methoxy-phenyl)-4,5-dihydro-imidazol-1-yl]-(4-methanesulfonyl-piperazin-1-yl)-methanone;

[4,5-Bis-(4-bromo-phenyl)-2-(2-isopropoxy-4-methoxy-phenyl)-4,5-dihydro-imidazol-1-yl]-(4-methyl-piperazin-1-yl)-methanone;

[4,5-Bis-(4-bromo-phenyl)-2-(2-isopropoxy-4-methoxy-phenyl)-4,5-dihydro-imidazol-1-yl]-morpholin-4-yl-methanone;

[1,4']Bipiperidinyl-1'-yl-[4,5-bis-(4-bromo-phenyl)-2-(2-isopropoxy-4-methoxy-phenyl)-4,5-dihydro-imidazol-1-yl]-methanone;

[4,5-Bis-(4-bromo-phenyl)-2-(2-isopropoxy-4-methoxy-phenyl)-4,5-dihydro-imidazol-1-yl]-(4-ethyl-piperazin-1-yl)-methanone;

4-[4,5-Bis-(4-bromo-phenyl)-2-(2-isopropoxy-4-methoxy-phenyl)-4,5-dihydro-imidazole-1-carbonyl]-piperazin-2-one;

[4,5-Bis-(4-cyano-phenyl)-2-(2-isopropoxy-4-methoxy-phenyl)-4,5-dihydro-imidazol-1-yl]-piperazin-1-yl-methanone;

1-(4-{4,5-Bis-(4-chloro-phenyl)-2-[4-methoxy-2-(2-methoxy-ethoxy)-phenyl]-4,5-dihydro-imidazole-1-carbonyl}-piperazin-1-yl)-ethanone; and 1-(4-{4,5-Bis-(4-chloro-phenyl)-2-[2-(2-fluoro-ethoxy)-4-methoxy-phenyl]-4,5-dihydro-imidazole-1-carbonyl}-piperazin-1-yl)-ethanone.

25. The compound according to claim 1, selected from:

[4,5-Bis-(4-chloro-phenyl)-2-(2-ethoxy-4-fluoro-phenyl)-4,5-dihydro-imidazol-1-yl]-(4-pyrrolidin-1-yl-piperazin-1-yl)-methanone;

[4,5-Bis-(4-chloro-phenyl)-2-(2-ethoxy-4-fluoro-phenyl)-4,5-dihydro-imidazol-1-yl]-(4-dimethylamino-piperazin-1-yl)-methanone;

[4,5-Bis-(4-chloro-phenyl)-2-(2-ethoxy-4-fluoro-phenyl)-4,5-dihydro-imidazol-1-yl]-piperazin-1-yl)-methanone;

[4,5-Bis-(4-chloro-phenyl)-2-(4-fluoro-2-isopropoxy-phenyl)-4,5-dihydro-imidazol-1-yl]-(4-pyrrolidin-1-yl-piperazin-1-yl)-methanone;

[4,5-Bis-(4-chloro-phenyl)-2-(4-fluoro-2-isopropoxy-phenyl)-4,5-dihydro-imidazol-1-yl]-(4-dimethylamino-piperazin-1-yl)-methanone;

[4,5-Bis-(4-chloro-phenyl)-2-(4-fluoro-2-isopropoxy-phenyl)-4,5-dihydro-imidazol-1-yl]-(4-methyl-piperazin-1-yl)-methanone;

[4,5-Bis-(4-chloro-phenyl)-2-(4-fluoro-2-isopropoxy-phenyl)-4,5-dihydro-imidazol-1-yl]-piperazin-1-yl)-methanone;

[4,5-Bis-(4-chloro-phenyl)-2-(4-fluoro-2-isopropoxy-phenyl)-4,5-dihydro-imidazol-1-yl]-(4-methanesulfonyl-piperazin-1-yl)-methanone;

4-[4,5-Bis-(4-chloro-phenyl)-2-(4-fluoro-2-isopropoxy-phenyl)-4,5-dihydro-imidazol-1-carbonyl]-piperazin-2-one; and

[4,5-Bis-(4-chloro-phenyl)-2-chroman-8-yl-4,5-dihydro-imidazol-1-yl]-piperazin-1-yl-methanone.

26. The compound according to claim 1, selected from the group of:

[4,5-Bis-(4-chloro-phenyl)-2-(2-isopropoxy-4-methoxy-phenyl)-4,5-dihydro-imidazol-1-yl]-[4-(2-hydroxy-propyl)-piperazin-1-yl]-methanone;

[4,5-Bis-(4-chloro-phenyl)-2-(2-isopropoxy-4-methoxy-phenyl)-4,5-dihydro-imidazol-1-yl]-threo[4-(2-hydroxy-1-methyl-propyl)-piperazin-1-yl]-methanone;

[4,5-Bis-(4-chloro-phenyl)-2-(2-isopropoxy-4-methoxy-phenyl)-4,5-dihydro-imidazol-1-yl]-erythro[4-(2-hydroxy-1-methyl-propyl)-piperazin-1-yl]-methanone;

1-{4-[4,5-Bis-(4-chloro-phenyl)-2-(2-isopropoxy-4-methoxy-phenyl)-4,5-dihydro-imidazole-1-carbonyl]-piperazin-1-yl}-propan-2-one;

[4,5-Bis-(4-chloro-phenyl)-2-(2-isopropoxy-4-methoxy-phenyl)-4,5-dihydro-imidazol-1-yl]-[1,4]diazepan-1-yl-methanone;

4-[4,5-Bis-(4-chloro-phenyl)-2-(2-isopropoxy-4-methoxy-phenyl)-4,5-dihydro-imidazole-1-carbonyl]-1-methyl-piperazin-2-one;

1-{4-[4,5-Bis-(4-chloro-phenyl)-2-(2-isopropoxy-4-methoxy-phenyl)-4,5-dihydro-imidazole-1-carbonyl]-piperazin-1-yl}-2-methyl-propan-1-one;

4-[4,5-Bis-(4-chloro-phenyl)-2-(2-isopropoxy-4-methoxy-phenyl)-4,5-dihydro-imidazole-1-carbonyl]-piperazin-1-carbaldehyde;

4-{4,5-Bis-(4-chloro-phenyl)-2-[4-methoxy-2-(2,2,2-trifluoro-ethoxy)-phenyl]-4,5-dihydro-imidazole-1-carbonyl}-piperazin-2-one;

4-{4,5-Bis-(4-bromo-phenyl)-2-[4-methoxy-2-(2,2,2-trifluoro-ethoxy)-phenyl]-4,5-dihydro-imidazole-1-carbonyl}-piperazin-2-one;

[4,5-Bis-(4-ethynyl-phenyl)-2-(2-isopropoxy-4-methoxy-phenyl)-4,5-dihydro-imidazol-1-yl]-(4-pyrrolidin-1-yl-piperidin-1-yl)-methanone;

1-{4-2-(5-Chloro-2-isopropoxy-phenyl)-4,5-bis-(4-chloro-phenyl)-4,5-dihydro-imidazole-1-carbonyl]-piperazin-1-yl}-ethanone; and

[5-(4-Chloro-phenyl)-4-(4-ethynyl-phenyl)-2-(2-isopropoxy-4-methoxy-phenyl)-4,5-dihydro-imidazole-1-yl]-(4-pyrrolidin-1-yl-piperidin-1-yl)-methanone.

27. The compound according to claim 14, selected from the group of:

1-[4,5-Bis-(4-chloro-phenyl)-2-(2-methoxy-phenyl)-4,5-dihydro-imidazol-1-yl]-2-methyl-propan-1-one;

1-[4,5-Bis-(4-chloro-phenyl)-2-p-tolyl-4,5-dihydro-imidazol-1-yl]-ethanone;

{4-[4,5-Bis-(4-chloro-phenyl)-1-isobutyryl-4,5-dihydro-1H-imidazol-2-yl]-phenoxy}-acetic acid ethyl ester;

{4-[4,5-Bis-(4-chloro-phenyl)-1-isobutyryl-4,5-dihydro-1H-imidazol-2-yl]-phenoxy}-acetic acid;

2-Methyl-1-[2,4,5-tris-(4-chloro-phenyl)-4,5-dihydro-imidazol-1-yl]-propan-1-one;

1-[4,5-Bis-(4-chloro-phenyl)-2-(4-methoxy-phenyl)-4,5-dihydro-imidazol-1-yl]-ethanone;

[2-(2-Chloro-phenyl)-4,5-bis-(4-chloro-phenyl)-4,5-dihydro-imidazol-1-yl]-piperazin-1-yl-methanone;

[2-(3-Bromo-phenyl)-4,5-bis-(4-chloro-phenyl)-4,5-dihydro-imidazol-1-yl]-piperazin-1-yl-methanone;

[2-Biphenyl-3-yl-4,5-bis-(4-chloro-phenyl)-4,5-dihydro-imidazol-1-yl]-(4-methyl-piperazin-1-yl-methanone; and

[4,5-Bis-(4-chloro-phenyl)-2-(3-pyrrolidin-1-yl-phenyl)-4,5-dihydro-imidazol-1-yl]-piperazin-1-yl-methanone.

28. The compound according to claim 1, selected from the group of:

[4,5-Bis-(4-chloro-phenyl)-2-(2,4-dimethoxy-phenyl)-4,5-dihydro-imidazol-1-yl]-piperazin-1-yl-methanone;

[4,5-Bis-(4-chloro-phenyl)-2-(2-fluoro-6-methoxy-phenyl)-4,5-dihydro-imidazol-1-yl]-[4-(2-hydroxy-ethyl)-piperazin-1-yl]-methanone;

1-{4-[4,5-Bis-(4-bromo-phenyl)-2-(2,4-dimethoxy-phenyl)-4,5-dihydro-imidazole-1-carbonyl]-piperazin-1-yl}-ethanone;

[4,5-Bis-(4-bromo-phenyl)-2-(2,4-dimethoxy-phenyl)-4,5-dihydro-imidazol-1-yl]-[4-(2-hydroxy-ethyl)-piperazin-1-yl]-methanone;

[4,5-Bis-(4-chloro-phenyl)-2-(2-isopropoxy-4-methoxy-phenyl)-4,5-dihydro-imidazol-1-yl]-[4-(2-hydroxy-ethyl)-piperazin-1-yl]-methanone hydrochloride;

[4,5-Bis-(4-chloro-phenyl)-2-(2-ethoxy-4-methoxy-phenyl)-4,5-dihydro-imidazol-1-yl]-(4-methanesulfonyl-piperazin-1-yl)-methanone;

[4,5-Bis-(4-chloro-phenyl)-2-(2-ethoxy-4-methoxy-phenyl)-4,5-dihydro-imidazol-1-yl]-[4-(2-hydroxy-ethyl)-piperazin-1-yl]-methanone;

[4,5-Bis-(4-chloro-phenyl)-2-(2-ethoxy-4-methoxy-phenyl)-4,5-dihydro-imidazol-1-yl]-morpholin-4-yl-methanone;

[4,5-Bis-(4-chloro-phenyl)-2-(2-ethoxy-4-methoxy-phenyl)-4,5-dihydro-imidazol-1-yl]-(4-methyl-piperazin-1-yl)-methanone; and 1-{4-[4,5-Bis-(4-chloro-phenyl)-2-(2-ethoxy-4-methoxy-phenyl)-4,5-dihydro-imidazole-1-carbonyl]-piperazin-1-yl}-ethanone.

29. The compound according to claim 1, selected from the group of:

4-[4,5-Bis-(4-chloro-phenyl)-2-(2-ethoxy-4-methoxy-phenyl)-4,5-dihydro-imidazole-1-carbonyl]-piperazin-2-one;

[4,5-Bis-(4-chloro-phenyl)-2-(2-isopropoxy-4-methoxy-phenyl)-4,5-dihydro-imidazol-1-yl]-piperazin-1-yl-methanone;

1-{4-[4,5-Bis-(4-chloro-phenyl)-2-(2-isopropoxy-4-methoxy-phenyl)-4,5-dihydro-imidazole-1-carbonyl]-piperazin-1-yl}-ethanone;

[4,5-Bis-(4-chloro-phenyl)-2-(2-isopropoxy-4-methoxy-phenyl)-4,5-dihydro-imidazole-1-yl]-(4-methanesulfonyl-piperazin-1-yl)-methanone;

[4,5-Bis-(4-chloro-phenyl)-2-(2-isopropoxy-4-methoxy-phenyl)-4,5-dihydro-imidazol-1-yl]-(2,5-dimethyl-piperazin-1-yl)-methanone;

4,5-Bis-(4-chloro-phenyl)-2-(2-isopropoxy-4-methoxy-phenyl)-4,5-dihydro-imidazole-1-carboxylic acid bis-(2-hydroxy-ethyl)-amide;

[4,5-Bis-(4-chloro-phenyl)-2-(2-isopropoxy-4-methoxy-phenyl)-4,5-dihydro-imidazol-1-yl]-(4-ethyl-piperazin-1-yl)-methanone;

[1,4']Bipiperidinyl-1'-yl-[4,5-bis-(4-chloro-phenyl)-2-(2-isopropoxy-4-methoxy-phenyl)-4,5-dihydro-imidazol-1-yl]-methanone;

[4,5-Bis-(4-chloro-phenyl)-2-(2-isopropoxy-4-methoxy-phenyl)-4,5-dihydro-imidazol-1-yl]-(4-pyrrolidin-1-yl-piperidin-1-yl)-methanone; and

[4,5-Bis-(4-chloro-phenyl)-2-(2-isopropoxy-4-methoxy-phenyl)-4,5-dihydro-imidazol-1-yl]-(4-dimethylamino-piperidin-1-yl)-methanone.

30. The compound according to claim 1, selected from the group of:

[4,5-Bis-(4-chloro-phenyl)-2-(2-isopropoxy-4-methoxy-phenyl)-4,5-dihydro-imidazol-1-yl]-morpholin-4-yl-methanone;

[4,5-Bis-(4-chloro-phenyl)-2-(2-isopropoxy-4-methoxy-phenyl)-4,5-dihydro-imidazol-1-yl]-(4-isopropyl-piperazin-1-yl)-methanone;

4-[4,5-Bis-(4-chloro-phenyl)-2-(2-isopropoxy-4-methoxy-phenyl)-4,5-dihydro-imidazole-1-carbonyl]-piperazin-2-one;

[4,5-Bis-(4-chloro-phenyl)-2-(2-isopropoxy-4-methoxy-phenyl)-4,5-dihydro-imidazol-1-yl]-(4-hydroxymethyl-piperidin-1-yl)-methanone;

[4,5-Bis-(4-chloro-phenyl)-2-(2-isopropoxy-4-methoxy-phenyl)-4,5-dihydro-imidazol-1-yl]-[4-(hydroxy-ethyl)-piperidin-1-yl]-methanone;

[4,5-Bis-(4-chloro-phenyl)-2-(2-isopropoxy-4-methoxy-phenyl)-4,5-dihydro-imidazol-1-yl]-(3-methyl-piperazin-1-yl)-methanone;

1-{4-[4,5-Bis-(4-chloro-phenyl)-2-(2-isopropoxy-4-methoxy-phenyl)-4,5-dihydro-imidazole-1-carbonyl]-2-methyl-piperazin-1-yl}-ethanone;

[4,5-Bis-(4-chloro-phenyl)-2-(2-isopropoxy-4-methoxy-phenyl)-4,5-dihydro-imidazol-1-yl]-(4-methanesulfonyl-3-methyl-piperazin-1-yl)-methanone;

[4,5-Bis-(4-chloro-phenyl)-2-(2-isopropoxy-4-methoxy-phenyl)-4,5-dihydro-imidazol-1-yl]-(4-hydroxy-piperidin-1-yl)-methanone; and (4-Aminomethyl-piperidin-1-yl)-[4,5-bis-(4-chloro-phenyl)-2-(2-isopropoxy-4-methoxy-phenyl)-4,5-dihydro-imidazol-1-yl]-methanone.

31. The compound according to claim 1, selected from the group of:

[4,5-Bis-(4-bromo-phenyl)-2-(2-ethoxy-4-methoxy-phenyl)-4,5-dihydro-imidazol-1-yl]-[4-(2-hydroxy-ethyl)-piperazin-1-yl]-methanone;

[4,5-Bis-(4-bromo-phenyl)-2-(2-ethoxy-4-methoxy-phenyl)-4,5-dihydro-imidazol-1-yl]-piperazin-1-yl-methanone;

[4,5-Bis-(4-bromo-phenyl)-2-(2-ethoxy-4-methoxy-phenyl)-4,5-dihydro-imidazol-1-yl]-(4-methanesulfonyl-piperazin-1-yl)-methanone;

1-{4-[4,5-Bis-(4-bromo-phenyl)-2-(2-ethoxy-4-methoxy-phenyl)-4,5-dihydro-imidazole-1-carbonyl]-piperazin-1-yl}-ethanone;

[4,5-Bis-(4-bromo-phenyl)-2-(2-ethoxy-4-methoxy-phenyl)-4,5-dihydro-imidazol-1-yl]-(4-methyl-piperazin-1-yl)-methanone;

4-[4,5-Bis-(4-bromo-phenyl)-2-(2-ethoxy-4-methoxy-phenyl)-4,5-dihydro-imidazole-1-carbonyl]-piperazine-1-carbaldehyde;

[4,5-Bis-(4-bromo-phenyl)-2-(2-ethoxy-4-methoxy-phenyl)-4,5-dihydro-imidazol-1-yl]-(4-pyrrolidin-1-yl-piperidin-1-yl)-methanone;

[4,5-Bis-(4-bromo-phenyl)-2-(2-ethoxy-4-methoxy-phenyl)-4,5-dihydro-imidazol-1-yl]-(4-dimethylamino-piperidin-1-yl)-methanone;

[4,5-Bis-(4-bromo-phenyl)-2-(2-ethoxy-4-methoxy-phenyl)-4,5-dihydro-imidazol-1-yl]-(4-isopropyl-piperazin-1-yl)-methanone;

4-[4,5-Bis-(4-bromo-phenyl)-2-(2-ethoxy-4-methoxy-phenyl)-4,5-dihydro-imidazole-1-carbonyl]-piperazin-2-one; and

[4,5-Bis-(4-bromo-phenyl)-2-(2-isopropoxy-4-methoxy-phenyl)-4,5-dihydro-imidazol-1-yl]-piperazin-1-yl-methanone.

32. The compound according to claim 1, selected from:

4-{4,5-Bis-(4-chloro-phenyl)-2-[2-(2-fluoro-ethoxy)-4-methoxy-phenyl]-4,5-dihydro-imidazole-1-carbonyl}-piperazin-2-one;

[4,5-Bis-(4-chloro-phenyl)-2-(2-ethoxy-4-methoxy-phenyl)-4,5-dihydro-imidazol-1-yl]-piperazin-1-yl-methanone hydrochloride;

4,5-Bis-(4-chloro-phenyl)-2-(2-ethoxy-4-methoxy-phenyl)-4,5-dihydro-imidazole-1-carboxylic acid methyl-(2-methylamino-ethyl)-amide, trifluoroacetic acid salt;

4,5-Bis-(4-chloro-phenyl)-2-(2-ethoxy-4-methoxy-phenyl)-4,5-dihydro-imidazole-1-carboxylic acid (2-dimethylamino-ethyl)-methyl-amide, trifluoroacetic acid salt;

4,5-Bis-(4-chloro-phenyl)-2-(2-ethoxy-4-methoxy-phenyl)-4,5-dihydro-imidazole-1-carboxylic acid (2-dimethylamino-ethyl)-amide, trifluoroacetic acid salt;

4,5-Bis-(4-chloro-phenyl)-2-(2-ethoxy-4-methoxy-phenyl)-4,5-dihydro-imidazole-1-carboxylic acid (2-amino-ethyl)-amide, trifluoroacetic acid salt;

[4,5-Bis-(4-chloro-phenyl)-2-(2-ethoxy-4-methoxy-phenyl)-4,5-dihydro-imidazol-1-yl]-(4-pyrrolidin-1-yl-piperidin-1-yl)-methanone hydrochloride;

[4,5-Bis-(4-chloro-phenyl)-2-(4-methoxy-2-propoxy-phenyl)-4,5-dihydro-imidazol-1-yl]-piperazin-1-yl-methanone, trifluoroacetic acid salt;

[4,5-Bis-(4-chloro-phenyl)-2-(2-isopropoxy-4-methoxy-phenyl)-4,5-dihydro-imidazol-1-yl]-(4-methyl-piperazin-1-yl)-methanone hydrochloride; and 4,5-Bis-(4-chloro-phenyl)-2-(2-isopropoxy-4-methoxy-phenyl)-4,5-dihydro-imidazole-1-carboxylic acid (2-morpholin-4-yl-ethyl)-amide hydrochloride.

33. The compound according to claim 1, selected from 4,5-Bis-(4-chloro-phenyl)-2-(2-isopropoxy-4-methoxy-phenyl)-4,5-dihydro-imidazole-1-carboxylic acid (2-piperazin-1-yl-ethyl)-amide hydrochloride;

[4,5-Bis-(4-chloro-phenyl)-2-(2-isobutoxy-4-methoxy-phenyl)-4,5-dihydro-imidazol-1-yl]-piperazin-1-yl-methanone hydrochloride;

[4,5-Bis-(4-chloro-phenyl)-2-(2-isopropoxy-4-methoxy-phenyl)-4,5-dihydro-imidazol-1-yl]-(3-methyl-piperazin-1-yl)-methanone hydrochloride;

{4,5-Bis-(4-chloro-phenyl)-2-[4-methoxy-2-(2-methoxy-ethoxy)-phenyl]-4,5-dihydro-imidazol-1-yl}-piperazin-1-yl-methanone, trifluoroacetic acid salt;

{4,5-Bis-(4-chloro-phenyl)-2-[2-(2-fluoro-ethoxy)-4-methoxy-phenyl]-4,5-dihydro-imidazol-1-yl}-1-piperazin-1-yl-methanone;

{4,5-Bis-(4-chloro-phenyl)-2-[2-(2-fluoro-ethoxy)-4-methoxy-phenyl]-4,5-dihydro-imidazol-1-yl-}-(4-pyrrolidin-1-yl-piperidin-1-yl)-methanone hydrochloride;

2-Amino-1-{4-[4,5-bis-(4-chloro-phenyl)-2-(2-isopropoxy-4-methoxy-phenyl)-4,5-dihydro-imidazole-1-carbonyl]-piperazin-1-yl}-ethanone;

1-{4-[4,5-Bis-(4-chloro-phenyl)-2-(2-isopropoxy-4-methoxy-phenyl)-4,5-dihydro-imidazole-1-carbonyl]-piperazin-1-yl}-2-hydroxy-ethanone;

1-{4-[4,5-Bis-(4-chloro-phenyl)-2-(2-isopropoxy-4-methoxy-phenyl)-4,5-dihydro-imidazole-1-carbonyl]-piperazin-1-yl}-2,3-dihydroxy-propan-1-one; and

[4,5-Bis-(4-chloro-phenyl)-2-(2-isopropoxy-4-methoxy-phenyl)-4,5-dihydro-imidazol-1-yl]-[4-(2,3-dihydroxy-propyl)-piperazin-1-yl]-methanone.

34. The compound according to claim 1, selected from:

4-[4,5-Bis-(4-chloro-phenyl)-2-(2-isopropoxy-4-methoxy-phenyl)-4,5-dihydro-imidazole-1-carbonyl]-piperazine-1-carboxylic acid dimethylamide;

4-[4,5-Bis-(4-chloro-phenyl)-2-(2-isopropoxy-4-methoxy-phenyl)-4,5-dihydro-imidazole-1-carbonyl]-piperazine-1-carboxylic acid amide;

[4,5-Bis-(4-chloro-phenyl)-2-(2,4-diethoxy-phenyl)-4,5-dihydro-imidazol-1-yl]-piperazin-1-yl-methanone;

[4,5-Bis-(4-chloro-phenyl)-2-(2,4-diethoxy-phenyl)-4,5-dihydro-imidazol-1-yl]morpholin-4-yl-methanone;

[4,5-Bis-(4-chloro-phenyl)-2-(2,4-diethoxy-phenyl)-4,5-dihydro-imidazol-1-yl]-[4-(2-hydroxy-ethyl)-piperazin-1-yl]-methanone;

[4,5-Bis-(4-chloro-phenyl)-2-(2,4-diethoxy-phenyl)-4,5-dihydro-imidazol-1-yl]-(4-methyl-piperazin-1-yl)-methanone;

1-{4-[4,5-Bis-(4-chloro-phenyl)-2-(2,4-diethoxy-phenyl)-4,5-dihydro-imidazole-1-carbonyl]-piperazin-1-yl}-ethanone;

[4,5-Bis-(4-chloro-phenyl)-2-(2,4-diethoxy-phenyl)-4,5-dihydro-imidazol-1-yl]-(4-methanesulfonyl-piperazin-1-yl)-methanone;

[4,5-Bis-(4-chloro-phenyl)-2-(2,4-diethoxy-phenyl)-4,5-dihydro-imidazol-1-yl]-(4-pyrrolidin-1-piperidin-1-yl)-methanone;

[4,5-Bis-(4-bromo-phenyl)-2-(2,4-diethoxy-phenyl)-4,5-dihydro-imidazol-1-yl]-(4-methyl-piperazin-1-yl)-methanone.

35. The compound according to claim 1, selected from

[4,5-Bis-(4-bromo-phenyl)-2-(2,4-diethoxy-phenyl)-4,5-dihydro-imidazol-1-yl]-(4-ethyl-piperazin-1-yl)-methanone;

[4,5-Bis-(4-bromo-phenyl)-2-(2,4-diethoxy-phenyl)-4,5-dihydro-imidazol-1-yl]-morpholin-4-yl-methanone;

4-[4,5-Bis-(4-chloro-phenyl)-2-(2,4-diethoxy-phenyl)-4,5-dihydro-imidazole-1-carbonyl]-piperazine-1-carboxylic acid amide;

4-[4,5-Bis-(4-chloro-phenyl)-2-(2,4-diethoxy-phenyl)-4,5-dihydro-imidazole-1-carbonyl]-piperazine-1-carboxylic acid dimethylamide;

[4,5-Bis-(4-chloro-phenyl)-2-(4-dimethylamino-2-ethoxy-phenyl)-4,5-dihydro-imidazol-1-yl]-piperazin-1-yl-methanone;

[4,5-Bis-(4-chloro-phenyl)-2-(2-ethoxy-4-ethyl-phenyl)-4,5-dihydro-imidazol-1-yl]-piperazin-1-methanone;

[4,5-Bis-(4-chloro-phenyl)-2-(2-ethoxy-4-methyl-phenyl)-4,5-dihydro-imidazol-1-yl]-piperazin-1-yl-methanone;

[4,5-Bis-(4-chloro-phenyl)-2-(4-ethyl-2-isopropoxy-phenyl)-4,5-dihydro-imidazol-1-yl]-piperazin-1-yl-methanone;

[4,5-Bis-(4-chloro-phenyl)-2-(2-isopropoxy-4-methyl-phenyl)-4,5-dihydro-imidazol-1-yl]-piperazin-1-yl-methanone;

1-{4-[4,5-Bis-(4-chloro-phenyl)-2-(4-dimethylamino-2-ethoxy-phenyl)-4,5-dihydro-imidazole-1-carbonyl]-piperazin-1-yl}-ethanone; and

[4,5-Bis-(4-chloro-phenyl)-2-(2-ethoxy-5-methyl-phenyl)-4,5-dihydro-imidazol-1-yl]-piperazin-1-yl-methanone, trifluoroacetic acid salt.

36. The compound according to claim 1, selected from:

4-[4,5-Bis-(4-bromo-phenyl)-2-(2-ethoxy-4fluoro-phenyl)-4,5-dihydro-imidazole-1-carbonyl]-piperazin-2-one;

[4,5-Bis-(4-bromo-phenyl)-2-(2-ethoxy-4-fluoro-phenyl)-4,5-dihydro-imidazol-1-yl]-morpholin-4-yl-methanone;

[4,5-Bis-(4-bromo-phenyl)-2-(2-ethoxy-4-fluoro-phenyl)-4,5-dihydro-imidazol-1-yl]-(4-pyrrolidin-1-yl-piperidin-1-yl)-methanone;

[4,5-Bis-(4-bromo-phenyl)-2-(2-ethoxy-4-fluoro-phenyl)-4,5-dihydro-imidazol-1-yl]-(4-dimethylamino-piperidin-1-yl)-methanone;

[4,5-Bis-(4-bromo-phenyl)-2-(2-ethoxy-4-fluoro-phenyl)-4,5-dihydro-imidazol-1-yl]-piperazin-1-methanone;

[4,5-Bis-(4-chloro-phenyl)-2-(2-cyclopentyloxy-4-methoxy-phenyl)-4,5-dihydro-imidazol-1-yl]-piperazin-1-yl-methanone;

{4,5-Bis-(4-chloro-phenyl)-2-[2-(2-dimethylamino-ethoxy)-4-methoxy-phenyl]-4,5-dihydro-imidazol-1-yl}-piperazin-1-yl-methanone;

{4,5-Bis-(4-chloro-phenyl)-2-[2-(2-imidazol-1-yl-ethoxy)-4-methoxy-phenyl]-4,5-dihydro-imidazol-1-yl}-piperazin-1-yl-methanone;

[2-(4-Chloro-2-ethoxy-phenyl)-4,5-bis-(4-chloro-phenyl)-4,5-dihydro-imidazol-1-yl]-piperazin-1-yl-methanone hydrochloride; and

[2-(4-Chloro-2-ethoxy-phenyl)-4,5-bis-(4-chloro-phenyl)-4,5-dihydro-imidazol-1-yl]-(4-methyl-piperazin-1-yl)-methanone hydrochloride.

37. The compound according to claim 1, selected from

[2-(4-Chloro-2-ethoxy-phenyl)-4,5-bis-(4-chloro-phenyl)-4,5-dihydro-imidazol-1-yl]-(4-pyrrolidin-1-yl-piperidin-1-yl)-methanone hydrochloride;

[2-(4-Chloro-2-ethoxy-phenyl)-4,5-bis-(4-chloro-phenyl)-4,5-dihydro-imidazol-1-yl]-morpholin-4-yl-methanone;

1-{4-[2-(4-Chloro-2-ethoxy-phenyl)-4,5-bis-(4-chloro-phenyl)-4,5-dihydro-imidazole-1-carbonyl]-piperazin-1-yl}-ethanone;

[2-(4-Chloro-2-ethoxy-phenyl)-4,5-bis-(4-chloro-phenyl)-4,5-dihydro-imidazol-1-yl]-[4-(2-hydroxy-ethyl)-piperazin-1-yl]-methanone hydrochloride;

4-[2-(4-Chloro-2-ethoxy-phenyl)-4,5-bis-(4-chloro-phenyl)-4,5-dihydro-imidazole-1-carbonyl]-piperazin-2-one;

[4,5-Bis-(4-chloro-phenyl)-2-(4-ethoxy-2-isopropoxy-phenyl)-4,5-dihydro-imidazol-1-yl]-piperazin-1-yl-methanone;

[4,5-Bis-(4-chloro-phenyl)-2-(2-ethoxy-5-methoxy-phenyl)-4,5-dihydro-imidazol-1-yl]-piperazin-1-yl-methanone, trifluoroacetic acid salt;

[4,5-Bis-(4-chloro-phenyl)-2-(2-ethoxy-5-methoxy-phenyl)-4,5-dihydro-imidazol-1-yl]-(4-methanesulfonyl-piperazin-1-yl)-methanone;

[4,5-Bis-(4-chloro-phenyl)-2-(2-ethoxy-5-methoxy-phenyl)-4,5-dihydro-imidazol-1-yl]-[4-(2-hydroxy-ethyl)-piperazin-1-yl]-methanone hydrochloride; and

[4,5-Bis-(4-chloro-phenyl)-2-(2,5-diethoxy-phenyl)-4,5-dihydro-imidazol-1-yl]-piperazin-1-yl-methanone hydrochloride.

38. The compound of claim 1, selected from

[4,5-Bis-(4-chloro-phenyl)-2-(2,5-diethoxy-phenyl)-4,5-dihydro-imidazol-1-yl]-(4-methanesulfonyl-piperazin-1-yl)-methanone;

[4,5-Bis-(4-chloro-phenyl)-2-(4-ethoxy-2-isopropoxy-phenyl)-4,5-dihydro-imidazol-yl]-[4-(2-hydroxy-ethyl)-piperazin-1-yl]-methanone;

4-[4,5-Bis-(4-chloro-phenyl)-2-(4-ethoxy-2-isopropoxy-phenyl)-4,5-dihydro-imidazole-1-carbonyl]-piperazin-2-one;

[4,5-Bis-(4-chloro-phenyl)-2-(5-ethoxy-2-isopropoxy-phenyl)-4,5-dihydro-imidazol-1-yl]-piperazin-1-yl-methanone;

[4,5-Bis-(4-chloro-phenyl)-2-(5-ethoxy-2-isopropoxy-phenyl)-4,5-dihydro-imidazol-1-yl]-(4-methanesulfonyl-piperazin-1-yl)-methanone;

[4,5-Bis-(4-chloro-phenyl)-2-(5-ethoxy-2-isopropoxy-phenyl)-4,5-dihydro-imidazol-1-yl]-[4-(2-hydroxy-ethyl)-piperazin-1-yl]-methanone hydrochloride;

1-{4-[4,5-Bis-(4-chloro-phenyl)-2-(4-ethoxy-2-isopropoxy-phenyl)-4,5-dihydro-imidazole-1-carbonyl]-piperazin-1-yl}-ethanone;

1-{4-[4,5-Bis-(4-chloro-phenyl)-2-(5-ethoxy-2-isopropoxy-phenyl)-4,5-dihydro-imidazole-1-carbonyl]-piperazin-1-yl}-ethanone;

[4,5-Bis-(4-chloro-phenyl)-2-(4-ethoxy-2-isopropoxy-phenyl)-4,5-dihydro-imidazol-1-yl]-(4-pyrrolidin-1-yl-piperidin-1-yl)-methanone; and

[4,5-Bis-(4-chloro-phenyl)-2-(2-isopropoxy-5-methoxy-phenyl)-4,5-dihydro-imidazol-1-yl]-piperazin-1-yl-methanone, trifluoroacetic acid salt.

39. The compound selected from claim 1, selected from 4,5-Bis-(4-chloro-phenyl)-2-(2,4-diisopropoxy-phenyl)4,5-dihydro-imidazol-1-yl]-piperazin-1-yl-methanone;

[4,5-Bis-(4-chloro-phenyl)-2-(2,5-diisopropoxy-phenyl)-4,5-dihydro-imidazol-1-yl]-piperazin-1-yl-methanone hydrochloride;

1-[4,5-Bis-(4-chloro-phenyl)-2-(2-methoxy-5-morpholin-4-yl-methyl-phenyl)-4,5-dihydro-imidazol-1-yl]-2-methyl-propan-1-one;

1-[4,5-Bis-(4-chloro-phenyl)-2-(3-hydroxymethyl-5-methoxy-phenyl)-4,5-dihydro-imidazol-1-yl]-methyl-propan-1-one;

1-[4,5-Bis-(4-chloro-phenyl)-2-(3-hydroxymethyl-5-methoxymethyl-phenyl)-4,5-dihydro-imidazol-1-yl]-ethanone;

1-[4,5-Bis-(4-chloro-phenyl)-2-(3-methoxy-5-methoxymethyl-phenyl)-4,5-dihydro-imidazol-1-yl]-2-methyl-propan-1-one;

3-[4,5-Bis-(4-chloro-phenyl)-1-isobutyryl-4,5-dihydro-1H-imidazol-2-yl]-5-methoxymethyl-benzoic acid;

1-[4,5-Bis-(4-chloro-phenyl)-2-(5-ethoxymethyl-2,4-dimethoxy-phenyl)-4,5-dihydro-imidazol-1-yl]-2-methyl-propan-1-one;

[4,5-Bis-(4-chloro-phenyl)-2-(2-ethoxy-6-methoxy-phenyl)-4,5-dihydro-imidazol-1-yl]-piperazin-1-yl-methanone; and

[4,5-bis-(4-chloro-phenyl)-2-(5-ethoxymethyl-2,4-dimethoxy-phenyl)-4,5-dihydro-imidazol-1-yl]-piperazin-1-yl-methanone.

40. The compound of claim 14, selected from

[4,5-Bis-(4-bromo-phenyl)-2-(2-methoxy-phenyl)-4,5-dihydro-imidazol-1-yl]-[4-(2-hydroxy-ethyl)-piperazin-1-yl]-methanone;

1-[5-(4-Chloro-phenyl)-2-(4-methoxy-phenyl)-4-(4-nitro-phenyl)-4,5-dihydro-imidazol-1-yl]-2-methyl-propan-1-one;

1-[4-(4-chloro-phenyl)-2-(4-methoxy-phenyl)-5-(4-nitro-phenyl)-4,5-dihydro-imidazol-1-yl]-2-methyl-propan-1-one;

1-[4,5-Bis-(4-chloro-phenyl)-2-(2-isopropoxy-phenyl)-4,5-dihydro-imidazol-1-yl]-2-methyl-propan-1-one;

[4,5-Bis-(4-chloro-phenyl)-2-(2-isopropoxy-phenyl)-4,5-dihydro-imidazol-1-yl]-(4-pyrrolidin-1-yl-piperidin-1-yl)-methanone;

[4,5-Bis-(4-chloro-phenyl)-2-(2-isopropoxy-phenyl)-4,5-dihydro-imidazol-1-yl]-piperazin-1-yl-methanone;

[4,5-Bis-(4-chloro-phenyl)-2-(2-isopropoxy-phenyl)-4,5-dihydro-imidazol-1-yl]-(4-dimethylamino-piperidin-1-yl)-methanone; [1,4']Bipiperidinyl-1'-yl-[4,5-bis-(4-chloro-phenyl)-2-(2-isopropoxy-phenyl)-4,5-dihydro-imidazol-1-yl]-methanone;

[4,5-Bis-(4-chloro-phenyl)-2-(2-isopropoxy-phenyl)-4,5-dihydro-imidazol-1-yl]-[4-(2-hydroxy-ethyl)-piperazin-1-yl]-methanone; and {(4,5-Bis-(4-chloro-phenyl)-2-[2-(2-methyl-butoxy)-phenyl]-4,5-dihydro-imidazol-1-yl}-piperazin-1-yl-methanone.

41. The compound of claim 14, selected from

[4,5-Bis-(4-chloro-phenyl)-2-(2-pentyloxy-phenyl)-4,5-dihydro-imidazol-1-yl]-piperazin-1-yl-methanone;

[4,5-Bis-(4-chloro-phenyl)-2-(3-ethoxy-phenyl)-4,5-dihydro-imidazol-1-yl]-piperazin-1-yl-methanone, trifluoroacetic acid salt;

[4,5-Bis-(4-chloro-phenyl)-2-(3-isopropoxy-phenyl)-4,5-dihydro-imidazol-1-yl]-piperazin-1-yl-methanone, trifluoroacetic acid salt;

1-{4-[4,5-Bis-(4-bromo-phenyl)-2-(2-ethoxy-phenyl)-4,5-dihydro-imidazole-1-carbonyl]-piperazin-1-yl}-ethanone;

[4,5-Bis-(4-bromo-phenyl)-2-(2-ethoxy-phenyl)-4,5-dihydro-imidazol-1-yl]-[4-(2-hydroxy-ethyl)-piperazin-1-yl]-methanone;

1-{4-[4,5-Bis-(4-bromo-phenyl)-2-(2-isopropoxy-phenyl)-4,5-dihydro-imidazole-1-carbonyl]-piperazin-1-yl}-ethanone; and

[4,5-Bis-(4-bromo-phenyl)-2-(2-isopropoxy-phenyl)-4,5-dihydro-imidazol-1-yl]-[4-(2-hydroxy-ethyl)-piperazin-1-yl]-methanone.

* * * * *

UNITED STATES PATENT AND TRADEMARK OFFICE
CERTIFICATE OF CORRECTION

PATENT NO. : 6,734,302 B2
DATED : May 11, 2004
INVENTOR(S) : Norman Kong, Emily Aijun Liu and Binh Thanh Vu It is certified that error appears in the above-identified patent and that said Letters Patent is hereby corrected as shown below:

Column 62,
Line 26, delete "-[4,5-Bis-(4-bromo-phenyl)-2-(2-ethoxy-4fluoro-" and insert -- -[4,5-Bis-(4-bromo-phenyl)-2-(2-ethoxy-4-fluoro- --.
Line 40, delete "phenyl)-4,5-dihydro-imidazol-1-yl]-piperazin-1-" and insert -- phenyl)-4,5-dihydro-imidazol-1-yl]-piperazin-1-yl- --.

Column 64,
Line 42, delete "{(4,5-Bis-(4-chloro-phenyl)-2-[2-(2-methyl-butoxy)-" and insert -- {4,5-Bis-(4-chloro-phenyl)-2-[2-(2-methyl-butoxy)- --.

Signed and Sealed this

Twenty-first Day of December, 2004

JON W. DUDAS
*Director of the United States Patent and Trademark Office*